(12) United States Patent
Renz et al.

(10) Patent No.: US 7,700,833 B2
(45) Date of Patent: Apr. 20, 2010

(54) PROCESS FOR THE PRODUCTION OF UNSATURATED FATTY ACIDS

(75) Inventors: Andreas Renz, Limburgerhof (DE); Martijn Gipmans, Potsdam (DE); Ivo Feussner, Göttingen (DE); Claire-Lise Rosenfield, Geneva, NY (US); Douglas C. Knipple, Geneva, NY (US)

(73) Assignee: Cornell University, Ithaca, NY (US)

( * ) Notice: Subject to any disclaimer, the term of this patent is extended or adjusted under 35 U.S.C. 154(b) by 1115 days.

(21) Appl. No.: 10/505,590

(22) PCT Filed: Feb. 27, 2003

(86) PCT No.: PCT/US03/05788

§ 371 (c)(1),
(2), (4) Date: Aug. 25, 2004

(87) PCT Pub. No.: WO03/074715

PCT Pub. Date: Sep. 12, 2003

(65) Prior Publication Data

US 2006/0078973 A1    Apr. 13, 2006

(30) Foreign Application Priority Data

Mar. 1, 2002    (DE) ................................ 102 08 812

(51) Int. Cl.
C12N 15/82    (2006.01)
A01H 5/00    (2006.01)
(52) U.S. Cl. ........................................ 800/281; 800/298
(58) Field of Classification Search .................. None
See application file for complete search history.

(56) References Cited

U.S. PATENT DOCUMENTS

| | | | |
|---|---|---|---|
| 5,876,994 A * | 3/1999 | Knipple et al. | ............... 435/189 |
| 6,048,838 A | 4/2000 | Ensign et al. | |
| 6,766,817 B2 | 7/2004 | Da Silva | |
| 7,057,090 B1 * | 6/2006 | Zilinskas et al. | ............ 800/294 |

FOREIGN PATENT DOCUMENTS

| | | |
|---|---|---|
| CA | 2 378 423 A1 | 11/2001 |
| WO | WO-94/16690 A1 | 8/1994 |
| WO | WO-96/06605 A1 | 3/1996 |
| WO | WO-97/32008 A1 | 9/1997 |
| WO | WO-97/46118 A1 | 12/1997 |
| WO | WO-97/46230 A1 | 12/1997 |
| WO | WO-99/20123 A1 | 4/1999 |
| WO | WO-99/32604 A1 | 7/1999 |
| WO | WO-99/43604 A2 | 9/1999 |
| WO | WO-99/64616 A2 | 12/1999 |
| WO | WO-99/64616 A3 | 12/1999 |
| WO | WO-00/11012 A1 | 3/2000 |
| WO | WO-01/00846 A2 | 1/2001 |
| WO | WO-01/02591 A1 | 1/2001 |
| WO | WO-01/92489 A2 | 12/2001 |
| WO | WO-01/92489 A3 | 12/2001 |

OTHER PUBLICATIONS

Sequence Database Accession AY049741, Jan. 23, 2002.*
Broun et al, Science 282: 1315, Nov. 13, 1998.*
Van de Loo et al, PNAS, USA 92:6743-6747, Jul. 1995.*
Doerks et al, TIG 14(6):248-250, Jun. 1998.*
Smith et al, Nature Biotechnology 15: 1222-1223, Nov. 15, 1997.*
Brenner, S.E., TIG 15(4): 132-133, Apr. 1999.*
Bork et al, TIG 12(10): 425-427, Oct. 1996.*
De Luca V, AgBiotech News and Information 5(6): 225N-229N, 1993.*
Moon et al, Lipids 35 (5): 471-479, 2000.*
Sequence Database Accession AAX21400, Mar. 2, 1999.*
Adlof, R. O., et al., "Biosynthesis of Conjugated Linoleic Acid in Humans", Lipids, vol. 35, No. 2, 2000, pp. 131-135.
Banni, S., et al., "Decrease in linoleic acid metabolites as a potential mechanism in cancer risk reduction by conjugated linoleic acid", Carcinogenesis, vol. 20, No. 6, 1999, pp. 1019-1024.
Bonaldo, M., et al., "Normalization and Subtraction: Two Approaches to Facilitate Gene Discovery", Genome Research, vol. 6, 1996, pp. 791-806.
Borson, N. D., et al., "A Lock-docking Oligo (dT) Primer for 5' and 3' Race PCR", PCR Methods and Applications, vol. 2, 1992, pp. 144-148.
Cahoon, E. B., et al., "Production of Fatty Acid Components of Meadowfoam Oil in Somatic Soybean Embryos", Plant Physiology, vol. 124, 2000, pp. 243-251.
Cahoon, E. B., et al., "Formation of Conjugated $\Delta^8$, $\Delta^{10}$-Double Bonds by $\Delta^{12}$-Oleic-acid Desaturase-related Enzymes", The Journal of Biological Chemistry, vol. 276, No. 4, 2001, pp. 2637-2643.
Carninci, P., et al., "Normalization and Subtraction of Cap-Trapper-Selected cDNAs to Prepare Full-Length cDNA Libraries for Rapid Discovery of New Genes", Genome Research, vol. 10, 2000, pp. 1617-1630.
Kepler, C. R., et al., "Biohydrogenation of Unsaturated Fatty Acids", The Journal of Biological Chemistry, vol. 242, No. 24, 1967, pp. 5686-5692.

(Continued)

Primary Examiner—Elizabeth F McElwain
(74) Attorney, Agent, or Firm—Connolly Bove Lodge & Hutz LLP

(57) ABSTRACT

The invention relates to processes for the production of unsaturated fatty acids, preferably of conjugated polyunsaturated fatty acids such as conjugated linoleic acid (CLA), by the recombinant expression of desaturases from insects of the order Lepidoptera. Expression preferably takes place in an organism selected from the group of the plant organisms, yeasts, fungi and algae. Also, according to the invention are recombinant expression cassettes for the recombinant expression of desaturases from insects of the order Lepidoptera, and the transgenic organisms transformed with these.

13 Claims, No Drawings

OTHER PUBLICATIONS

Chin, S. F., et al., "Dietary Sources of Conjugated Dienoic Isomers of Linoleic Acid, a Newly Recognized Class of Anticarcinogens", Journal of Food Composition and Analysis, vol. 5, 1992, pp. 185-197.

Chu, Z-L., et al., "Suppression of tumor necrosis factor-induced cell death by inhibitor of apoptosis c-IAP2 is under NF-κB control", Proc. Natl. Acad. Sci. USA, vol. 94, 1997, pp. 10057-10062.

Crombie, L., et al., "Origins of Conjugated Triene Fatty Acids. The Biosynthesis of Calendic Acid by *Calendula officinalis*", Journal of the Chemical Society, Chemical Communications, No. 15, 1984, pp. 953-955.

Crombie, L., et al., "The Biosynthesis of Calendic Acid, Octadeca-(8E, 10E, 12Z)-trienoic Acid, by Developing Marigold Seeds: Origins of (E,E,Z) and (Z,E,Z) Conjugated Triene Acids in Higher Plants", J. Chem. Soc. Perkin Trans. I, 1985, pp. 2425-2434.

Dalbøge, H., "Expression cloning of fungal enzyme genes; a novel approach for efficient isolation of enzyme genes of industrial relevance", FEMS Microbiology Reviews, vol. 21, 1997, pp. 29-42.

Dhiman, T.R., et al., "Conjugated Linoleic Acid Content of Milk from Cows Fed Different Diets", J. Dairy Sci., vol. 82, 1999, pp. 2146-2156.

Fritsche, K., et al, "Isolation and characterization of a calendic acid producing (8,11)-linoleoyl desaturase", FEBS Letters, vol. 462, 1999, pp. 249-253.

Knipple, D. C., et al., "*Pectinophora gossypiella* acyl-CoA desaturase PgosVASQ mRNA, partial cds.", May 15, 2002, Accession No. AF482921.

Gillissen, B., et al., "A New Family of High-Affinity Transporters for Adenine, Cytosine, and Purine Derivatives in Arabidopsis", The Plant Cell, vol. 12, 2000, pp. 291-300.

Gubler, U., et al., "A simple and very efficient method for generating cDNA libraries", Gene, vol. 25, 1983, pp. 263-269.

Herrler, M., "Use of SMART-generated cDNA for Differential Gene Expression Studies", J. Mol. Med., vol. 78, 2000, p. B23.

Hudson, C., et al., "Xsoxl7α and -β Mediate Endoderm Formation in Xenopus", Cell, vol. 91, 1997, pp. 397-405.

Kepler, C. R., et al., "Intermediates and Products of the Biohydrogenation of Linoleic Acid by *Butyrivibrio fibrisolvene*", The Journal of Biological Chemistry, vol. 241, No. 6, 1966, pp. 1350-1354.

Knipple, D. C., et al., "Evolution of the Integral Membrane Desaturase Gene Family in Moths and Flies", Genetics, vol. 162, 2002, pp. 1737-1752.

Lemaire, P., et al., "Expression Cloning of *Siamois*, a Xenopus Homeobox Gene Expressed in Dorsal-Vegetal Cells of Blastulae and Able to Induce a Complete Secondary Axis", Cell, vol. 81, 1995, pp. 85-94.

Liu, W., et al., "Gene characterized for membrane desaturase that produces (E)-11 isomers of mono- and diunsaturated fatty acids", Proc. Natl. Acad. Sci. USA, vol. 99, No. 2, 2002, pp. 620-624.

Longman, A. J., et al., "An unusual desaturase in *Aquilegia vulgaris*", Biochemical Society Transactions, vol. 28, 2000, pp. 641-643.

Lotan, T., et al., "Cloning and expression in *Escherichia coli* of the gene encoding β-C-4-oxygenase, that converts β-carotene to the ketocarotenoid canthaxanthin in *Haematococcus pluvialis*", FEBS Letters, vol. 364, 1995, pp. 125-128.

Lustig, K. D., et al., "Expression cloning of a *Xenopus* T-related gene (*Xombi*) involved in mesodermal patterning and blastopore lip formation", Development, vol. 122, 1996, pp. 4001-4012.

Masu, Y., et al., "cDNA cloning of bovine substance-K receptor through oocyte expression system", Nature, vol. 329, No. 29, 1987, pp. 836-838.

Mueller, C. G. F., et al., "Polymerase Chain Reaction Selects a Novel Disintegrin Proteinase from CD40-Activated Germinal Center Dendritic Cells", J. Exp. Med., vol. 186, No. 5, 1997, pp. 655-663.

Park, Y., et al., "Effect of Conjugated Linoleic Acid on Body Composition in Mice", Lipids, vol. 32, No. 8, 1997, pp. 853-858.

Park, Y., et al., "Evidence That the *trans*-10, *cis*-12 Isomer of Conjugated Linoleic Acid Induces Body Composition Changes in Mice", Lipids, vol. 34, No. 3, 1999, pp. 235-241.

Qiu, X., et al., "Identification and Analysis of a Gene from *Calendula officinalis* Encoding a Fatty Acid Conjugase", Plant Physiology, vol. 125, 2001, pp. 847-855.

Rankoff, D., et al., "Fatty Acid Composition of *Thalictrum* L. Seed Oils", J. Amer. Oil Chem. Soc., vol. 48, 1971, pp. 700-701.

Roelofs, W. L., "Chemistry of sex attraction", Proc. Natl. Acad. Sci., vol. 92, 1995, pp. 44-49.

Roelofs, W. L., et al., "Pheromone Biosynthesis In Lepidoptera", Journal of Chemical Ecology, vol. 14, No. 11, 1988, pp. 2019-2031.

Santora, J. E., et al., "Trans-Vaccenic Acid Is Desaturated to Conjugated Linoleic Acid in Mice", J. Nutr., vol. 130, 2000, pp. 208-215.

Simonsen, H., et al., "Cloning by function: expression cloning in mammalian cells", Trends Pharmacol. Sci., vol. 15, 1994, pp. 437-441.

Smith, W. C., et al., "Expression cloning of noggin, a New Dorsalizing Factor Localized to the Spemann Organizer in Xenopus Embryos", Cell, vol. 70, 1992, pp. 829-840.

Soares, M. B., et al., "Construction and characterization of a normalized cDNA library", Proc. Natl. Acad. Sci. USA, vol. 91, 1994, pp. 9228-9232.

Thompson, H., et al., "Morphological and Biochemical Status of the Mammary Gland as Influenced by Conjugated Linoleic Acid: Implication for a Reduction in Mammary Cancer Risk", Cancer Research, vol. 57, 1997, pp. 5067-5072.

Tillman, J. A., et al., "Insect pheromones-an overview of biosynthesis and endocrine regulation", Insect Biochemistry and Molecular Biology, vol. 29, 1999, pp. 481-514.

Von Stein, O. D., et al., "A high throughput screening for rarely transcribed differentially expressed genes", Nucleic Acids Research, vol. 25, No. 13, 1997, pp. 2598-2602.

Wong, B. R., et al., "Trance Is a Novel Ligand of the Tumor Necrosis Factor Receptor Family That Activates c-Jun N-terminal Kinase in T Cells", The Journal of Biological Chemistry, vol. 272, No. 40, 1997, pp. 25190-25194.

Wong, G. G., et al., "Human GM-CSF: Molecular Cloning of the Complementary DNA and Purification of the Natural and Recombinant Proteins", Science, vol. 228, pp. 810-815.

Yokomizo, T., et al., "A G-protein-coupled receptor for leukotriene $B_4$ that mediates chemotaxis", Nature, vol. 387, 1997, pp. 620-624.

Shen, Z., et al., "Characterization of a Novel gut-specific Chitinase Gene from the Human Malaria Vector *Anopheles gambiae*", The Journal of Biological Chemistry, vol. 272, No. 46, 1997, pp. 28895-28900.

Ando, T., "Biosynthetic Pathway of Bombykol, the Sex Pheromone of the Female Silkworm Moth", Agric. Biol. Chem., vol. 52, No. 2, 1988, pp. 473-478.

Knipple, D. C., et al., "Cloning and functional expression of a cDNA encoding a pheromone gland-specific acyl-CoA $\Delta^{11}$-desaturase of the cabbage looper moth, *Trichoplusia ni*", Proc. Natl. Acad. Sci., vol. 95, 1998, pp. 15287-15292.

Wilson, T. A., et al., "Conjugated linoleic acid reduces early aortic atherosclerosis greater that linoleic acid in hypercholesterolemic hamsters", Nutrition Research, vol. 20, 2000, pp. 1795-1805.

Rosenfield, C.-L., et al., "Structural and functional conservation and divergence among acyl-CoA desaturases of two noctuid species, the corn earworm, *Helicoverpa zea*, and the cabbage looper, *Trichoplusia ni*", Insect Biochemistry and Molecular Biology, vol. 31, 2001, pp. 949-964.

Liu, W., et al., "Cloning and functional expression of a cDNA encoding a metabolic acyl-CoA Δ9-desaturase of the cabbage looper moth, *Trichoplusia ni*", Insect Biochemistry and Molecular Biology, vol. 29, 1999, pp. 435-443.

\* cited by examiner

PROCESS FOR THE PRODUCTION OF UNSATURATED FATTY ACIDS

RELATED APPLICATIONS

This application is a national stage application (under 35 U.S.C. §371) of PCT/US03/05788 filed Feb. 27, 2003, which claims benefit of German application 102 08 812.8 filed Mar. 1, 2002.

FIELD OF THE INVENTION

The invention relates to processes for the production of unsaturated fatty acids, preferably of conjugated polyunsaturated fatty acids such as conjugated linoleic acid (CLA), by the recombinant expression of desaturases from insects of the order Lepidoptera. Expression preferably takes place in an organism selected from the group of the plant organisms, yeasts, fungi and algae. Also according to the invention are recombinant expression cassettes for the recombinant expression of desaturases from insects of the order Lepidoptera, and the transgenic organisms transformed with these.

DESCRIPTION OF THE BACKGROUND

Fatty acids and triglycerides are used widely in the food industry, in animal nutrition, in cosmetics and in the pharmaceutical sector. Especially valuable and sought-after unsaturated fatty acids are what are known as conjugated unsaturated fatty acids. Conjugated polyunsaturated fatty acids are relatively rare in comparison with other polyunsaturated fatty acids. Examples of conjugated fatty acids are the conjugated linoleic acids (CLA; conjugated linoleic acid), α-parinaric acid (18:4 octadecatetraenoic acid), eleostearic acid (18:3 octadecatrienoic acid), the conjugated linolenic acids, dimorphecolic acid and calendulic acid (see scheme 1).

Scheme 1: Conjugated polyunsaturated fatty acids

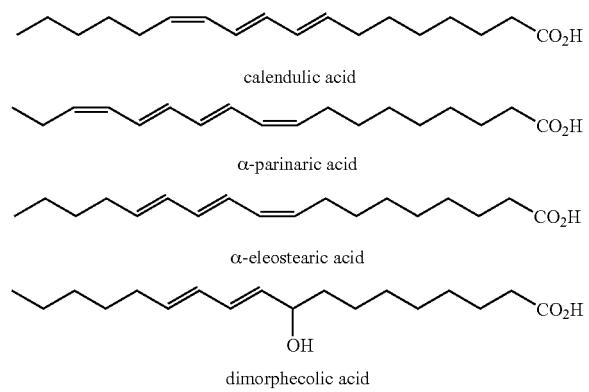

CLA is a collective term for positional and structural isomers of linoleic acid which are distinguished by a conjugated double bond system starting at carbon atom 8, 9, 10 or 11. Some examples are shown in scheme 2.

Geometric isomers exist for each of these positional isomers, that is to say cis-cis, trans-cis, cis-trans, trans-trans.

Scheme 2: Four isomers of the conjugated linoleic acids

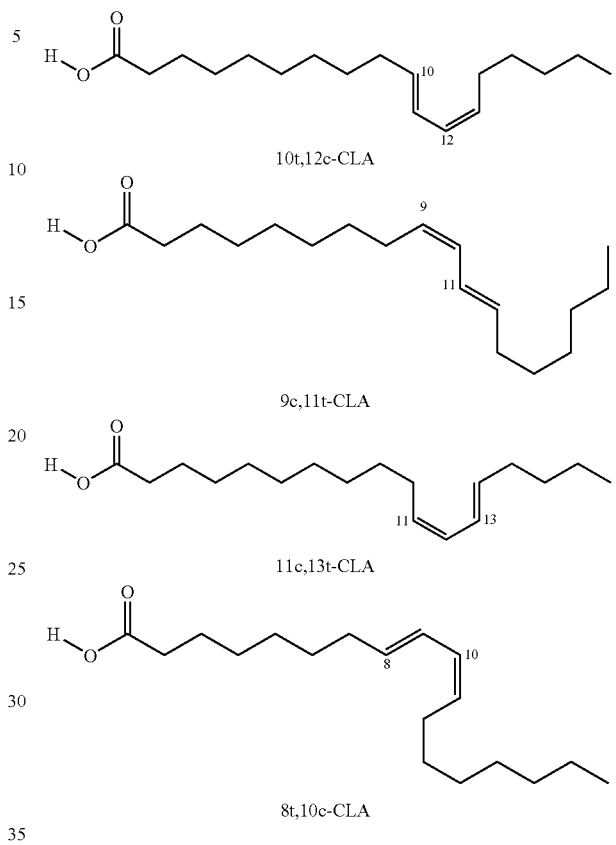

The CLA isomers (9Z,11E)-CLA and (10E,12Z)-CLA are known as the biologically active isomers. CLA is found predominantly in foodstuffs of animal origin. High CLA concentrations are found in particular in the meat and in dairy products of ruminants: approx. 3 to 4 mg of CLA/g fat in beef and lamb (Chin et al. (1992) J Food Comp Anal 5:185-197) and approx. 3 to 7 mg of CLA/g fat in dairy products (Dhiman et al. (1999) J Dairy Sci 82:2146-56), where (9Z,11E)-CLA at a concentration of approximately 80% is in each case the predominant isomer. Higher plants only contain traces of CLA, with the two biologically active CLA isomers not having been found in plants to date.

A range of positive effects have been found for CLA; thus, the administration of CLA reduces the body fat in humans and animals and increases the rate at which feed is converted into body weight in animals (Park et al. (1997) Lipids 32:853-858; Park et al. (1999) Lipids 34:235-241; WO 94/16690; WO 96/06605; WO 97/46230; WO 97/46118). The administration of CLA also has a positive effect on, for example, allergies (WO 97/32008) or cancer (Banni et al. (1999) Carcinogenesis 20: 1019-1024, Thompson et al. (1997) Cancer Res 57:5067-5072). An antiarteriosclerotic effect of CLA has also been confirmed (Wilson et al. (2000) Nutr Res 20:1795-1805). Studies were carried out with isomers and with isomer mixtures.

CLA can be synthesized by alkaline isomerization of linoleic acid. Vegetable oils with a high linoleic acid content are predominantly used on an industrial scale, for example sunflower oil, safflower oil. Heating to above 180° C. under alkaline conditions catalyzes two reactions:

(1) the fatty acid ester bonds of the triglyceride skeleton are hydrolyzed and the free fatty acids are liberated,
(2) unconjugated unsaturated fatty acids with two or more double bonds are conjugated.

Commercially available CLA oils contain a mixture of various CLA isomers and other saturated and unsaturated fatty acids. Owing to the presence of these biologically inactive and unnatural isomers, laborious purification of the biologically active isomers (9Z,11E) CLA and (10E,12Z) CLA is required, or it must be demonstrated that the isomer mixture does not represent a health hazard for humans and animals. It has hitherto not been possible to produce individual CLA isomers by alkaline isomerization in an economically relevant process. Fractional crystallization makes it possible to concentrate the isomers (9Z,11E)-CLA and (10E,12Z)-CLA, respectively. However, it is not possible in all of the abovementioned processes to prepare individual isomers in high quality. In the abovementioned processes, the reaction products are usually converted into methyl or ethyl esters so that the natural form of CLA, viz. the free fatty acids or the triacyl glyceride, are not available.

These disadvantages of chemical conversion can be overcome by carrying out the conversion of linoleic acid into CLA by biocatalysis. Various microorganisms of the rumen of ruminants are capable for example of converting linoleic acid into CLA during the biohydrogenation process. This is effected by the enzymatic activity of a CLA isomerase, inter alia. This enzymatic activity was described in *Butyrivibrio fibrisolvens* (Kepler and Tovee (1966) J Biol Chem 241:1350), *Propionibacterium acnes* (Deng et al., 1st International Conference on CLA, 2001, Alesund, Norway), *Clostridium sporogenes* and *Lactobacillus reuteri* (WO 99/32604; WO 01/00846). The CLA isomerases described to date utilize free fatty acids as substrate. The genes encoding CLA isomerase from *Lactobacillus reuteri* and *Propionibacterium acnes* were cloned, and the isomerase from *Propionibacterium* was expressed functionally in heterologous microorganisms. While the bioconversion of linoleic acid into CLA by microorganisms has qualitative advantages over alkaline isomerization, it is economically disadvantageous, owing to the fermentation costs, and only yields free fatty acids, but no triglycerides. However, free fatty acids have disadvantageous olfactory properties and are essentially unsuitable for use in the food- and feed sector. A subsequent conversion of the free fatty acids—for example glycerol or gylcerides with lipase catalysis—is possible, but complicated.

The methods which are based on bacterial CLA isomerases can always be applied to other organisms. So far, it has been shown that CLA isomerases convert free linoleic acid into CLA (Cepler and Tove (1967) J Biochem Chem 242:5686-5692). In higher organisms such as, for example, plants, linoleic acid predominantly exists in esterified form. Lipids such as triacyl glycerides constitute the storage form, while thioesters such as acyl-CoA constitute the active form of the fatty acid.

Fatty acids with trans double bonds are extremely rare. The seed oil of some plants contains fatty acids with double bonds in the trans position. Thus, an E5-fatty acid has been detected in the seed oil of various *Thalictrum* species (Rankoff et al. (1971) J Amer Oil Chem Soc 48:700-701). Moreover, E5-desaturase activity has been described in *Aquilegia vulgaris* (Longman et al. (2000) Biochem Soc Trans 28:641-643). However, no plants have been described which contain either trans-vaccenic acid (E11-octadecenoic acid) or E10-octadecenoic acid.

It is known that the desaturation of fatty acids in plants can take place mainly by two mechanisms:

(1) in plastids, fatty acid ACP esters are desaturated by a soluble desaturase, predominantly at position 9, and
(2) on the endoplasmic reticulum, membrane lipids, especially phosphatidyl cholins, are preferentially further desaturated at positions 6, 12 and 15 by membrane-bound desaturases.

In some plants, conjugated fatty acids are produced by the activity of a conjugase (Crombie et al. (1984) J Chem Soc Chem Commun 15:953-955; Crombie et al. (1985) J Chem Soc Perkin Trans 1:2425-2434; Fritsche et al. (1999) FEBS Letters 462: 249-253; Cahoon et al. (2001) J Biol Chem 276:2637-2643; Qiu et al. (2001) Plant Physiol 125:847-855). The biosynthesis of conjugated fatty acids such as calendulic acid, eleostearic acid or punicic acid proceeds via the desaturation of oleic acid to linoleic acid by a D12-desaturase and a further desaturation in conjunction with a rearrangement of the Z9- or Z12-double bond to the conjutrienic fatty acid by a specific conjutriene-forming desaturase (conjugase). Besides the production of calendulic acid, Qui et al. (2001) Plant Physiol 125:847-855) also describe the production of conjugated linoleic acid by the enzymatic activity of conjugase. However, the disadvantage of this secondary activity is that the enzymatic activity gives rise to the undesired 8,10-isomer of the conjugated linoleic acid.

Pheromone desaturases from lepidopterans display a wide range of substrate specificities and desaturation mechanisms (Roelofs and Wolf (1988) J Chem Ecol 14:2019-2031; Roelofs (1995) Proc Nat Acad Sci USA 92:44-49; Tillman et al. (1999) Insect Biochem 29:481-514). These enzyme activities cause the production of unusual unsaturated fatty acid CoA derivatives with a wide range of chain lengths and with double bonds at different positions and with different configurations. They act as starting material for the biosynthesis of pheromones. Liu et al. describe an E11-desaturase from the pheromone gland of a moth species ("light brown apple moth"), which is likely to play a role in pheromone biosynthesis (Liu W T et al. (2002) Proc Natl Acad Sci USA 99(2): 620-624.

Knipple et al. (Genetics 2002 December; 162(4):1737-52) compare various integral membrane desaturases from moths and flies which have been isolated from the pheromone glands of these insects. A fragment of an acyl-CoA desaturase (PgosVASQ) from *Pectinophora gossypiella* is described. The corresponding sequence has been deposited under the GeneBank Acc. No.: AF482921. Neither the complete sequence nor the specific activity of the desaturase are described. It was named merely on the basis of homologies with other desaturases.

SUMMARY OF THE INVENTION

It is an object of the present invention to provide novel processes which lead to triglycerides which are high in unsaturated fatty acids, preferably conjugated polyunsaturated fatty acids such as CLA. We have found that this object is achieved by the present invention.

DESCRIPTION OF THE INVENTION

A first subject matter of the invention relates to processes for the production of triglycerides comprising unsaturated fatty acids by the recombinant expression of at least one fatty acid desaturase from insects of the order Lepidoptera.

Preferably, the process for the production of triglycerides comprising unsaturated fatty acids comprises the recombinant expression of at least one fatty acid desaturase from insects of the order Lepidoptera in an organism selected from the group of the plant organisms, yeasts, fungi and algae.

In a preferred embodiment, fatty acid desaturases are employed which are capable of generating a double bond at position C8, C9, C10, C11 or C12 in fatty acids, fatty acid CoA esters or other fatty acid derivatives. Especially preferred are fatty acid desaturases which are capable of specifically generating a cis or trans double bond in fatty acids, fatty acid CoA esters or other fatty acid derivatives with a fatty acid chain length of 16 or 18 C atoms. Very especially preferred are fatty acid desaturases with at least 65% homology with one of the fatty acid desaturases described by SEQ ID NO: 2, 4, 6, 8, 10, 12, 14 or 22.

In a preferred embodiment, the process is employed for producing conjugated linoleic acid as the unsaturated fatty acid.

Furthermore in accordance with the invention are triglycerides prepared by the process according to the invention, and their use for preparing foodstuffs, feedstuffs, cosmetics or fine chemicals.

In a number of organisms, among others in plants, the fatty acids are present in the cytosole predominantly in the form of CoA esters. In yeasts and animals, the desaturation of acyl-CoA fatty acids is the main synthetic pathway for unsaturated fatty acids, while this mechanism is fairly rare in plants (Cahoon E B et al. (2000) Plant Physiol. 124: 243-251). Surprisingly, it has been demonstrated that the recombinant expression of desaturases from lepidopterans leads to desaturation of the saturated and unsaturated fatty acid CoA esters. The final result is that both active CLA isomers are produced and incorporated into the storage lipids.

The advantage of the process according to the invention is, in particular, the possibility of the direct production of CLA-containing triglycerides, starting from organisms, preferably plants, yeasts, fungi or algae, with a high oil content, such as, for example, oilseed-rape or sunflower. The use of eukaryotic enzymes from insects of the order Lepidoptera makes possible good expression without the toxic effects frequently linked to prokaryotic proteins.

"Fatty acid desaturases" refers to enzymes which are capable of introducing a double bond into fatty acids or their derivatives, such as, for example, preferably fatty acid CoA esters. If appropriate, cofactors such as NADPH, NADH or else oxygen may additionally be necessary for this purpose. Preferred in this context are those desaturases which are capable of utilizing those acyl-CoA fatty acids as substrate whose fatty acid has a chain length of 14, 16, 18 or 20 C atoms, preferably 18 C atoms.

Preferably, the term fatty acid desaturases encompasses those enzymes which are capable of generating a double bond at position C8, C9, C10, C11 or C12 in fatty acids or their derivatives, such as, for example, preferably fatty acid CoA esters. Also preferred are those desaturases which lead to specific structural isomers, that is to say specifically to cis or trans double bonds. Specifically in this context is understood as meaning that the structural isomer in question is formed in an amount of at least 60%, preferably at least 80%, very especially preferably at least 90%, most preferably at least 95%. Very especially preferred are desaturases which generate, in fatty acids or their derivatives, such as, for example, preferably fatty acid CoA esters, a double bond as is found in a CLA isomer.

"Preferred essential characteristic" of a fatty acid desaturase from lepidopterans refers to enzymes with at least one of the following characteristics:

i) Specific generation of a cis double bond in position C8, C9, C10, C11 or C12 or a trans double bond in position C8, C9, C10, C11 or C12.

ii) Substrate specificity for fatty acids, fatty acid CoA esters and other fatty acid derivatives with a fatty acid chain length of 16 and/or 18 C atoms. In this context, substrate specificity refers to the characteristic of a fatty acid desaturase, of converting substrates of the stated chain length more rapidly than substrates of a different chain length. In this context, the conversion rate of the preferred substrate is increased by at least 50%, preferably by at least 100%, very especially preferably by at least 200%, most preferably by at least 500% in comparison with the substrates which are not preferred.

Preferred is at least in each case one of characteristics i) and ii).

The term fatty acid desaturases encompasses enzymes which are capable of introducing an isolated double bond, but also conjugases which, starting from one double bond in a substrate, are capable of generating a conjugated double bond system. In this context, it is preferably the first double bond which is moved.

Examples of preferred conjugases are those which
a) convert a Z11 double bond into two E10 and Z12 double bonds ("Z11-(E10,Z12)-conjugase"),
b) convert an E11 double bond into two E10 and Z12 double bonds ("E11-(E10,Z12)-conjugase"),
c) convert a Z10 double bond into two E10 and Z12 double bonds ("Z10-(E10,Z12)-conjugase").

In short, these enzymes can be referred to as (E10,Z12)-conjugases. These enzymes can also be referred to as E10-desaturases. The essential characteristic of the very especially preferred E10-desaturates is the introduction of a trans double bond at position C-10 of a fatty acid or of a fatty acid CoA ester, where the fatty acid has a chain length of 18 C atoms.

Furthermore preferred conjugases are those which
d) convert a Z10 double bond into two Z9 and E11 double bonds ("Z10-(Z9,E11)-conjugase"),
e) convert an E10 double bond into two Z9 and E11 double bonds ("E10-(Z9,E11)-conjugase")
f) convert a Z11 double bond into two Z9 and E11 double bonds ("Z11-(Z9,E11)-conjugase").

In short, these enzymes can be referred to as (Z9,E11)-conjugases. These enzymes can also be referred to as E11-desaturases. The essential characteristic of the very especially preferred E11-desaturases is the introduction of a trans double bond at position C11 of a fatty acid or of a fatty acid CoA ester, where the fatty acid has a chain length of 18 C atoms.

Most preferred are E10-, E11-, Z10- and Z11-desaturases, and Z11-(E10,Z12)-conjugase, E11-(E10,Z12)-conjugase, Z10-(Z9,E11)-conjugase and E10-(Z9,E11)-conjugase with a substrate specificity for fatty acids or fatty acid derivative such as fatty acid CoA esters with a fatty acid chain length of 18 C atoms.

The fatty acid desaturases preferably originate from a Lepidoptera family selected from the group consisting of Acrolepiidae, Agaristidae, Arctiidae, Bombycidae, Carposinidae, Cochylidae, Cossidae, Eriocraniidae, Gelechiidae, Geometridae, Gracillariidae, Hepialidae, Ithomiidae, Lasiocampidae, Lycaenidae, Lymantriidae, Lyonetiidae, Nepticulidae, Noctuidae, Notodontidae, Nymphalidae, Oecophoridae, Papilionidae, Pieridae, Psychidae, Pterophoridae, Pyralidae, Saturniidae, Sesiidae, Sphingidae, Tortricidae, Yponomeutidae and Zygaenidae. Particularly preferred are fatty acid desaturases from a Lepidoptera family selected from the group consisting of Tortricidae, Pyralidae, Papilionidae, Noctuidae and Geometridae.

E11-desaturases, or nucleic acid sequences encoding them, are preferably isolated from organisms of the species *Diaphania hyalinata, Diaphania nitidalis, Leucinodes orbonalis, Ostrinia nubilalis, Sesamia grisescens, Brachmia macroscopa, Paraargyresthia japonica, Mnesictena flavidalis, Telorta edentata, Epiplema moza, Argyresthia chamaecypariae, Bradina* sp., *Dichrocrocis punctiferalis, Cryptoblabes gnidiella, Palpita unionalis, Sceliodes cordalis, Anisodes* sp., *Caloptilia theivora, Phyllonorycter ringoniella, Deilephila elpenor, Manduca sexta, Scirpophaga excerpalis, Scirpophaga nivella, Andraca bipunctata, Pectinophora gossypiella* or *Diatraea saccharalis*. The E11-desaturases, or the nucleic acid sequences encoding them, are especially preferably isolated from the pheromone glands of the above insects. An example which may be mentioned is the E11-desaturase from the pheromone glands of the light brown apple moth (*Epiphyas postvittana*) (SEQ ID NO: 2), from *Ostrinia nubilalis* (SEQ ID NO:4) and from *Ostrinia furnicalis* (SEQ ID NO: 6). Especially preferred is the E11-desaturase from *Pectinophora gossypiella* as shown in SEQ ID NO: 22. The E11-desaturases from the abovementioned organisms accept the plant acyl-CoA fatty acid derivatives as substrate.

The use of these desaturases, or variants thereof, is particularly advantageous in as far as it makes possible an E11 double bond. Said desaturases are preferably optimized with a view to being able preferably to convert C16 and/or C18 acyl-CoA substrates, if they are not already capable of doing so (such as, for example, the desaturase from *Pectinophora gossypiella* as shown in SEQ ID NO: 22). A further subject matter of the invention therefore relates to polypeptides with E11-desaturase activity, the polypeptide preferentially converting C16 and/or C18 acyl-CoA fatty acids and encompassing at least one sequence selected from the group consisting of a) amino acid sequences as shown in SEQ ID NO: 2, 4, 6 and 22, and b) amino acid sequences with at least 65% homology with one of the amino acid sequences as shown in SEQ ID NO: 2, 4, 6 or 22, and c) amino acid sequences which encompass a fragment of at least 20 contiguous amino acid residues of a sequence as shown in SEQ ID NO: 2, 4, 6 or 22.

The polypeptide is especially preferably described by an amino acid sequence as shown in SEQ ID NO: 22. A further subject matter of the invention relates to nucleic acid molecules which encode said desaturases. The sequence is especially preferably as shown in SEQ ID NO: 21.

E10-desaturases, or the nucleic acid sequences encoding them, are preferably isolated from organisms of the species *Dichrocrocis chlorophanta, Dichrocrocis punctiferalis, Bombyx mandarina, Bombyx mori, Coloradia velda, Hemileuca eglanterina, Hemileuca electra electra, Hemileuca electra mojavensis, Hemileuca nuttalli* or *Notarcha derogata*. The E10-desaturases, or the nucleic acid sequences encoding them, are especially preferably isolated from the pheromone glands of the abovementioned insects.

E9-desaturases, or the nucleic acid sequences encoding them, are preferably isolated from organisms of the species *Epiplema plaqifera, Phyllonorycter coryli, Phyllonorycter harrisella, Phyllonorycter sylvella, Gelechiinae, Bryotropha* sp., *Bryotropha terrella, Gelechia betulae, Adoxophyes orana, Exartema appendiceum, Zeiraphera canadensis, Loxostege neobliteralis, Ostrinia nubilalis, Dioryctria clarioralis, Dioryctria merkeli, Dioryctria resinosella, Spodoptera exigua, Spodoptera triturata oder Polia grandis*. The E9-desaturases, or the nucleic acid sequences encoding them, are especially preferably isolated from the pheromone glands of the abovementioned insects.

E8-desaturases, or the nucleic acid sequences encoding them, are preferably isolated from organisms of the species *Phyllonorycter saportella, Phyllonorycter* sp. or *Dichrocrocis punctiferalis*. The E8-desaturases, or the nucleic acid sequences encoding them, are especially preferably isolated from the pheromone glands of the abovementioned insects.

Z11-desaturases as can be employed advantageously for producing Z11-octadecenoic acid have been described for *Bombyx mori* (Ando et al. (1988) Agric Biol. Chem. 52:473-478), *Trichoplusia ni* and *Helicoverpa zea* (Knipple et al. (1998) Proc Nat Acad Sci USA 95:15287-15292). Further Z11-desaturases, or the nucleic acid sequences encoding them, can preferably be isolated from *Manduca sexta, Diatraea grandiosella, Earias insulana, Earias vittella, Plutella xylostella, Bombyx mori* or *Diaphania nitidalis*. Examples which may be mentioned are the desaturases from *Helicoverpa zea* (SEQ ID NO: 8), *Trichoplusia ni* (SEQ ID NO: 10) and *Argyrotaenia velutinana* (SEQ ID NO: 12). Z11-desaturases, or the nucleic acid sequences encoding them, are especially preferably isolated from pheromone glands of the abovementioned insects.

Z10-desaturases, or the nucleic acid sequences encoding them, are preferably isolated from organisms of the species *Ctenopseustis filicis, Pseudexentera spoliana, Hemileuca eglanterina, Hemileuca electra electra, Hemileuca electra mojavensis, Hemileuca nuttalli, Eurhodope advenella, Mamestra configurata* or *Dichrocrocis punctiferalis*, especially preferably from the pheromone glands of the abovementioned insects. An example which may be mentioned is the desaturase from *Planototrix octo* (SEQ ID NO: 14).

(E10,Z12)-conjugases, or the nucleic acid sequences encoding them, are preferably isolated from *Bombyx mori, Phyllonorycter crataegella, Amorbia cuneana, Notocelia incarnatana, Notocelia uddmanniana, Bombyx mandarina, Coloradia velda, Hemileuca eglanterina, Hemileuca electra electra, Hemileuca electra mojavensis, Hemileuca nuttalli, Notarcha derogata, Rondotia menciana, Amphion floridensis, Hyles gallii, Hyloicus pinastri, Manduca sexta, Sphinx drupiferarum, Earias insulana, Nola confusalis* or *Notarcha basipunctalis*. (E10,Z12)-conjugases or the nucleic acid sequences encoding them, are especially preferably isolated from the pheromone glands of the abovementioned insects.

(Z9,E11)-conjugases, or the nucleic acid sequences encoding them, are preferably isolated from *Diatraea saccharalis, Xyrosaris lichneuta, Dioryctria abietella, Stenoma cecropia, Phalonidia manniana, Pselnophorus vilis, Dioryctria abietella; Dioryctria rubella, Myelopsis tetricella, Jodis lactearia, Scopula personata, Spodoptera descoinsi, Spodoptera eridania, Spodoptera latifascia, Spodoptera littoralis* or *Spodoptera litura*. (Z9,E11)-conjugases, or the nucleic acid sequences encoding them, are especially preferably isolated from the pheromone glands of the abovementioned insects.

Both the Z11-desaturases and the Z11-conjugases accept the plant acyl-CoA fatty acid derivatives as substrate, and the combined expression of these two classes of desaturases from lepidopterans in plants leads to the production of (10E,12Z)-CLA, which is incorporated into the storage lipids.

There are several possible combinations of the conjugases or desaturases with each other or with plant enzymes in order to produce the desired CLA isomers, in particular (9Z11E)-CLA and (10E,12Z)-CLA. The processes which follow are to be understood by way of example, but not by limitation:

1) Starting from stearic acid via trans-desaturation of position C11—for example by an E11-desaturase—trans-vaccenic acid can be produced (scheme 3).

Trans-vaccenic acid can then be converted by a D9-desaturase to give the (9Z,11E)-CLA isomer. It has been demonstrated for mammals and humans that trans-vaccenic Scheme 3: Biosynthetic pathways for the production of (9Z,11E)-CLA and (10E,12Z)-CLA starting from stearic acid

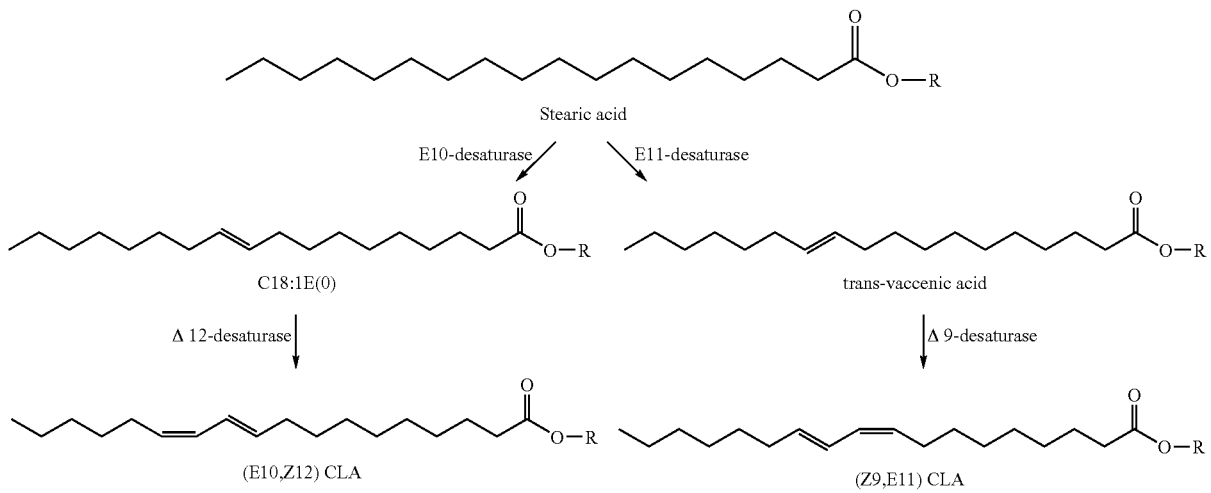

Starting from palmitic acid, palmitelaidic acid (9E-hexadecenoic acid) is produced via trans-desaturation at position C9, for example by an E9-desaturase. Palmitelaidic acid can subsequently be elongated via the enzymatic activity of an elongase to give trans-vaccenic acid (scheme 4).

acid is converted into CLA by the enzymatic activity of an endogenous D9-desaturase (WO 99/20123; Santora J E et al. (2000) J Nutr 130:208-215; Adlof R O et al. (2000) Lipids 35: 131-135). Likewise, it has been demonstrated that insect cells which express a E11-desaturase are capable of converting the resulting E11-fatty Scheme 4: Biosynthetic pathways for the production of (9Z,11E)-CLA and (10E,12Z)-CLA starting from palmitic acid

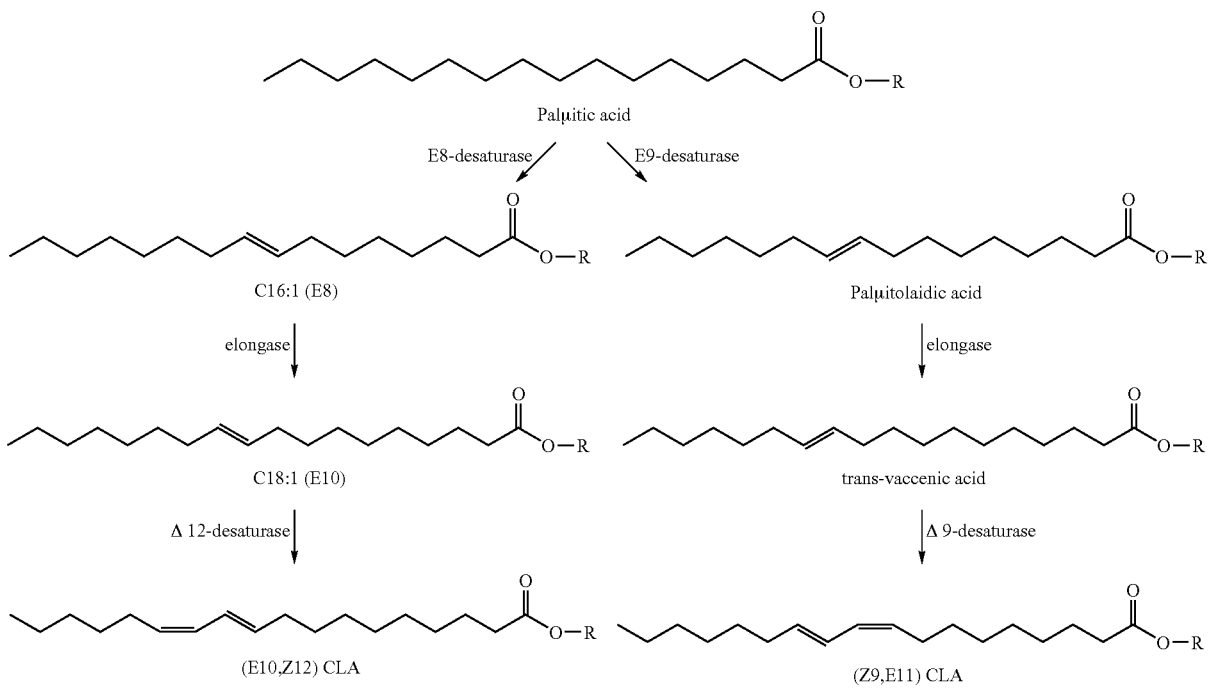

acid starting material into a Z9,E11-fatty acid (Liu W T et al. (2002) Proc Natl Acad Sci USA 99(2):620-624. Likewise, plant D9-desaturases are capable of catalyzing the conversion of trans-vaccenic acid into the (Z9,E11)-CLA isomer. In an especially preferred embodiment, this conversion can be further increased by additional expression of a Z9-desaturase. Preferred in this context are cytosolically active Z9-desaturases, such as, for example, the yeast Z9-desaturase. Thus, the production of the (Z9,E11)-CLA isomer in plants is possible by expressing a trans-desaturase. The particularly advantageous (9Z,11E)-CLA isomer is formed as a result of the effect of plant Z9-desaturases.

2) Starting from stearic acid, the corresponding E10-octadecenoic acid is initially formed by trans-desaturation at position C10 (scheme 3). As an alternative, E8-hexadecenoic acid can be produced starting from palmitic acid via trans-desaturation at position C8. The E8-hexadecenoic acid can subsequently be illustrated via the enzymatic activity of an elongase to give E10-octadecenoic acid (scheme 4). This fatty acid will be converted by the activity of a D12-desaturase to give the (E10,Z12)-CLA isomer. This reaction is also catalyzed by plant D12-desaturases. In a particularly preferred embodiment, this conversion rate can be increased further by additional expression of a Z12-desaturase.

3) Corresponding (E10,Z12)-conjugases from lepidopterans may also be employed. These conjugases convert for example Z11-octadecenoic acid (cis-vaccenic acid), E11-octadecenoic acid (trans-vaccenic acid) or Z10-otadecenoic acid into (E10,Z12)-CLA. To this end, stearic acid is first converted into Z11-octadecenoic acid, as a result of the effect of a Z11-desaturase, into trans-vaccenic acid as described above or into Z10-octadecenoic acid by a Z10-desaturase.

4) (Z9,E11)-conjugases from lepidopterans can furthermore also be combined advantageously with (Z11)-, (Z10)- or (E10)-desaturases. Starting from stearic acid, these desaturases produce Z11-octadecenoic acid (cis-vaccenic acid), Z10-octadecenoic acid or E10-octadecenoic acid, which are subsequently converted by a (Z9/E11)-conjugase to give (Z9,E11)-CLA.

The CLA fatty acids thus prepared, or their derivatives such as CoA fatty acid esters, are stored in the membrane lipids and triacyl glycerides.

The desirable enzyme activities have been localized in insects of the order lepidopterans, in particular in the above-mentioned insect species. The assay systems provided within the present invention were used for this purpose (Examples 2, 3 and 4).

The enzymes encoding these activities, or the nucleic acid sequences encoding them, can be isolated from the organisms in question in the manner with which the skilled worker is familiar or deduced by mutagenesis from corresponding known sequences.

Finding a protein sequence or a corresponding cDNA sequence to an enzymatic activity, functionality or phenotype is a traditional task in biochemistry and molecular biology. The skilled worker is familiar with a variety of processes for solving this problem. For example, these methods are based on the assays provided within the present invention for determining the desaturase or conjugase activity (see, inter alia, Example 3). The specific activity of a desaturase/conjugase in question is determined via analyzing the fatty acid pattern, for example by gas chromatography as described in Examples 2, 3 and 4. Starting from a biological material in which a desaturase or conjugase activity has been detected, using this assay make it possible to isolate the protein in question or the nucleic acid which encodes a protein with desaturase or conjugase activity and analyze it.

For example, expression cloning may be employed by way of method. This method has frequently been employed for isolating, starting from a particular enzymatic activity, a particular functionality or a particular phenotype, the gene responsible therefor or the cDNA corresponding to this gene (Dalboge H (1997) FEMS Microbiology Reviews 21(1):29-42, Simonsen H and Lodish H F (1994) Trends Pharmacol Sci 15(12):437-441). The traditional method of expression cloning has been described on a number of occasions, for example for membrane proteins, secreted factors and transmembrane channels (Masu Y et al. (1987) Nature 329(6142):836-838; Wong G G et al. (1985) Science 228(4701):810-815; Lustig K D et al. (1996) Development 122(12): 4001-4012; Smith W C and Harland R M (1992) Cell 70(5):829-840; Lemaire P et al. (1995) Cell 81(1):85-94; Gillissen B et al. (2000) Plant Cell 12(2):291-300; Lotan T and Hirschberg J (1995) FEBS Letters 364:125-128).

In the generalized method known as expression cloning, which is described hereinbelow, customary recombination and cloning techniques; as are described, for example, in Maniatis T, Fritsch E F and Sambrook J, Molecular Cloning: A Laboratory Manual, Cold Spring Harbor Laboratory, Cold Spring Harbor, N.Y. (1989) and in Silhavy T J, Berman M L and Enquist L W, Experiments with Gene Fusions, Cold Spring Harbor Laboratory, Cold Spring Harbor, N.Y. (1984) and in Ausubel F M et al. (1987) Current Protocols in Molecular Biology, Greene Publishing Assoc. and Wiley Interscience, are used.

In general, an expression library can be generated starting from an organism, from cells or tissue which are capable of generating a desaturase or conjugase activity. For example, mRNA or, preferably, poly(A)-mRNA is first isolated from said organism, cell or tissue in a manner with which the skilled worker is familiar, and cDNA is prepared on the basis of what has been isolated (Gubler U, Hoffman B J (1983) Gene 25:263-269). The skilled worker is familiar with a variety of systems for isolating mRNA or poly(A)-mRNA and they are commercially available. For example, the synthesis can be carried out using the "Quick Prep Micro mRNA Purification Kit" (Amersham Pharmacia Biotech). The first-strand cDNA synthesis is preferably carried out with an oligo (dT) primer using a reverse transcriptase (Borson N D et al. (1992) PCR Methods Appl 2:144-148; Chenchik A et al. (1994) CLONTECHniques 9(1):9-12). A variety of systems which make possible the generation of full-length cDNAs are known and commercially available. An example which may be mentioned is the "SMART™ cDNA Library Construction Kit" (Clontech, Cat.#K1051-1). In this kit, the SMART™ technology (SMART=Switch Mechanism At the 5' end of RNA Templates) is Used for generating cDNA libraries (Herrler M (2000) J Mol Med 78(7):B23). Specific oligonucleotides and the method which is known as long-distance PCR are employed. The method is described in Example 4.

Adaptors with single-stranded overhangs can be ligated to the double-stranded cDNAs; these adaptors make possible cloning for example in an expression vector which has been cleaved with restriction enzymes and has compatible cohesive ends. Preferably, cloning is directed so that the direction of reading is fixed and any promoter which may be present generates sense RNA starting from the cDNA insertion. In the SMART™ system which is used by way of example, compatible SfiI (A) and SfiI (B) overhangs are used for directed cloning into an SfiI (recognition sequence GGC-CNNNN!NGGCC)-cleaved vector. In each case one cDNA molecule is cloned into a vector molecule, so that eventually a multiplicity of vectors which are based on the same basic vector and which differ with regard to the integrated cDNA are present and form the expression library. This expression library also contains vectors which are capable of expressing a desaturase or conjugase transgene. Suitable expression vectors are, in principle, all those which are capable of recombinantly expressing, in a transformed organism, desaturases or conjugases in active form. Examples which may be mentioned are the lambda TriplEX2 vector (after excision pTriplEX2 vector; manufacturer: Clontech) for the recombinant expression in *E. coli* or the vector pYES2 (manufacturer: Invitrogen) for the recombinant expression in the yeast *S. cerevisiae* (see Example 4).

If appropriate, a normalization can be carried out in order to compensate for differences in the expression level of individual genes, so that the cDNA to each gene which is expressed is represented in the expression library with a similar copy number, independently of the actual expression level. A variety of systems have been described for the generation of poly(A)-mRNA, cDNA and standardized cDNA (U.S. Pat. No. 5,482,845) (Soares M B et al. (1994) Proc Natl Acad Sci USA 91:9228-9232; Carninci P et al. (2000) Genome Res 10:1617-1630; Bonaldo M F et al. (1996) Genome Res 6:791-806).

However, a subtractive expression library may also be established. In this method, the cDNAs of an organism, of cells or of tissue with a desaturase or conjugase are compared with the cDNAs of an organism, of cells or of tissue without this activity, if possible of the same genus and species. The skilled worker is familiar with methods for the targeted isolation of cDNAs which are only expressed in the biological material with desaturase or conjugase activity. Such methods and systems are described and commercially available. An example which may be mentioned is the "PCR-Select™ cDNA Subtraction Kit" (manufacturer: Clontech) or "Subtractor™ Kit" (manufacturer: Invitrogen), which allows an over 1000-fold concentration of rare and/or selectively expressed cDNAs. Using subtractive hybridization, all those cDNAs which are present in both biological materials are removed (Chu Z L et al. (1997) Proc Nat Acad Sci USA 94:10057-10062; Hudson C et al. (1997) Cell 91:397-405; Mueller C G F et al. (1997) J Exp Med 186:655-663; von Stein O D et al. (1997) Nucleic Acids Res 25:2598-2602; Wong B R et al. (1997) J Biol Chem 272:25190-25194; Yokomizo T et al. (1997) Nature 387:620-624; Zhicheng S and Jacobs-Lorena M (1997) J Biol Chem 272:28895-28900).

The cDNAs in the expression library can be expressed recombinantly for example in prokaryotic or eukaryotic cells which are subsequently subjected to an assay for the desaturase or conjugase protein, for example an assay for a desaturase or conjugase activity.

To isolate, from the expression library, the vectors which recombinantly express desaturase or conjugase, the expression library is preferably transformed into an organism. Preferably, individual cells of the said organism are transformed in such a way that each cell, or each organism which is regenerated starting from this cell, is transformed with one type of vector molecule only. In principle, all those organisms, or cells derived from them, which are capable of recombinantly expressing an active desaturase or conjugase are suitable for transformation. These organisms may be prokaryotic and eukaryotic. Preferred are all plants, cells derived from them, but also other photosynthetic organisms such as, for example, algae. Examples which may be mentioned, but not by way of limitation, are systems which are based on recombinant expression in bacteria such as *E. coli*, yeasts such as *Saccharomyces* or *Pichia*, mammalian cells such as COS or CHO, or cells of photosynthetically active organisms such as *Synechocystis*. Preferred organisms are eukaryotic organisms, very especially preferably eukaryotic organisms which are capable of synthesizing fatty acids or acyl-CoA fatty acids. Preferably, the expression vectors used for the transformation contain a selection marker, for example a resistance antibiotic or an amino acid synthesis gene for selection for amino acid deficiency, which makes possible the selection of successfully transformed cells. Further selection methods are described hereinbelow.

In a preferred embodiment, expression cloning can be carried out in yeast. To this end, it is possible, for example, to use the yeast expression system from Invitrogen which is based on the vector pYES2. pYES2 is a high-copy episomal vector for inducible expression of recombinant proteins in *S. cerevisiae*. Transformed-yeast strains are selected on the basis of uracil deficiency (pYES2 contains the ura3 gene).

Further preferred expression vectors and transfection methods for generating the transformed organisms are in accordance with the methods generally used for generating transgenic organisms.

Starting from the total number of the transformed organisms or cells derived from them, those which are capable of recombinantly expressing a desaturase or conjugase and/or which have a corresponding desaturase or conjugase activity are concentrated and isolated.

In general, the desaturase activity can be detected by culturing a transformed organism or cells derived therefrom, digesting it/them in a suitable buffer or solvent, bringing the digest into contact with fatty acids or acyl-CoA fatty acids and, if appropriate, with a cofactor such as NADH or NADPH or oxygen, and detecting the resulting desaturated fatty acids or acyl-CoA fatty acids. The fatty acids or acyl-CoA fatty acids can preferably originate from the transformed organism itself if the organism or the cell derived from it is itself capable of synthesizing fatty acids or acyl-CoA fatty acids. If not, however, it is also possible to add fatty acids or acyl-CoA fatty acids.

The fatty acid or acyl-CoA fatty acid which has been modified by the desaturase or conjugase can be detected via customary methods with which the skilled work is familiar, if appropriate after extraction from the incubation mixture, for example with a solvent such as ethyl acetate. Separation methods such as high-performance liquid chromatography (HPLC), gas chromatography (GC), thin-layer chromatography (TLC) and detection methods such as mass spectroscopy (MS or MALDI), UV spectroscopy or autoradiography may be employed for this purpose. Preferably, the detection is carried out using gas chromatography as described in Examples 3, 4 and 5.

The transformed organisms, or cells derived from them, which are capable of recombinantly expressing a desaturase or conjugase can be isolated for example by dividing the total number of cells into subgroups, culturing these subgroups, if appropriate separately, and measuring the desaturase or conjugase activity of the individual subgroups. The subgroup which contains a cell type which recombinantly expresses a desaturase or conjugase protein in functionally active form has an increased desaturase or conjugase activity. This subgroup is subdivided further and the procedure is repeated until the result is a monoclonal culture, i.e. a culture which contains only one vector with a specific cDNA which encodes a desaturase or conjugase.

The vector which contains the nucleic acid encoding the desaturase or conjugase can be recovered from the transformed organism or cell. This can be done for example by means of polymerase chain reaction (PCR). To this end, oligonucleotide primers which are complementary to vector sequences which flank the desaturase or conjugase cDNA insert are used. A knowledge of the desaturase or conjugase nucleic acid sequence is not required in this context. As an alternative, the vector, if not integrated into the host genome, can be recovered from the cells, transformed into *E. coli*, propagated and sequenced in order to obtain the nucleic acid sequence encoding the desaturase or conjugase. According to the above-described method, the desaturase or conjugase nucleic acid sequence can also be isolated from the isolated vector by means of PCR, without knowing its sequence order. In addition, linkers, which make possible directed cloning, may be added to the amplicon after the PCR reactions. However, cloning can also be effected by means of blunt-end ligation or T-overhang ligation in a manner with which the skilled worker is familiar. The desaturase or conjugase cDNA which has been amplified selectively by means of PCR may thus also be cloned directly into a vector suitable for generating a transgenic organism which expresses a desaturase or conjugase, without previous sequence elucidation. This cloning procedure can be effected for example as a blunt-end cloning procedure using techniques with which the skilled worker is familiar. Customary recombination and cloning techniques as cited above are used for this purpose.

The above-described method of expression cloning can especially preferably be carried out in the yeast *Saccharomyces cerevisiae*. To this end, it is also possible to use systems in which the cDNAs to be expressed recombinantly are integrated, by means of homologous recombination, into an integration platform which has been generated (Lagarde D et al. (2000) Applied and Environmental Microbiology 66(1): 64-72).

As an alternative, the method of expression cloning can also be carried out in vitro using a non-amplified expression library as described above. Suitable systems are described and commercially available. Examples which may be mentioned are the "TNT™ Coupled Reticulocyte Lysate System" (Promega; Promega Notes Number 67, 1998, p. 02). Kirschner et al. have developed an in vitro approach (IVEC="in vitro expression cloning") which does not require live cells (U.S. Pat. No. 5,654,150; King R W et al. (1997) Science 277, 973). The system has been applied successfully in particular to enzymes and kinases. Kirschner et al. have identified kinase substrates and proteases (Lustig K D et al. (1997) Meth Enzymol 283:83; Stukenberg P T et al. (1997) Curr Biol 7:338; Kothakota S et al. (1997) Science 278:294). In "in vitro expression cloning" (IVEC), small fractions of the expression library are employed. These fractions of in each case approx. 50 to 100 cDNA clones are present in plasmids and are translated into their corresponding proteins by means of a coupled in vitro transcription/translation system based on reticulocyte lysate. To this end, an oligo(dT)-primed cDNA library is constructed as described above and cloned into a high-copy expression plasmid with a T3, T7 or SP6 promoter. This plasmid library is then transformed into *E. coli*. In each case approximately 50 to 100 independent transformants are cultured on an agar plate with the corresponding selection antibiotic to a colony size of approx. 1 mm, collected and pooled. Plasmid DNA is isolated from part of this bacterial pool. This plasmid DNA, which is used as template, is transcribed directly in a reticulocyte system and translated. Details of the procedure can be found for example in the manufacturer's handbook (TNT™ Coupled Reticulocyte Lysate Systems Technical Bulletin #TB126, Promega Corporation)". Depending on the number of full-length cDNA clones in the library, approx. 30 to 50 proteins are synthesized per individual mixture. The proteins which have been produced are assayed for their desaturase or conjugase activity. Individual mixtures with an increased desaturase or conjugase activity are subdivided further. Subdivision of the individual mixtures leads to a cDNA encoding a desaturase or conjugase. The nucleic acid encoding the desaturase or conjugase can be amplified by PCR from the vectors present in this preparation and—if appropriate without knowledge and analysis of the sequence—used as described above for generating an organism which recombinantly expresses a desaturase or conjugase.

As an alternative to the rabbit reticulocyte extract, wheatgerm extract may also be used for the combined transcription/translation procedure (for example using the TNT™ Wheat Germ Extract System from Clontech).

In a further advantageous application, the cDNAs can be cloned into a retroviral vector. This permits a highly efficient transformation of the cells. Retroviral expression vectors and expression systems are described (Kitamura T, International Journal of Hematology 1998, 67:351-359) and commercially available (for example from Clontech; New Retroviral & ClonCapture Expression Libraries; CLONTECHniques October 1998, XIII (4):22-23). Transfection is initially performed in a packaging cell line (for example EcoPack™-293 or RetroPack™ PT67 Cell Line from Clontech). Using the viruses generated in this manner, the target cell line in question can be transfected and selected for the desired activity. Then, the inserts can be obtained and analyzed, for example by PCR. Furthermore, they can be cloned directly into a suitable expression vector, even without previously subjecting them to sequence analysis, and this expression vector can then be used for generating an organism which recombinantly expresses desaturase or conjugase.

E10- or E11-desaturases can be obtained by modifying known cis-desaturases via mutagenesis in such a way that they are specific for desaturation in the trans-position. To this end, for example the following nucleic acid sequences encoding cis-desaturases can act as starting sequences and be subjected to mutagenesis:

i) a nucleic acid sequence encoding a Z11-desaturase from *Helicoverpa zea* with the SEQ ID NO: 7, ii) a nucleic acid sequence encoding a Z11-desaturase from *Trichoplusia ni* with the SEQ ID NO: 9, iii) a nucleic acid sequence encoding a Z11-desaturase from *Argyrotaenia velutinana* with the SEQ ID NO: 11 or iv) a nucleic acid sequence encoding a Z10-desaturase from *Planotortrix octo* with the SEQ ID NO: 13.

Also, E11-desaturases can be modified by mutagenesis in such a way that longer-chain fatty acids can be converted more efficiently, or at all. The following are examples of starting sequences which can be used:

a) a nucleic acid sequence encoding an E11-desaturase from *Epiphyas postvittana* with the SEQ ID NO: 1, b) a nucleic acid sequence encoding an E11-desaturase from *Ostrinia nubilalis* with the SEQ ID NO: 3, or c) a nucleic acid sequence encoding an E11-desaturase from *Ostrinia furnacalis* with the SEQ ID NO: 5.

It is also conceivable to modify, by means of mutagenesis, the specificity for the position at which the double bond is introduced by abovementioned desaturases.

Methods for modifying the characteristics such as substrate specificity of desaturases by means of mutagenesis are known (Cahoon et al. (1997) Proc Nat Acad Sci USA 94:4872-4877; WO 98/06735). Further suitable methods described for other enzymes of the lipid metabolism, such as, for example, lipoxygenases, and can be used analogously (Hornung et al. (2000) Biochem Soc Trans 28:825-826; Schwarz et al. (2001) J Biol Chem 276:773-779).

Nucleic acid sequences encoding desaturases/conjugases for use in the method according to the invention can also be isolated by means of polymerase chain reaction using suitable degenerate oligonucleotide primers from cDNA preparations or libraries of the respective abovementioned Lepidoptera species. Those which are preferably employed are the oligonucleotide primer pair which is described by SEQ ID NO: 15 and 16 or the oligonucleotide primer pair which is described by SEQ ID NO: 17 and 18.

The nucleic acid sequence of the fatty acid desaturase from lepidopterans which is employed in the process according to the invention preferably comprises a) a sequence motif described by SEQ ID NO: 15 or 17 in its sense strand or b) a sequence motif described by SEQ ID NO: 16 or 18 in its antisense strand.

In a further preferred embodiment, the protein sequence of the fatty acid desaturase from lepidopterans which is used in the process according to the invention, preferably has at least 65%, preferably at least 70%, especially preferably at least 80%, very especially preferably at least 90%, homology with one of the fatty acid desaturases described by SEQ ID NO: 2, 4, 6, 8, 10, 12 or 14 and—optionally and preferably—has at least one of the preferred essential characteristics of a desaturase or conjugase.

These proteins can also encompass natural or artificial mutations of one of the abovementioned desaturase nucleic acid sequences and their homologs from other animal or plant genera and species. Mutations encompass substitutions, additions, deletions, inversions or insertions of one or more nucleotide residues. Where insertions, deletions or substitutions, such as, for example, transitions and transversions, are suitable, techniques which are known per se, such as in vitro mutagenesis, primer repair, restriction or ligation can be used. Complementary ends of the fragments can be provided for ligation by manipulations such as, for example restriction, chewing-back or filling up overhangs for blunt ends. Analogous results can also be obtained using the polymerase chain reaction (PCR) using specific oligonucleotide primers.

In a further preferred embodiment, the nucleic acid sequence encoding the fatty acid desaturase from lepidoterans which is employed in the process according to the invention preferably has at least 65%, preferably at least 70%, especially preferably at least 80%, very especially preferably at least 90% homology with one of the nucleic acid sequences described by SEQ ID NO: 1, 3, 5, 7, 9, 11 or 13 and which—optionally and preferably—encodes a protein which has at least one of the preferred essential characteristics of a desaturase or conjugase.

Homology between two nucleic acids or polypeptides is understood as meaning the identity of the nucleic acid sequence over in each case the entire sequence length, which is calculated by alignment with the aid of the program algorithm GAP (Wisconsin Package Version 10.0, University of Wisconsin, Genetics Computer Group (GCG), Madison, USA), setting the following parameters:

| | |
|---|---|
| Gap Weight: 12 | Length Weight: 4 |
| Average Match: 2.912 | Average Mismatch: −2.003 |

In a further preferred embodiment, the nucleic acid sequence encoding the fatty acid desaturase from lepidopterans which is employed in the method according to the invention preferably hybridizes under standard conditions with one of the abovementioned nucleic acid sequences encoding desaturases, preferably with the sequence as shown in SEQ ID NO: 1, 3, 5, 7, 9, 11 or 13.

The term standard hybridization conditions is to be understood in the broad sense and refers to stringent or else less stringent hybridization conditions. Such hybridization conditions are described, inter alia, by Sambrook J, Fritsch E F, Maniatis T et al., in Molecular Cloning (A Laboratory Manual), $2^{nd}$ edition, Cold Spring Harbor Laboratory Press, 1989, pages 9.31-9.57) or in Current Protocols in Molecular Biology, John Wiley & Sons, NY (1989), 6.3.1-6.3.6. For example, the conditions during the wash step can be selected from the range of conditions delimited by those with low stringency (approximately 2×SSC at 50° C.) and those with high stringency (approximately 0.2×SSC at 50° C., preferably at 65° C.) (20×SSC: 0.3M sodium citrate, 3M NaCl, pH 7.0). In addition, the temperature during the wash step can be raised from low-stringency conditions at room temperature, approximately 22° C., to higher-stringency conditions at approximately 65° C. The two parameters, salt concentration and temperature, can be varied simultaneously or else one of the two parameters can be kept constant while only the other one is varied. Denaturing agents such as, for example, formamide or SDS can also be employed during the hybridization reaction. In the presence of 50% formamide, the hybridization reaction is preferably carried out at 42° C. Some examples of conditions for the hybridization and wash step are detailed hereinbelow:

(1) Hybridization conditions with, for example,
 a) 4×SSC at 65° C.,
 b) 6×SSC at 45° C.,
 c) 6×SSC at 68° C., 100 μg/ml denatured fish sperm DNA,
 d) 4×SSC, 50% formamide, at 42° C.,
 e) 2× or 4×SSC at 50° C. (low-stringency condition), or
 f) 2× or 4×SSC, 30 to 40% formamide, at 42° C. (low-stringency condition).

(2) Wash steps with, for example,
 a) 0.1×SSC at 65° C., or
 b) 0.1×SSC, 0.5% SDS at 68° C., or
 c) 0.1×SSC, 0.5% SDS, 50% formamide at 42° C., or
 d) 0.2×SSC, 0.1% SDS at 42° C., or
 e) 2×SSC at 65° C. (low-stringency condition).

For the purposes of the present invention, "nucleic acid sequence" refers to, for example, a genomic or a complementary DNA (cDNA) sequence or an RNA sequence, and semisynthetic or fully synthetic analogs thereof. These sequences can exist in linear or circular form, extrachromosomally or integrated into the genome. The nucleotide sequences of the expression cassettes or nucleic acids according to the invention can be generated synthetically or obtained naturally or comprise a mixture of synthetic and natural DNA constituents, and consist of various heterologous gene segments of various organisms. Moreover, artificial nucleic acid sequences are suitable as long as they have the desired essential characteristics. For example, synthetic nucleotide sequences with codons which are preferred by plants to be transformed can be generated. These codons which are preferred by plants can be determined in the customary manner on the basis of the codon usage from codons with the highest protein frequency. Especially suitable are coding nucleotide sequences which have been obtained by backtranslation of a polypeptide sequence in accordance with the host-plant-specific codon usage. In order to circumvent undesired plant regulatory mechanisms, it is possible, for example starting from the amino acid sequence of a desaturase from Lepidoptera insects and taking into consideration the plant codon usage, to backtranslate DNA fragments and use the result for generating the complete exogenous desaturase sequence which is optimized for use in the plant.

All of the abovementioned nucleotide sequences can be synthesized chemically in the manner known per se from the nucleotide units, such as, for example, by fragment condensation of individual, overlapping complementary nucleic acid units of the double helix. Oligonucleotides can be synthesized chemically for example in a manner known per se by the phosphoamidite method (Voet, Voet, 2$^{nd}$ edition, Wiley Press New York, pages 896-897). When preparing a nucleic acid construct, various DNA fragments can be manipulated in such a way that a nucleotide sequence with the correct direction of reading and the correct reading frame is obtained. Adapters or linkers can be added to the fragments in order to link the nucleic acid fragments with each other. The addition of synthetic oligonucleotides and the filling up of gaps with the aid of the Klenow fragment of the DNA polymerase, ligation reactions and general cloning methods are described by Sambrook et al. (1989). Molecular cloning: A laboratory manual, Cold Spring Harbor Laboratory Press.

When referring to, for example, a nucleic acid sequence, an expression cassette, a vector or an organism, "transgenic"/ "recombinant" refers to all those constructions which have come about by recombinant methods, or to their use, in which either a) the nucleic acid sequence encoding a desaturase or
b) a genetic control sequence, for example a promoter, linked operably to the nucleic acid sequence encoding a desaturase, or
c) (a) and (b)

are not in their natural genetic environment or have been modified by recombinant methods, the modification for example taking the form of substitutions, additions, deletions, inversions or insertions of one or more nucleotide residues. The term natural genetic environment refers to the natural chromosomal locus in the organism of origin or to the presence in a genomic library. In the case of a genomic library, the natural genetic environment of the nucleic acid sequence is preferably retained at least in part. The environment flanks the nucleic acid sequence at least unilaterally and has a sequence length of at least 50 bp, preferably at least 500 bp, especially preferably at least 1000 bp, very especially preferably at least 5000 bp. A naturally occurring expression cassette—for example the naturally occurring combination of a desaturase-encoding gene sequence with its natural promoter—becomes a recombinant expression cassette when the latter is modified by non-natural, synthetic ("artificial") processes such as, for example, mutagenization. Such processes are described (U.S. Pat. No. 5,565,350; WO 00/15815; see also above).

Recombinant expression refers to the use of a recombinant expression cassette for expressing a nucleic acid sequence.

The invention furthermore relates to recombinant expression cassettes which comprise a desaturase-encoding nucleic acid sequence, and vectors encompassing these expression cassettes.

In said recombinant expression cassettes, a desaturase-encoding nucleic acid molecule is preferably in operable linkage with at least one genetic control element (for example a promoter) which ensures the recombinant expression (transcription and/or translation) of said desaturase in an organism, preferably in plants, plant organisms, algae, yeasts or fungi. If the recombinant expression cassette is to be introduced directly into the plant and the desaturase to be expressed in planta, plant-specific genetic control elements (for example promoters) are preferred. However, the desaturase can also be expressed in other organisms or in vitro. Here, preferred prokaryotic or eukaryotic genetic control elements (for example promoters) are all those which allow for expression in the organism chosen in each case for the production.

The invention furthermore therefore relates to recombinant expression cassettes comprising at least one nucleic acid sequence encoding a fatty acid desaturase from insects of the order Lepidoptera under the control of a promoter which is functional in plants, plant organisms, algae, yeasts or fungi. Preferably, the nucleic acid sequence which is present in the expression cassettes encodes a polypeptide which encompasses at least one sequence selected from the group consisting of a) amino acid sequences as shown in SEQ ID NO: 2, 4, 6, 8, 10, 12, 14 or 22, and
b) amino acid sequences with at least 65% homology with one of the amino acid sequences as shown in SEQ ID NO: 2, 4, 6, 8, 10, 12, 14 or 22, and
c) amino acid sequences which encompass a fragment of at least 20 contiguous amino acid sequences of a sequence as shown in SEQ ID NO: 2, 4, 6, 8, 10, 12, 14 or 22.

The fatty acid desaturase is especially preferably described in this context by an amino acid sequence as shown in SEQ ID NO: 22.

The invention furthermore relates to recombinant expression vectors which comprise at least one of the expression cassettes according to the invention and to transgenic organisms which comprise at least one of the recombinant expression cassettes according to the invention or one of the recombinant expression vectors according to the invention. Preferably, the transgenic organism is a plant organism, especially preferably selected from the plants used for oil production such as, for example, sunflower, sesame, safflower, olive tree, soya, linseed, peanut, castor-oil plant, oil palm, maize, wheat, cocoa bush and nut species.

Operable linkage is understood as meaning, for example, the sequential arrangement of a promoter with the desaturase nucleic acid sequence to be expressed and, if appropriate, further regulatory elements such as, for example, a terminator in such a way that each of the regulatory elements can fulfil its function when the nucleic acid sequence is expressed recombinantly. Direct linkage in the chemical sense is not necessarily required for this purpose. Genetic control sequences such as, for example, enhancer sequences can also exert their function on the target sequence from positions which are further removed or indeed from other DNA molecules. Preferred arrangements are those in which the nucleic acid sequence to be expressed recombinantly is positioned behind the sequence acting as promoter so that the two sequences are linked covalently to each other. The distance between the promoter sequence and the nucleic acid sequence to be expressed recombinantly is preferably less than 200 base pairs, particularly preferably less than 100 base pairs, very particularly preferably less than 50 base pairs.

Operable linkage and a transgenic expression cassette can both be produced by means of conventional recombination and cloning techniques as they are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L und Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or of a signal peptide, may also be positioned between the two sequences. Also, the insertion of sequences may lead to the expression of fusion proteins. Preferably, the recombinant expression cassette composed of a promoter linked to a nucleic acid sequence to be expressed can be in a vector-integrated form and can be inserted into a plant genome, for example by transformation.

However, a transgenic expression cassette is also understood as meaning those constructs where the nucleic acid sequence encoding a desaturase is placed behind an endogenous promoter in such a way that the latter controls the expression of the desaturase. The fusion of endogenous promoter and desaturase nucleic acid sequence, which is brought about by the insertion, is a recombinant expression cassette for the purposes of the invention.

Plant-specific promoters are understood as meaning any promoter which is capable of governing the expression of genes, in particular foreign genes, in plants or plant parts, plant cells, plant tissues or plant cultures. In this context, expression may be, for example, constitutive, inducible or development-dependent. The following are preferred:

a) Constitutive Promoters

Preferred vectors are those which make possible a constitutive expression in plants (Benfey et al. (1989) EMBO J. 8, 2195-2002). "Constitutive" promoter refers to those promoters which ensure expression in a large number of, preferably all, tissues over a substantial period of plant development, preferably at all times during plant development. A plant promoter or promoter originating from a plant virus is especially preferably used. The promoter of the CaMV (cauliflower mosaic virus) 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202) are especially preferred. Another suitable constitutive promoter is the Rubisco small subunit (SSU) promoter (U.S. Pat. No. 4,962,028), the leguminB promoter (GenBank Acc. No. X03677), the promoter of the nopalin synthase from *Agrobacterium*, the TR dual promoter, the OCS (octopine synthase) promoter from *Agrobacterium*, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), and further promoters of genes whose constitutive expression in plants is known to the skilled worker.

b) Tissue-Specific Promoters

Furthermore preferred are promoters with specificities for the anthers, ovaries, flowers, leaves, stems, roots and seeds.

Seed-Specific Promoters such as, for example, the phaseolin promoter (U.S. Pat. No. 5,504,200; Bustos M M et al. (1989) Plant Cell 1 (9):839-53), the 2S albumin gene promoter (Joseffson L G et al. (1987) J Biol Chem 262:12196-12201), the legumine promoter (Shirsat A et al. (1989) Mol Gen Genet 215(2):326-331), the USP (unknown seed protein) promoter (Bäumlein H et al. (1991) Mol Gen Genet 225(3):459-67), the napin gene promoter (U.S. Pat. No. 5,608,152; Stalberg K et al. (1996) L Planta 199:515-519), the promoter of the sucrose binding protein (WO 00/26388) or the legumin B4 promoter (LeB4; Bäumlein H et al. (1991) Mol Gen Genet 225: 121-128; Bäumlein et al. (1992) Plant Journal 2(2):233-9; Fiedler U et al. (1995) Biotechnology (NY) 13(10):1090f), the *Arabidopsis* oleosin promoter (WO 98/45461), and the *Brassica* Bce4 promoter (WO 91/13980). Further suitable seed-specific promoters are those of the gene encoding high-molecular weight glutenin (HMWG), gliadin, branching enzyme, ADP glucose pyrophosphatase (AGPase) or starch synthase. Promoters which are furthermore preferred are those which permit a seed-specific expression in monocots such as maize, barley, wheat, rye, rice and the like. The promoter of the Ipt2 or Ipt1 gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the casirin gene or the secalin gene) can advantageously be employed.

Tuber-, storage-root- or root-specific promoters such as, for example, the class I patatin promoter (B33) and the promoter of the cathepsin D inhibitor from potato.

Leaf-Specific Promoters such as the promoter of the potato cytosolic FBPase (WO 97/05900), the SSU promoter (small subunit) of Rubisco (ribulose-1,5-bisphosphate carboxylase) or the potato ST-LSI promoter (Stockhaus et al. (1989) EMBO J 8:2445-2451).

Flower-Specific Promoters such as, for example, the phytoene synthase promoter (WO 92/16635) or the promoter of the P-rr gene (WO 98/22593).

Anther-Specific Promoters such as the 5126 promoter (U.S. Pat. No. 5,689,049, U.S. Pat. No. 5,689,051), the glob-I promoter and the g-zein promoter.

c) Chemically Inducible Promoters

The recombinant expression cassettes may also contain a chemically inducible promoter (review article: Gatz et al. (1997) Annu Rev Plant Physiol Plant Mol Biol 48:89-108), by means of which the expression of the exogenous gene in the plant can be controlled at a particular point in time. Such promoters such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracyclin-inducible promoter (Gatz et al. (1992) Plant J 2:397-404), an abscisic acid-inducible promoter (EP 0 335 528) or an ethanol- or cyclohexanone-inducible promoter (WO 93/21334) can likewise be used.

d) Stress- or Pathogen-Inducible Promoters

Other promoters which are preferred are those which are induced by biotic or abiotic stress, such as, for example, the pathogen-inducible promoter of the PRP1 gene (Ward et al. (1993) Plant Mol Biol 22:361-366), the heat-inducible hsp70 or hsp80 promoter from tomato (U.S. Pat. No. 5,187,267), the low-temperature-inducible alpha-amylase promoter from potato (WO 96/12814), the light-inducible PPDK promoter or the wound-induced pinII promoter (EP375091).

Pathogen-inducible promoters encompass the promoters of genes which are induced as the consequence of a pathogen attack, such as, for example, genes of PR proteins, SAR proteins, b-1,3-glucanase, chitinase and the like (for example Redolfi et al. (1983) Neth J Plant Pathol 89:245-254; Uknes, et al. (1992) The Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968 (1989).

Also included are wound-inducible promoters such as the promoter of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of systemin (McGurl et al. (1992) Science 225:1570-1573), of the WIP1 gene (Rohmeier et al. (1993) Plant Mol Biol 22:783-792; Eckelkamp et al. (1993) FEBS Letters 323:73-76), of the MPI gene (Corderok et al. (1994) The Plant J 6(2):141-150) and the like.

e) Development-Dependent Promoters

Other suitable promoters are, for example, fruit-maturation-specific promoters, such as, for example, the fruit-maturation-specific promoter from tomato (WO 94/21794, EP 409 625). Development-dependent promoters include some of the tissue-specific promoters since some tissues are formed naturally as the function of development.

Other promoters which are suitable for expression in plants have been described (Rogers et al. (1987) Meth in Enzymol 153:253-277; Schardl et al. (1987) Gene 61:1-11; Berger et al. (1989) Proc Natl Acad Sci USA 86:8402-8406). Constitutive and seed-specific promoters are particularly preferred.

In addition, further promoters which make possible expression in further plant tissues or in other organisms such as, for example, *E. coli* bacteria, may be linked operably with the nucleic acid sequence to be expressed. Suitable plant promoters are, in principle, all of the above-described promoters.

The nucleic acid sequences present in the recombinant expression cassettes or vectors according to the invention can be linked operably with further genetic control sequences besides a promoter. The term genetic control sequences is to be understood in the broad sense and refers to all those sequences which have an effect on the establishment or the function of the expression cassette according to the invention. Genetic control sequences modify, for example, transcription and translation in prokaryotic or eukaryotic organisms. The recombinant expression cassettes according to the invention preferably encompass the promoter with specificity for the embryonal epidermis and/or the flower 5'-upstream of the nucleic acid sequence to be expressed recombinantly in each case and, as additional genetic control sequence, a terminator sequence 3'-downstream, and, if appropriate, further customary regulatory elements, in each case operably linked with the nucleic acid sequence to be expressed recombinantly.

Genetic control sequences also encompass further promoters, promoter elements or minimal promoters capable of modifying the expression-controlling properties. Thus, genetic control sequences can, for example, bring about tissue-specific expression which is additionally dependent on certain stress factors. Such elements are, for example, described for water stress, abscisic acid (Lam E and Chua N H, J Biol Chem 1991; 266(26): 17131-17135) and thermal stress (Schoffl F et al. (1989) Mol Gen Genetics 217(2-3): 246-53).

Further advantageous control sequences are, for example, in the Gram-positive promoters amy and SPO2, and in the yeast or fungal promoters ADC1, MFa, AC, P-60, CYC1, GAPDH, TEF, rp28, ADH.

In principle, all natural promoters with their regulatory sequences like those mentioned above may be used for the process according to the invention. In addition, synthetic promoters may also be used advantageously.

Genetic control sequences also further encompass the 5'-untranslated regions, introns or nonencoding 3'-region of genes, such as, for example, the actin-1 intron, or the Adh1-S introns 1, 2 and 6 (for general reference, see: The Maize Handbook, Chapter 116, Freeling and Walbot, Eds., Springer, New York (1994)). It has been demonstrated that these may play a significant role in regulating gene expression. Thus, it has been demonstrated that 5'-untranslated sequences can enhance the transient expression of heterologous genes. Translation enhancers which may be mentioned by way of example are the tobacco mosaic virus 5' leader sequence (Gallie et al. (1987) Nucl Acids Res 15:8693-8711) and the like. They may furthermore promote tissue specificity (Rouster J et al. (1998) Plant J 15:435-440).

The recombinant expression cassette can advantageously contain one or more of what are known as enhancer sequences in operable linkage with the promoter, and these make possible an increased recombinant expression of the nucleic acid sequence. Additional advantageous sequences such as further regulatory elements or terminators may also be inserted at the 3' end of the nucleic acid sequences to be expressed recombinantly. One or more copies of the nucleic acid sequences to be expressed recombinantly may be present in the gene construct.

Polyadenylation signals which are suitable as control sequences are plant polyadenylation signals, preferably those which correspond essentially to *Agrobacterium tumefaciens* T-DNA polyadenylation signals, in particular those of gene 3 of the T-DNA (octopine synthase) of the Ti plasmid pTiACHS (Gielen et al. (1984) EMBO J 3:835 et seq.) or functional equivalents thereof. Examples of particularly suitable terminator sequences are the OCS (octopine synthase) terminator and the NOS (nopaline synthase) terminator.

Control sequences are furthermore understood as those which make possible homologous recombination or insertion into the genome of a host organism, or removal from the genome. Methods such as the cre/lox technology permit the tissue-specific, possibly inducible, removal of the recombinant expression cassette from the genome of the host organism (Sauer B (1998) Methods. 14(4):381-92). Here, certain flanking sequences are added to the target gene (lox sequences), and these make possible removal by means of cre recombinase at a later point in time.

A recombinant expression cassette and the recombinant vectors derived from it may comprise further functional elements. The term functional element is to be understood in the broad sense and refers to all those elements which have an effect on the generation, replication or function of the recombinant expression cassettes, vectors or transgenic organisms according to the invention. Examples which may be mentioned, but not by way of limitation, are:

a) Selection markers which confer resistance to a metabolism inhibitor such as 2-deoxyglucose-6-phosphate (WO 98/45456), antibiotics or biocides, preferably herbicides, such as, for example, kanamycin, G 418, bleomycin, hygromycin, or phosphinothricin and the like. Particularly preferred selection markers are those which confer resistance to herbicides. The following may be mentioned by way of example: DNA sequences which encode phosphinothricin acetyltransferases (PAT) and which inactivate glutamine synthase inhibitors (bar and pat gene), 5-enolpyruvylshikimate-3-phosphate synthase genes (EPSP synthase genes), which confer resistance to Glyphosate (N-(phosphonomethyl)glycine), the gox gene, which encodes Glyphosate-degrading enzyme (Glyphosate oxidoreductase), the deh gene (encoding a dehalogenase which inactivates dalapon), sulfonylurea- and imidazolinone-inactivating acetolactate synthases, and bxn genes which encode nitrilase enzymes which degrade bromoxynil, the aasa gene, which confers resistance to the antibiotic apectinomycin, the streptomycin phosphotransferase (SPT) gene, which permits resistance to streptomycin, the neomycin phosphotransferase (NPTII) gene, which confers resistance to kanamycin or geneticidin, the hygromycin phosphotransferase (HPT) gene, which confers resistance to hygromycin, the acetolactate synthase gene (ALS), which confers resistance to sulfonylurea herbicides (for example mutated ALS variants with, for example, the S4 and/or Hra mutation).
b) Reporter genes which encode readily quantifiable proteins and which allow the transformation efficiency or the expression site or time to be assessed via their color or enzyme activity. Very particularly preferred in this context are reporter proteins (Schenborn E, Groskreutz D. Mol Biotechnol. 1999; 13(1):29-44) such as the "green fluorescent protein" (GFP) (Sheen et al. (1995) Plant Journal 8(5):777-784); Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui W L et al. (1996) Curr Biol 6:325-330; Leffel S M et al. (1997) Biotechniques. 23(5):912-8, chloramphenicol transferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268), β-galactosidase, R locus gene (encodes a protein which regulates the production of anthocyanin pigments (red coloration) in plant tissue and thus makes possible a direct analysis of the promoter activity without the addition of additional auxiliaries or chromogenic substrates; Dellaporta et al., In: Chromosome Structure and Function: Impact of New Concepts, 18$^{th}$ Stadler Genetics Symposium, 11:263-282, 1998), β-glucuronidase (Jefferson et al. (1987) EMBO J 6:3901-3907).
c) Replication origins which allow replication of the recombinant expression cassettes or vectors according to the invention in, for example, E. coli. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).
d) Elements which are required for *agrobacterium*-mediated plant transformation such as, for example, the right or left border of the T-DNA, or the vir region.

To select cells which have successfully undergone homologous recombination or else cells which have successfully been transformed, it is generally required additionally to introduce a selectable marker which confers resistance to a biocide (for example a herbicide), a metabolism inhibitor such as 2-deoxyglucose-6-phosphate (WO 98/45456) or an antibiotic to the cells which have successfully undergone recombination. The selection marker permits the selection of the transformed cells from untransformed cells (McCormick et al. (1986) Plant Cell Reports 5:81-84).

By way of example, but not by limitation, the recombinant expression cassette according to the invention can have the following structure:
a) 5'-plant-specific promoter/desaturase/terminator-3'
The recombinant expression cassette according to the invention preferably has the following structure:
a) 5'-35S promoter/desaturase/OCS terminator 3', or
b) 5'-LeguminB promoter/desaturase/NOS terminator 3'
Cotransformation with more than one of the abovementioned examples a) or b) may be advantageous for the advantageous CLA biosynthesis processes according to the invention. Furthermore transformation with one or more vectors, each of which contains a combination of the abovementioned recombinant expression cassettes, may be advantageous.

In addition, said recombinant expression cassette may comprise a nucleic acid sequence whose recombinant expression brings about an increase in fatty acid biosynthesis (hereinbelow proOIL). This proOIL nucleic acid sequence which is additionally expressed recombinantly can be selected by way of example but not by limitation from among nucleic acids encoding acetyl-CoA carboxylase (ACCase), glycerol-3-phosphate acyltransferase (GPAT), lysophosphatidate acyltransferase (LPAT), diacylglycerol acyltransferase (DAGAT) and phospholipid:diacylglycerol-acyltransferase (PDAT).

The proOIL nucleic acid sequences also encompass those nucleic acids whose recombinant expression generates an antisense-RNA or a duplex RNA which also brings about an increase in the fatty acid production.

Preferred examples encompass vectors comprising the following recombinant expression cassettes:
a) 5'-35S promoter/desaturase/OCS terminator/leguminB promoter/proOIL/NOS terminator 3';
b) 5'-35S promoter/pro-desaturase or conjugase/OCS terminator/leguminB promoter/proOIL/NOS terminator 3';
Constructs a) and b) allow the simultaneous transformation of the plant with a desaturase and a proOIL sequence which increases the fatty acid biosynthesis.

Using the above-cited recombination and cloning techniques, the desaturase or proOIL nucleic acids or recombinant expression cassettes according to the invention can be cloned into suitable vectors which allow their propagation in, for example, E. coli. Suitable cloning vectors are pBR332, pUC series, M13mp series and pACYC184, inter alia. Especially suitable are binary vectors which are capable of replication both in E. coli and in *agrobacteria*.

The desaturase or proOIL nucleic acids or recombinant expression cassettes according to the invention are preferably inserted into suitable transformation vectors. Suitable vectors are described, inter alia, in "Methods in Plant Molecular Biology and Biotechnology" (CRC Press), chapter 6/7, p. 71-119 (1993). Transformation examples and transformation processes are described hereinbelow.

The invention furthermore relates to transgenic organisms transformed with at least one recombinant expression cassette according to the invention or with a vector according to the invention, and to cells, cell cultures, tissues, parts—such as, for example, leaves, roots and the like in the case of plant organisms—or propagation material derived from such organisms.

The terms organism, starting organisms or host organisms are understood as meaning prokaryotic or eukaryotic organisms such as, for example, microorganisms or plant organisms.

Preferred microorganisms are bacteria, yeasts, algae or fungi.

Preferred bacteria are bacteria from the genus *Escherichia, Corynebacterium, Bacillus, Clostrridium, Proionibacterium, Butyrivibrio, Eubacterium, Lactobacillus, Erwinia, Agrobacterium, Flavobacterium, Alcaligenes, Phaeodactylum, Colpidium, Mortierella, Entomophthora, Mucor, Cryptheco-dinium* or cyanobacteria, for example of the genus *Synechocystis*.

Particularly preferred are microorganisms which are capable of infecting plants and thus of transferring the constructs according to the invention. Preferred microorganisms are those of the genus *Agrobacterium*, in particular of the species *Agrobacterium tumefaciens*.

Preferred yeasts are *Candida, Saccharomyces, Hansenula* or *Pichia*. Particularly preferred yeasts are those in which fatty acids/fatty acid derivatives amount to at least 20%, preferably 40%, especially preferably 60% of the cell dry matter, in particular yeasts such as *Cryptococcus curvatus* (Ratledge (1989) Biotechnology of oils and fats. In: Microbiol lipids Vol. 2 Academic Press, London, pp. 567-668).

Preferred fungi are *Aspergillus, Trichoderma, Ashbya, Neurospora, Fusarium, Beauveria, Phytophthora infestans* or further fungi described in Indian Chem Engr. Section B. Vol 37, No 1, 2 (1995), page 15, Table 6. Especially preferred are fungi in which fatty acids/fatty acid derivatives amount to at least 10%, preferably 20% of the cell dry matter, in particular *Mucor circinelloides* and *Mortierella alpina* (Wynn et al. (2001) Microbiology 147: 2857-2864).

Preferred transgenic organisms are, in particular, plant organisms. The term "plant organism" encompasses any organism which is capable of photosynthesis and cells, tissues, parts or propagation material (such as seeds or fruit) derived therefrom. Included for the purpose of the invention are all genera and species of higher and lower plants of the plant kingdom. Annual, perennial, monocotyledonous and dicotyledonous plants and gymnosperms are preferred. Included are the mature plant, seeds, shoots and seedlings, and parts derived therefrom, propagation material (for example tubers, seeds or fruit) plant organs, tissues, protoplasts, callus cultures and other cultures, for example cell cultures. "Mature plants" refers to plants at any developmental stage beyond the seedling stage. The term seedling refers to a young immature plant at an early developmental stage.

"Plant" encompasses all annual and perennial monocotyldedonous or dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hemericallis, Nemesia, Pelargonium, Panicum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*.

Preferred plants are those from the following plant families: Amaranthaceae, Asteraceae, Brassicaceae, Caryophylaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, Theaceae, Umbelliferae.

Preferred monocotyledonous plants are selected in particular from the monocotyledonous crop plants such as, for example, the Gramineae family, such as alfalfa, rice, maize, wheat or other cereal species such as barley, millet and sorghum, rye, triticale or oats, and sugar cane, and all grass species.

The invention is applied very particularly preferably to dicotyledonous plant organisms. Preferred dicotyledonous plants are selected in particular from the dicotyledonous crop plants such as, for example, Asteraceae such as sunflower, tagetes or *calendula* and others, Compositae, especially the genus *Lactuca*, very particularly the species *sativa* (lettuce) and others, Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and *cress* or *canola* and others, Cucurbitaceae such as melon, pumpkin/squash or zucchini and others, Leguminosae, particularly the genus *Glycine*, very particularly the species *max* (soybean), soya, and alfalfa, pea, bean or peanut and others, Rubiaceae, preferably the subclass Lamiidae such as, for example *Coffea arabica* or *Coffea liberica* (coffee bush) and others, Solanaceae, particularly the genus *Lycopersicon*, very particularly the species *esculentum* (tomato), the genus *Solanum*, very particularly the species *tuberosum* (potato) and *melongena* (aubergine) and tobacco or paprika and others, Sterculiaceae, preferably the subclass Dilleniidae such as, for example, *Theobroma cacao* (cacao bush) and others, Theaceae, preferably the subclass Dilleniidae such as, for example, *Camellia sinensis* or *Thea sinensis* (tea shrub) and others, Umbelliferae, particularly the genus *Daucus* (very particularly the species *carota* (carrot)) and *Apium* (very particularly the species *graveolens dulce* (celery)) and others; and the genus *Capsicum*, very particularly the genus *annum* (pepper) and others, and linseed, soya, cotton, hemp, flax, cucumber, spinach, carrot, sugar beet and the various tree, nut and grapevine species, in particular banana and kiwi fruit.

Also encompassed are ornamental plants, useful or ornamental trees, flowers, cut flowers, shrubs or turf. Plants which may be mentioned by way of example but not by limitation are angiosperms, bryophytes such as, for example, Hepaticae (liverworts) and Musci (mosses); pteridophytes such as ferns, horsetail and clubmosses; gymnosperms such as conifers, cycads, ginkgo and Gnetatae, the families of the Rosaceae such as rose, Ericaceae such as rhododendron and azalea, Euphorbiaceae such as poinsettias and *croton*, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geranium, Liliaceae such as dracena, Moraceae such as *ficus*, Araceae such as philodendron and many others.

Furthermore, plant organisms for the purposes of the invention are further organisms capable of being photosynthetically active such as, for example, algae, cyanobacteria and mosses. Preferred algae are green algae such as, for example, algae from the genus *Haematococcus, Phaedactylum tricornatum, Volvox* or *Dunaliella*. *Synechocystis* is particularly preferred.

Most preferred are plants which are suitable for oil production such as, for example, oilseed rape, sunflower, sesame, safflower (*Carthamus tinctorius*), olive tree, soya, linseed, peanut, castor-oil plant, oil palm, maize, wheat, cocoa bush or various nut species such as, for example, walnut, coconut or almond. Most preferred are furthermore *Arabidopsis*, cotton, flax and linseed.

Preferred algae are green algae such as, for example, algae of the genus *Haematococcus, Phaedactylum tricornatum, Volvox* or *Dunaliella*. Others which may be mentioned as being preferred are protozoa such as dinoflagellates.

Preferred among abovementioned organisms are, in particular, those which are naturally capable of synthesizing oils in substantial amounts, such as fungi, e.g. *Mucor circinelloides, Mortierella alpina, Pythium insidiosum*, yeasts such as *Saccharomyces cerevisiae* or *Cryptococcus curvatus*, or plants such as soya, linseed, oilseed rape, coconut, oil palm, safflower, castor-oil plant, peanut, cacao tree or sunflower, especially preferably soya, oilseed rape, sunflower, *Mucor circinelloides, Mortierella alpina, Pythium insidiosum, Cryptococcus curvatus* or *Saccharomyces cerevisiae*.

A further enumeration of a wide range of oil-accumulating organisms can be found in Kyle and Ratledge (1992) Industrial applications of Single Cell Oils, American Oil Chemists' Society, Champaign, Ill.

Depending on the host organism, the organisms used in the processes are grown or cultured in a manner known to the skilled worker. As a rule, microorganisms are grown in a liquid medium which contains a carbon source, usually in the form of sugars, a nitrogen source, usually in the form of organic nitrogen sources such as yeast extract or salts such as ammonium sulfate, trace elements such as iron salts, manganese salts, magnesium salts and, if appropriate, vitamins, at temperatures between 0° C. and 100° C., preferably between 10° C. and 60° C., while passing in oxygen. During this process, the pH value of the liquid nutrient medium may be kept constant, i.e. can be regulated during culturing or not. Culturing can be effected batchwise, semibatchwise or continuously. Nutrients can be provided at the beginning of the fermentation or fed in semicontinuously or continuously.

A recombinant expression cassette according to the invention can advantageously be introduced into an organism or into cells, tissues, organs, parts or seeds thereof (preferably into plants or plant cells, tissues, organs, parts or seeds) by using vectors in which the recombinant expression cassettes are present. The recombinant expression cassette can be introduced into the vector (for example a plasmid) via a suitable restriction cleavage site. The resulting plasmid is first introduced into *E. coli*. Correctly transformed *E. coli* are selected, grown, and the recombinant plasmid is obtained by methods with which the skilled worker is familiar. Restriction analysis and sequencing may be used for verifying the cloning step.

An expression cassette according to the invention can advantageously be introduced into cells, preferably plant cells, using vectors. Examples of vectors are plasmids, cosmids, phages, viruses or else *agrobacteria*. In a preferred embodiment, the expression cassette is introduced by means of plasmid vectors. Preferred vectors are those which make possible stable integration of the expression cassette into the host genome.

Generating a transformed organism (or a transformed cell or tissue) requires introducing the DNA, RNA or protein in question into the host cell in question.

A multiplicity of methods are available for this procedure, which is referred to as transformation (or transduction or transfection) (Keown et al. (1990) Methods in Enzymology 185:527-537). Thus, for example, the DNA or RNA can be introduced directly by means of microinjection or by bombardment with DNA-coated microparticles. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Such methods are described (Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

The desaturases or conjugases can be used for the recombinant modification of a wide range of organisms, preferably of plants, so that these become a de-novo producer of one or more products derived from lipids, such as the two CLA isomers. Plants are initially regenerated after the transformation step and subsequently cultured or grown as usual.

Cloning vectors and techniques for the genetic manipulation of ciliates and algae are known to the skilled worker (WO 98/01572; Falciatore et al. (1999) Marine Biotechnology 1 (3):239-251; Dunahay et al. (1995) J Phycol 31:10004-1012).

Various methods and vectors for introducing genes into the genome of plants and for regenerating plants from plant tissues or plant cells are known (Plant Molecular Biology and Biotechnology (CRC Press, Boca Raton, Fla.), chapter 6/7, pp. 71-119 (1993); White F F (1993) Vectors for Gene Transfer in Higher Plants; in: Transgenic Plants, Bd. 1, Engineering and Utilization, Hrsgb.: Kung und R. Wu, Academic Press, 15-38; Jenes B et al. (1993) Techniques for Gene Transfer, in: Transgenic Plants, Bd. 1, Engineering and Utilization, Hrsgb.: Kung und R. Wu, Academic Press, S.128-143; Potrykus (1991) Annu Rev Plant Physiol Plant Molec Biol 42:205-225; Halford N G, Shewry P R (2000) Br Med Bull 56(1):62-73). They include, for example, those mentioned above. In plants, the methods which have been described for transforming and regenerating plants from plant tissues or plant cells are exploited for transient or stable transformation. Suitable methods are, in particular, protoplast transformation by polyethylene glycol-induced DNA uptake, the biolistic process with the gene gun, what is known as the particle bombardment method, electroporation, the incubation of dry embryos in DNA-containing solution, and microinjection. In the case of these "direct" transformation methods, the plasmid used need not meet any particular requirements. It is possible to use simple plasmids such as those from the pUC series, pBR322, M13mp series, pACYC184 and the like. If intact plants are to be regenerated from the transformed cells, the plasmid must contain an additional selectable marker gene.

In addition to these "direct" transformation techniques, transformation may also be effected by bacterial infection by means of *Agrobacterium tumefaciens* or *Agrobacterium rhizogenes*. These strains contain a plasmid (Ti and Ri plasmid, respectively) which is transferred to the plant following infection with *Agrobaterium*. Part of this plasmid, referred to as T-DNA (transferred DNA), is integrated into the genome of the plant cell. As an alternative, *agrobacterium* is also capable of transferring binary vectors (mini-Ti plasmids) to plants, and these vectors are integrated into the plants' genome. *Agrobacterium*-mediated transformation is best suited to dicotyledonous, diploid plant cells, while the direct transformation techniques are suitable for any cell type. Methods for the *agrobacterium*-mediated transformation are described, for example, by Horsch R B et al. (1985) Science 225:1229f. If *agrobacteria* are used, the expression cassette is integrated into specific plasmids, namely either into a shuttle vector (intermediate vector) or into a binary vector. If a Ti or Ri plasmid is used for the transformation, at least the right border, but in this case the right and left border, of the Ti or Ri plasmid T-DNA is linked to the expression cassette to be inserted as flanking region.

Binary vectors are preferably used for transformation with *Agrobacterium*. Binary vectors are capable of replication both in *E. coli* and in *Agrobacterium*. As a rule, they contain a selection marker gene and a linker or polylinker flanked by the right and left T-DNA border sequence. They can be transformed directly into *Agrobacterium* (Holsters et al. (1978) Mol Gen Genet 163:181-187). The selection marker gene, which is, for example, the nptII gene, which confers resistance to kanamycin, permits a selection of transformed *agrobacteria*. The *agrobacterium* which acts as host organism in this case should already contain a plasmid with the vir region. The latter is required for transferring the T-DNA to the plant cells. An *agrobacterium* transformed in this way can be used for transforming plant cells. The use of T-DNA for the transformation of plant cells has been studied intensively and described (EP 120 516; Hoekema, In: The Binary Plant Vector System, Offsetdrukkerij Kanters B. V., Alblasserdam, Chapter V; An et al. (1985) EMBO J 4:277-287). Various binary vectors are known, some of which are commercially available, such as, for example, pBI101.2 or pBIN19 (Clontech Laboratories, Inc. USA; Bevan et al. (1984) Nucl Acids Res 12:8711), pBinAr, pPZP200 or pPTV.

The *agrobacteria* which have been transformed with such a vector can then be used in the known manner for transforming plants, in particular crop plants, such as, for example, oilseed rape, for example by bathing scarified leaves or leaf segments in an agrobacterial solution and subsequently culturing them in suitable media. The transformation of plants with *agrobacteria* is described (White F F, Vectors for Gene Transfer in Higher Plants; in Transgenic Plants, Vol. 1, Engineering and Utilization, edited by S. D. Kung and R. Wu, Academic Press, 1993, pp. 15-38; Jenes B et al. (1993) Techniques for Gene Transfer, in: Transgenic Plants, Vol. 1, Engineering and Utilization, edited by S. D. Kung and R. Wu, Academic Press, pp. 128-143; Potrykus (1991) Annu Rev Plant Physiol Plant Molec Biol 42:205-225). Transgenic plants which contain the above-described desaturase or conjugase, pro-desaturase or conjugase or proOIL nucleic acids or recombinant expression cassettes or vectors according to the invention which are integrated can be regenerated in the known manner from the transformed cells of the scarified leaves or leaf segments.

Stably transformed cells, i.e. those which contain the inserted DNA integrated into the DNA of the host cell, can be selected from untransformed cells when a selectable marker is part of the inserted DNA. By way of example, any gene which is capable of conferring resistance to antibiotics or herbicides (such as kanamycin, G 418, bleomycin, hygromycin or phosphinothricin and the like) is capable of acting as marker (see above). Transformed cells which express such a marker gene are capable of surviving in the presence of concentrations of such an antibiotic or herbicide which kill an untransformed wild type. Examples are mentioned above and preferably comprise the bar gene, which confers resistance to the herbicide phosphinothricin (Rathore K S et al. (1993) Plant Mol Biol 21 (5):871-884), the nptII gene, which confers resistance to kanamycin, the hpt gene, which confers resistance to hygromycin, or the EPSP gene, which confers resistance to the herbicide Glyphosate. The selection marker permits selection of transformed cells from untransformed cells (McCormick et al. (1986) Plant Cell Reports 5:81-84). The plants obtained can be bred and hybridized in the customary manner. Two or more generations should preferably be grown in order to ensure that the genomic integration is stable and hereditary.

When a transformed plant cell has been generated, an intact plant can be obtained using methods with which the skilled worker is familiar. Callus cultures are an example of a starting material. The development of shoot and root can be induced in this as yet undifferentiated cell biomass in the known manner. The seedlings obtained can be planted out and grown. Suitable methods are described (Fennell et al. (1992) Plant Cell Rep. 11: 567-570; Stoeger et al (1995) Plant Cell Rep. 14:273-278; Jahne et al. (1994) Theor Appl Genet 89:525-533).

The expression efficacy of the recombinantly expressed nucleic acids can be determined for example in vitro by shoot-meristem propagation using one of the above-described selection methods. Moreover, changes in the nature and level of the expression of a desaturase or a proOIL nucleic acid sequence and their effect on the CLA and/or fatty acid biosynthesis rate can be tested in greenhouse experiments using test plants.

Those transgenic organisms which have improved CLA production in comparison with the untransformed wild type are selected by preference. Improved CLA production means for the purposes of the present invention for example the artificially acquired ability of an increased biosynthesis rate of at least one compound from the group of CLA, its esters, such as, for example, CoA esters or glyceride esters, in the transgenic organism in comparison with the non-genetically-modified starting organism. In this context, CLA production in the transgenic organism is preferably increased by 10%, especially preferably by 50%, very especially preferably by 100% in comparison with the non-genetically-modified organism. Improved may also refer to an advantageously modified qualitative composition of the CLA mixture, i.e. an increased content in (9Z,11E)-CLA and/or (10E,12Z)-CLA in comparison with the starting organism.

Also in accordance with the invention are cells, cell cultures, parts—such as, for example, roots, leaves and the like in the case of transgenic plant organisms—and transgenic propagation material such as seeds or fruits which are derived from the above-described transgenic organisms.

The invention furthermore relates to the use of the above-described transgenic organisms according to the invention and to the cells, cell cultures, parts—such as, for example, roots, leaves and the like in the case of transgenic plant organisms—and transgenic propagation material such as seeds or fruits which are derived from them for the production of foodstuffs or feedstuffs, cosmetics or fine chemicals, such as free fatty acids, in particular CLA. Particularly preferred is the use for the production of CLA-containing lipids, preferably triglycerides.

Genetically modified plants according to the invention which can be consumed by humans and animals may also be used as foodstuffs or feedstuffs, for example directly or following processing known per se.

After the organisms have been cultured, the lipids are obtained in the customary manner. To this end, the organisms can first be digested post-harvest or else used directly. The lipids are advantageously extracted with suitable solvents such as apolar solvents, such as hexane or ethanol, isopropanol or mixtures such as hexane/isopropanol, phenol/chloroform/isoamyl alcohol, at temperatures between 0° C. to 80° C., preferably between 20° C. and 50° C. As a rule, the biomass is extracted with an excess of solvent, for example with a 1:4 excess of solvent to biomass. The solvent is subsequently removed, for example via distillation. Extraction may also be effected with supercritcal $CO_2$. Following extraction, the remainder of the biomass can be removed, for example via filtration.

The crude oil obtained in this manner can subsequently be purified further, for example by removing cloudiness by treatment with polar solvents such as acetone or chloroform, followed by filtration or centrifugation. Further purification over columns is also possible.

To obtain the free fatty acids from the triglycerides, the latter are hydrolyzed in the customary manner.

The invention furthermore relates to vegetable oils, fatty acid mixtures and/or triglyceride mixtures with an increased content of unsaturated fatty acids, preferably CLA, and which has been produced by the abovementioned processes according to the invention, and to their use for the production of foodstuffs, animal feed, cosmetics or pharmaceuticals. To this end, they are added in customary amounts to the foodstuffs, the animal feed, the cosmetics or pharmaceuticals.

Sequences
1. SEQ ID NO: 1: Nucleic acid sequence encoding an acyl-CoA E1-desaturase from *Epiphyas postvittana*.
2. SEQ ID NO: 2: Protein sequence encoding an acyl-CoA E1-desaturase from *Epiphyas postvittana*.
3. SEQ ID NO: 3: Nucleic acid sequence encoding an acyl-CoA Z/E11-desaturase from *Ostrinia nubilalis*.
4. SEQ ID NO: 4: Protein sequence encoding an acyl-CoA Z/E11-desaturase from *Ostrinia nubilalis*.

5. SEQ ID NO: 5: Nucleic acid sequence encoding an acyl-CoA Z/E11-desaturase from *Ostrinia furnacalis*.
6. SEQ ID NO: 6: Protein sequence encoding an acyl-CoA Z/E11-desaturase from *Ostrinia furnacalis*.
7. SEQ ID NO: 7: Nucleic acid sequence encoding an acyl-CoA Δ11-desaturase from *Helicoverpa zea*.
8. SEQ ID NO: 8: Protein sequence encoding an acyl-CoA Δ11-desaturase from *Helicoverpa zea*.
9. SEQ ID NO: 9: Nucleic acid sequence encoding an acyl-CoA Δ11-desaturase from *Trichoplusia ni*.
10. SEQ ID NO: 10: Protein sequence encoding an acyl-CoA Δ11-desaturase from *Trichoplusia ni*.
11. SEQ ID NO: 11: Nucleic acid sequence encoding an acyl-CoA Δ11-desaturase from *Argyrotaenia velutinana*.
12. SEQ ID NO: 12: Protein sequence encoding an acyl-CoA Δ11-desaturase from *Argyrotaenia velutinana*.
13. SEQ ID NO: 13: Nucleic acid sequence encoding an acyl-CoA Z10-desaturase from *Planotortrix octo*.
14. SEQ ID NO: 14: Protein sequence encoding an acyl-CoA Z10-desaturase from *Planotortrix octo*.

15. SEQ ID NO: 15: 5'-ATYACHGCCGGKKMYCAYMG-3'
16. SEQ ID NO: 16: 5'-GGRAABDYGTGRTGGWAGTT-3'
17. SEQ ID NO: 17: 5'-CCCCAYCRNCTSTGGWCNCA-3'
18. SEQ ID NO: 18: 5'-CCCTCTAGARTGRRWARTTRTGRWA-3'
19. SEQ ID NO: 19: 5'-TAATACGACTCACTATAG-3'
20. SEQ ID NO: 20: 5'-ACATAACTAATTACATGAT-3'

21. SEQ ID NO: 21: Nucleic acid sequence encoding an acyl-CoA Z/E11-desaturase from *Pectinophora gossypiella*
22. SEQ ID NO: 22: Amino acid sequence encoding an acyl-CoA Z/E11-desaturase from *Pectinophora gossypiella*

EXAMPLES

The following examples illustrate embodiments of the invention, but should not be viewed as limiting the scope of the invention.

The invention is illustrated in greater detail in the use examples which follow, referring to the appended figures. The abbreviations used have the following meaning:

General Methods

The cloning steps carried out for the purposes of the present invention such as, for example, restriction cleavages, agarose gel electrophoreses, purification of DNA fragments, transfer of nucleic acids to nitrocellulose and nylon membranes, linking of DNA fragments, transformation of *E. coli* cells, bacterial culture and sequence analysis of recombinant DNA, are carried out as described by Sambrook et al. (1989) Cold Spring Harbor Laboratory Press; ISBN 0-87969-309-6. Oligonucleotides can be synthesized chemically for example in the known manner using the phosphoamidite method (Voet, Voet, 2$^{nd}$ edition, Wiley Press New York, pp. 896-897). The cloning steps carried out within the present invention, such as, for example, restriction cleavages, agarose gel electrophoresis, purification of DNA fragments, transfer of nucleic acids to vitrocellulose and nylon membranes, linking DNA fragments, transformation of *E. coli* cells, bacterial cultures, propagation of phages and sequence analysis of recombinant DNA were carried out as described by Sambrook et al. (1989) Cold Spring Harbor Laboratory Press; ISBN 0-87969-309-6. Recombinant DNA molecules were sequenced using a laser fluorescence DNA sequencer from Licor (sold by MWG Biotech, Ebersbach) following the method of Sanger (Sanger et al. (1977) Proc Natl Acad Sci USA 74:5463-5467).

Example 1

Breeding the Lepidoptera Insects

The insects are kept on suitable host plants in terrarria. The growth conditions are: 27° C., day-night rhythm: 14 h light, 10 hours darkness. Insects and larvae are transferred to fresh plants twice per week. Puppae are collected, and males and females are kept separately in terrarria until the adult insects hatch. Approximately 1 to 2 days after the insects have hatched, the pheromone glands can be isolated.

Example 2

Isolation of Desaturase or Conjugase cDNAs by Means of Degenerate Primers

The pheromone glands are isolated from the abdomen of adult moths and frozen in liquid $N_2$ until total RNA is isolated, for example by means of TRIzol (Gibco/BRL) following the manufacturer's instructions. Experience has shown that approximately 60 to 80 μg of total RNA can be isolated from approximately 30 mg fresh tissue. Approximately 5 μg of total RNA is employed to produce a first-strand cDNA with an oligo(dT) primer. This may be done for example using the SMART RACE cDNA amplification kit (Clontech) following the manufacturer's instructions. This single-strand cDNA acts as template for a PCR in which the central region of the desaturase/conjugase cDNA is amplified. Two degenerate primers are designed in such a way that they are capable of amplifying the conserved central region of the desaturases/conjugases from lepidopterans and employed in the following PCR protocol:

| | |
|---|---|
| 5 μl | dilute single-strand cDNA |
| 0.2 mM | dATP, dTTP, dGTP, dCTP |
| 0.5 μM | 5' primer (SEQ ID NO 8) |
| 0.5 μM | 3' primer (SEQ ID NO 9) |
| 10 μl | 5X Advantage 2 reaction buffer (Clontech) |
| 1 μl | 50X Advantage 2 DNA polymerase mix (Clontech) |
| $H_2O$ to 50 μl | |

As an alternative, the degenerate primers with SEQ ID NO: 10 and SEQ ID NO: 11 are used as primer pair for the amplification of the central desaturase region.

The PCR was carried out under the following cycle conditions:

1 step at: 94° C. (5 min)
35 cycles at: 94° C. (30 sec), 56° C. (30 sec), 72° C. (3 min).
1 step at: 72° C. (10 min)
Waiting position: 4° C.

The PCR product is ligated directly, for example into the linearized TOPO TA PCR 2.1 vector (Invitrogen) and subsequently transformed into competent *E. coli* TOP 10 cells (Invitrogen). Positive colonies are reamplified, the plasmid DNA is purified (Qiagen Plasmid Mini Kit) and subsequently sequenced.

Owing to the sequence information obtained, gene-specific primers can be derived and used for amplifying 5' and 3' regions (SMART RACE cDNA Amplification Kit Clontech)). Again, these PCR products are ligated into the TOPO TA PCR 2.1 vector (Invitrogen) and subsequently transformed into competent TOP 10 cells (Invitrogen). Positive colonies are reamplified, and the plasmid DNA is purified (Qiagen Plasmid Mini Kit) and subsequently sequenced.

Starting from the fragments generated in this manner, the complete sequence of a desaturase/conjugase can be put together using standard cloning techniques and transferred for characterization purposes for example into the pYES2 vector (Invitrogen) for expression in yeast. *Saccharomyces* INVSc1 (Invitrogen) are transformed with the corresponding pYES2 expression vectors by means of a modified PEG/lithium acetate protocol (Ausubel et al. (1996) Current Protocols in Molecular Biology. John Wiley and Sons, New York). Following selection on CMdum agar plates with 2% glucose, four pYES2DESAT transformants (pYES2DESATa-d) and one pYES2 transformant are selected for further cultivation and functional expression.

Example 3

Functional Expression of a Desaturase/Conjugase in Yeast

Preculture: 20 ml of CMdum liquid medium supplemented with 2% (w/v) raffinose were inoculated with the transgenic yeast clones (pYES2DESATa-d, pYES2) and cultured for 3 days at 30° C., 200 rpm, until an optical density at 600 nm ($OD_{600}$) of 1.5-2 had been reached.

Main culture: For the expression, 20 ml of CMdum liquid medium supplemented with 2% of raffinose and 1% (v/v) Tergitol NP-40 were concentrated with the corresponding substrates such as stearic acid, palmitic acid or myristic acid, to a final concentration of 0.003% (w/v). The media were inoculated with the precultures to an $OD_{600}$ of 0.05. Expression was induced for 16 hours at an $OD_{600}$ of 0.2 using 2% (w/v) galactose, whereafter the cultures had reached an $OD_{600}$ of 0.8 to 1.2.

Fatty acid analysis: The total fatty acids were extracted from yeast cultures and analyzed by means of gas chromatography. To this end, cells of 5 ml of culture were harvested by centrifugation (1000×g, 10 min, 4° C.) and washed once with 100 mM NaHCO3, pH 8.0 in order to remove residues of medium and fatty acids. To prepare the fatty acid methyl esters (FAMES), the cell sediments were shock-frozen in liquid $N_2$ and lyophilized at 30° C. under $N_2$ gas. The pellet is homogenized in 1% sodium methoxide in methanol and the homogenate is incubated for 20 minutes at room temperature. Equal volumes of 1 M NaCl and n-heptane are subsequently added, the sample is mixed and the mixture is transferred into a GC tube. The samples are separated from a DB-wax capillary column (30 m, 0.25 mm, 0.25 µm; Agilent J & W) in a Hewlett Packard 6890 gas chromatograph equipped with a flame ionization detector. The oven temperature was programmed from 60° C. (hold 5 min) to 200° C. at a rate of 20° C./min (hold 20 min) and finally to 250° C. (hold 30 min) at a rate of 20° C./min. The carrier gas used was nitrogen (1.6 ml/min). The fatty acids were identified by comparison with retention times of FAME standards (SIGMA). The following fatty acids are preferably used as standard for this purpose: c9-16:1, t9-16:1, 18:0, c9-18:1, t9-18:1, c11-18:1, t11-18:1, c9, c12-18:2, t9, t12-18:2, c9, t11-18:2, t10, c12-18:2. (The nomenclature of the standards corresponds to the nomenclature conventionally used for fatty acids and first indicates the configuration (c=cis or t=trans) and position of the double bond or chain length of the fatty acid).

Further feeding experiments with various other fatty acids (for example lauric acid, trans-vaccenic acid, cis-vaccenic acid, E10-octadecenoic acid or Z10-octadecenoic acid) can be carried out for in-depth verification of the substrate selectivity of this desaturase/conjugase.

Example 4

Expression Cloning of Desaturase/Conjugase from Lepidoptera in *Saccharomyces cerevisiae* a) Generation of the cDNA Library

The pheromone glands are isolated from the abdomen of adult moths and frozen in liquid $N_2$ until total RNA is isolated, for example by means of TRIzol (Gibco/BRL) following the manufacturer's instructions. Experience has shown that approximately 60 to 80 µg of total RNA can be isolated from approximately 30 mg fresh tissue. Approximately 5 µg of total RNA is employed for generating a cDNA library. This may be done for example using the SMART cDNA Library Construction Kit (Clontech). The isolated double-stranded cDNA is finally ligated into the linearized pYES2 (Invitrogen) yeast expression vector. To this end, the multiple cloning site of the pTriplEx2 vector (Clontech) is first inserted into pYES2. The double-stranded cDNA is digested with SfiIA and SfiIB and then cloned in a directed fashion into the vector which has been modified.

b) Yeast Transformation

Approximately 1.5 µg of plasmid DNA is transformed into INVSc1 (Invitrogen) using the *Saccharomyces cerevisiae* EASY COMP Transformation kit (Invitrogen) following the manufacturer's instructions. Two 50 µl-batches are plated onto selection medium in a large square Petri dish (245×245 mm) and incubated for 3 days at 30° C.

c) Yeast Culture in Microtiter Plates

Individual colonies are transferred into microtiter plates (MTP) using a Pick Roboter. The preculture is carried out in 200 µl of medium [1×CSM-Ura; 1×YNB without amino acids and sugar; 0.5% raffinose; 5% glycerol; 40 mg/l adenin sulfate; 0.5% ammonium sulfate] for 72 hours at 30° C. and 250 revolutions per minute. An $OD_{600}$ of 0.2 is adjusted in the main culture by addition of an average volume from the preculture. The main culture is carried out in 1 ml of medium [1×CSM-Ura; 1×YNB without amino acids and sugar; 0.5% raffinose; 2% galactose; 0.2% Tergitol NP-40; 40 mg/l adenin sulfate; 0.5% ammonium sulfate; 0.3 mM fatty acid substrate] for 2 to 3 weeks at 16° C. and 250 revolutions per minute until an $OD_{600}$ of 3 to 4 has been reached.

d) Fatty Acid Analysis

The yeast cells are sedimented (1000×g, 10 min, 4° C.) and stored at −80° C. until further processing. To prepare the fatty acid methyl esters (FAMES), the cell sediments are shock-frozen in liquid $N_2$ and lyophilized under $N_2$ gas at 30° C. The pellet is homogenized in 1% sodium methoxide in methanol and incubated for 20 minutes at room temperature. Equal volumes of 1 M NaCl and n-heptane are subsequently added, the samples are mixed and the supernatant is transferred into a GC tube. The samples are separated on a DB-wax capillary column (30 m, 0.25 mm, 0.25 µm; Agilent J & W) in a Hewlett Packard 6890 gas chromatograph equipped with a flame ionization detector. The oven temperature was programmed from 60° C. (hold 5 min) to 200° C. at a rate of 20° C./min (hold 20 min) and finally to 250° C. (hold 30 min) at a rate of 20° C./min. the carrier gas used was nitrogen (1.6 ml/min). The fatty acids were identified by comparison with retention times of FAME standards (SIGMA). The same standards as listed in Example 3 are used. Further feeding experiments with various other fatty acids (for example lauric acid, trans-vaccenic acid, cis-vaccenic acid, E10-octadecenoic acid or Z10-octadecenoic acid) can be carried out for in-depth verification of the substrate selectivity of this desaturase/conjugase.

e) Plasmid Preparation of the Positive Yeasts:

Individual clones which have tested positively are again cultured in 10 ml of minimal medium [1×CSM-Ura; 1×YNB w/o AA, sugars; 2% glucose; 40 mg/l adenin sulfate] for 24 hours at 28° C. and sedimented by centrifugation when the $OD_{600}$ exceeded 3. The yeast pellet is incubated for 20 minutes at 37° C. in 400 µl, of SCE buffer [1.2 M sorbitol; 0.1 M sodium citrate, pH 7.0; 10 mM EDTA; 1 mg/ml Lytikase]. Then, 400 µl of STE buffer [2% SDS; 50 mM Tris/HCl, pH 8.0; 10 mM EDTA] are added to the cell lysate and the mixture is incubated for 10 minutes at room temperature. To precipitate the cell protein, 200 µl of 5 M sodium acetate are added and the mixture is placed on ice for 30 minutes. After centrifugation, the supernatant is transferred and precipitated with 2.5 volumes of ethanol. The pellet which has sedimented is washed with 70% ethanol and finally taken up in sterile water. If appropriate, the sequence of the desaturase/conjugase can be determined by sequencing using vector-specific primers (SEQ ID NO: 12 and 13).

Example 5

Manipulation of the Plant Fatty Acid Biosynthesis a) Generation of DNA Constructs for Expressing Desaturases/Conjugases from Lepidoptera in Transgenic Plants.

To generate chimeric DNA constructs for generating transgenic *A. thaliana* or *B. napus* plants which express the desaturases/conjugases from lepidopterans, use is made of the vector pBinAR (Höfgen and Willmitzer (1990) Plant Sci 66:221-230). This vector contains the CaMV (cauliflower mosaic virus) 35S promoter (Franck et al. (1980) Cell 21(1):285-294) and the termination signal of the octopine synthase gene (Gielen et al. (1984) EMBO J 3:835-846). After the desaturase/conjugase has been cloned into this vector, transgenic *A. thaliana* and *Brassica napus* plants are generated.

b) Generation of Transgenic *Arabidopis thaliana* Plants

Wild-type *Arabidopsis thaliana* plants (Columbia) are transformed with the *Agroabacterium tumefaciens* strain (GV3101 [pMP90]) on the basis of a modified vacuum infiltration method (Clough S and Bent A (1998) Plant J 16(6): 735-43; Bechtold N et al. (1993) in: Planta *Agrobacterium*-mediated gene transfer by infiltration of adult *Arabidopsis thaliana* plants. CRAcad Sci Paris 1144(2):204-212). The *Agrobacterium tumefaciens* cells which were used had previously been transformed with the plasmids.

Seeds of the primary transformants are selected on the basis of their resistance to antibiotics. Seedlings with resistance to antibiotics are planted into soil and subjected to biochemical analysis as fully-developed plants.

c) Generation of Transgenic *Brassica napus* Plants

Transgenic oilseed rape plants are generated following a protocol of Bade J B and Damm B (in Gene Transfer to Plants, Potrykus I and Spangenberg G (eds.) Springer Lab Manual, Springer Verlag, 1995, 30-38), which also states the composition of the media and buffers used.

The transformations are carried out with *Agrobacterium tumefaciens* strain GV3101 [pMP90]. The plasmids pBinAR-TkTP/Vit E-AT are used for the transformation. Seeds of *Brassica napus* var. *Westar* are surface-sterilized with 70% ethanol (v/v), washed for 10 minutes in water at 55° C., incubated for 20 minutes in 1% strength hypochlorite solution (25% v/v Teepol, 0.1% v/v Tween 20) and washed six times with sterile water for in each case 20 minutes. The seeds are dried for three days on filter paper, and 10 to 15 seeds are germinated in a glass flask containing 15 ml of germination medium. The roots and apices are removed from several seedlings (approximate size 10 cm), and the hypocotyls which remain are cut into pieces approximately 6 mm in length. The approx. 600 explants thus obtained are washed for 30 minutes with 50 ml of basal medium and transferred into a 300 ml flask. After addition of 100 ml of callus induction medium, the cultures are incubated for 24 hours at 100 rpm.

An overnight culture of the *Agrobacterium* strain is established at 29° C. in Luria broth medium supplemented with kanamycin (20 mg/l), and 2 ml of this culture are incubated in 50 ml of Luria broth medium without kanamycin for 4 hours at 29° C. until an $OD_{600}$ of 0.4 to 0.5 has been reached. After the culture has been pelleted for 25 minutes at 2000 rpm, the cell pellet is resuspended in 25 ml of basal medium. The concentration of the bacteria in the solution is brought to an $OD_{600}$ of 0.3 by addition of further basal medium.

The callus induction medium is removed from the oilseed rape explants using sterile pipettes, 50 ml of *Agrobacterium* solution are added, and the culture is mixed carefully and incubated for 20 minutes. The agrobacterial suspension is removed, the oilseed rape explants are washed for 1 minute using 50 ml of callus induction medium, and 100 ml of callus induction medium are subsequently added. Coculturing is performed for 24 hours on a orbital shaker at 100 rpm. Coculturing is stopped by withdrawing the callus induction medium, and the explants are washed twice for in each case 1 minute with 25 ml and twice for 60 minutes with in each case 100 ml of wash medium at 100 rpm. The wash medium together with the explants is transferred to 15 cm Petri dishes, and the medium is removed using sterile pipettes.

For the regeneration, batches of 20 to 30 explants are transferred into 90 mm Petri dishes which contain 25 ml of shoot induction medium supplemented with kanamycin. The Petri dishes are filled with 2 layers of Leukopor and incubated at 25° C. and 2000 lux at a 16-hour light/8-hour darkness photo period. Every 12 days, the developing calli are transferred to fresh Petri dishes containing shoot induction medium. All further steps for regenerating intact plants are carried out as described by Bade, J. B and Damm, B. (in: Gene Transfer to Plants, Potrykus I and Spangenberg G (eds.) Springer Lab Manual, Springer Verlag, 1995, 30-38).

d) Analysis of the Fatty Acid Pattern in the Transgenic Plants

The seeds of transgenic plants are homogenized directly in 1% sodium methoxide in methanol and the homogenate is incubated for 20 minutes at room temperature. Equal volumes of 1 M NaCl and n-heptane are subsequently added, the sample is mixed and the supernatant is transferred into a GC tube. The samples are separated on a DB-wax capillary column (30 m, 0.25 mm, 0.25 µm; Agilent J & W) in a Hewlett Packard 6890 gas chromatograph equipped with a flame ionization detector. The oven temperature was programmed from 60° C. (hold 5 min) to 200° C. at a rate of 20° C./min (hold 20 min) and finally to 250° C. (hold 30 min) at a rate of 20° C./min. The carrier gas used was nitrogen (1.6 ml/min). The fatty acids were identified by comparison with retention times of FAME standards (SIGMA). The same standards as stated in Example 3 are used.

Example 6

Functional Expression in Yeast of a Desaturase from the Lepidoptera *Pectinophora gossypiella*

A desaturase isolated from gland material of the moth *Pectinophora gossypiella* (SEQ ID No.: 21 and 22) was cloned into the yeast expression vector pYES2 (Invitrogen) by means of BamHI and EcoRI. The resulting construct was named pYES2::DesPgos. Both pYES2::DesPgos and the control pYES2 were transformed into yeast cells (*Saccharomyces cerevisiae* INVSc1 [MAT, his3-1, leu2, trp1-289, ura3-52]; Invitrogen) using the S.c. Easy Comp Transformation Kit (Invitrogen). These yeast cells contained additionally the construct pESC::ACS for expressing a *Brassica napus* acetyl-CoA synthase. A single colony of both pYES2::DesPgos and of the control pYES2 was isolated on selection medium and grown for 2 days at 30° C. and 200 revolutions per minute in 50 ml of preculture medium (1*CSM-Leu/-Ura; 1*YNB w/o AA; 0.5% raffinose; 5% glycerol and 0.5% ammonium sulfate) to give a preculture. From these precultures, in each case 3 main cultures with an $OD_{0.06}$ in the case of the yeasts were inoculated with pYES2::DesPgos and with $OD_{0.1}$ in the case of yeasts with pYES2, both at 16° C. and at 30° C. The main culture medium (1*CSM-Leu/-Ura; 1*YNB w/o AA; 0.5% raffinose; 2% galactose; 0.2% Tergitol NP-40 and 0.5% ammonium sulfate) was treated with 0.3 mM stearic acid. After 4 days at 16° C. and 2 days at 30° C., the main cultures were adjusted to $OD_{1.2}$, and 10 ml were centrifuged for 30 minutes at RT and 17500 g. The pellet was resuspended in $H_2O$, heated for 10 minutes at 90° C. and again sedimented under the same conditions. The pellet was washed with $H_2O$, sedimented, shock-frozen in liquid nitrogen ($N_2$) and subsequently lyophilized under $N_2$. To extract the lipids and prepare fatty acid methyl esters (FAME), the pellet was homogenized in 300 µl of 1% sodium methoxide in methanol and incubated for 20 minutes at room temperature. In each case 300 µl of 1 M NaCl and n-heptane were subsequently added, the sample was mixed and the supernatant was transferred into a GC tube. The samples were separated on a DB-wax capillary column (30 m, 0.25 mm, 0.25 µm; Agilent J & W) in a Hewlett Packard 6890 gas chromatograph equipped with a flame ionization detector. The oven temperature was programmed from 60° C. (hold 5 min) to 200° C. at a rate of 20° C./min (hold 20 min) and finally to 250° C. (hold 30 min) at a rate of 20° C./min. The carrier gas used was nitrogen (1.6 ml/min). The fatty acids were identified by comparison with retention times of FAME standards (SIGMA).

Table 1 shows the relative distribution of the FAME of lipids from pYES2::DesPgos in comparison with the control pYES2 at 16° C. It can be seen that the expression of the *Pectinophora gossypiella* desaturase results in an accumulation of the following monounsaturated fatty acids: C16:1 D11, C18:1 D11 and C18:1 D13. Moreover, the heterologous expression of the *P. gossypiella* desaturase leads to the formation of (9Z,11E)-CLA.

Table 2 shows the relative distribution of the FAME of lipids of pYES2::DesPgos in comparison with the control pYES2 at 30° C. The expression results at 30° C. correspond to those at 16° C.: expression of the *Pectinophora gossypiella* desaturase in the yeast leads to an accumulation of the monounsaturated fatty acids C16:1D11, C18:1D11 and C18:1D13. Moreover, the heterologous expression of the *P. gossypiella* desaturase leads to the formation of (9Z,11E)-CLA.

TABLE 1

Heterologous expression of the *Pectinophora gossypiella* desaturase in *S. cerevisiae* at 16° C. The values represent the relative amount of the individual fatty acids in the total fatty acid spectrum.

| | pYES2 | | | | | pYES2::DesPgos | | | | |
|---|---|---|---|---|---|---|---|---|---|---|
| | Sample 1 | Sample 2 | Sample 3 | Mean | Standard deviation | Sample 1 | Sample 2 | Sample 3 | Mean | Standard deviation |
| C16:0 | 18.24 | 18.84 | 18.29 | 18.46 | 0.27 | 20.14 | 20.31 | 20.44 | 20.30 | 0.13 |
| C16:1Δ9 | 43.97 | 43.75 | 43.52 | 43.74 | 0.18 | 41.09 | 41.32 | 41.70 | 41.37 | 0.25 |
| C16:1Δ11 | 0.02 | 0.13 | 0.25 | 0.13 | 0.09 | 1.60 | 1.54 | 1.62 | 1.59 | 0.03 |
| C18:0 | 8.49 | 8.52 | 8.62 | 8.54 | 0.06 | 8.11 | 8.19 | 7.95 | 8.08 | 0.10 |
| C18:1Δ9 | 29.17 | 28.60 | 29.19 | 28.99 | 0.27 | 22.32 | 22.319 | 21.81 | 22.15 | 0.24 |
| C18:1Δ11 | 0.03 | 0.04 | 0.03 | 0.04 | 0.59 *10E−2 | 6.28 | 6.01 | 6.16 | 6.15 | 0.11 |
| C18:1Δ13 | 0 | 0 | 0 | 0 | 0 | 0.16 | 0.15 | 0.15 | 0.15 | 0.38 *10E−2 |
| C18:2-Z9,E11 | 0.01 | 0.01 | 0.01 | 0.01 | 0.21 *10E−2 | 0.05 | 0.04 | 0.04 | 0.05 | 0.26 *10E−2 |
| C18:2-Z9,Z11 | 0.01 | 0.01 | 0.01 | 0.01 | 0.10 *10E−2 | 0.04 | 0.04 | 0.04 | 0.04 | 0.19 *10E−2 |

TABLE 2

Heterologous expression of the *Pectinophora gossypiella* desaturase in *S. cerevisiae* at 30° C. The values represent the relative amount of the individual fatty acids in the total fatty acid spectrum.

| | pYES2 | | | | | pYES2::DesPgos | | | | |
|---|---|---|---|---|---|---|---|---|---|---|
| | Sample 1 | Sample 2 | Sample 3 | Mean | Standard deviation | Sample 1 | Sample 2 | Sample 3 | Mean | Standard deviation |
| C16:0 | 17.34 | 17.49 | 17.30 | 17.38 | 0.10 | 14.01 | 13.71 | 13.63 | 13.78 | 0.20 |
| C16:1Δ9 | 40.31 | 41.24 | 41.14 | 40.90 | 0.51 | 37.06 | 37.12 | 38.51 | 37.56 | 0.82 |
| C16:1Δ11 | 0.16 | 0.17 | 0.17 | 0.17 | 0.60 *10E−2 | 3.17 | 3.32 | 3.19 | 3.23 | 0.08 |
| C18:0 | 8.00 | 7.74 | 8.04 | 7.92 | 0.16 | 5.16 | 4.96 | 4.96 | 5.03 | 0.12 |
| C18:1Δ9 | 32.40 | 31.71 | 31.68 | 31.93 | 0.41 | 25.49 | 25.24 | 25.22 | 25.32 | 0.15 |
| C18:1Δ11 | 1.57 | 1.57 | 1.53 | 1.56 | 0.02 | 14.32 | 14.90 | 14.00 | 14.41 | 0.45 |
| C18:1Δ13 | 0.04 | 0.04 | 0.06 | 0.05 | 0.01 | 0.32 | 0.33 | 0.37 | 0.34 | 0.03 |
| C18:2-Z9,E11 | 0.01 | 0.01 | 0.01 | 0.01 | 0.06 *10E−2 | 0.08 | 0.09 | 0.08 | 0.08 | 0.75 *10E−2 |
| C18:2-Z9,Z11 | 0.04 | 0.03 | 0.04 | 0.04 | 0.31 *10E−2 | 0.14 | 0.14 | 0.15 | 0.15 | 0.55 *10E−2 |

We claim:

1. A process for production of triglycerides comprising unsaturated fatty acids, which process comprises
   recombinantly expressing at least one fatty-acid desaturase from an insect of the order Lepidoptera in an oil producing plant, and
   obtaining triglycerides from the oil producing plant,
   wherein the fatty-acid desaturase generates a double bond at position C11 in a fatty acid, fatty-acid CoA ester, or fatty-acid derivative,
   wherein the oil producing plant is selected from the group consisting of linseed, soya, oilseed rape, coconut, oil palm, safflower, castor-oil plant, peanut, cacao tree and sunflower.

2. The process of claim 1, wherein the fatty-acid desaturase generates a cis or trans double bond in fatty acids, fatty-acid CoA esters, or fatty acid derivatives with a fatty acid chain length of 16 or 18 C atoms.

3. The process of claim 1, wherein the fatty-acid desaturase comprises a sequence having at least 65% homology with a fatty-acid desaturase containing the sequence of SEQ ID NO: 2.

4. The process of claim 1, wherein the unsaturated fatty acids comprise a conjugated linoleic acid.

5. The process of claim 1, wherein the fatty-acid desaturase generates a trans double bond in the unsaturated fatty acids.

6. The process of claim 5, wherein greater than 60% of the unsaturated fatty acids contain the trans double bond.

7. The process of claim 5, wherein greater than 90% of the unsaturated fatty acids contain the trans double bond.

8. The process of claim 1, wherein the fatty-acid desaturase comprises a sequence having at least 90% homology to the sequence of SEQ ID NO: 2.

9. The process of claim 1, wherein the fatty acid desaturase comprises the sequence of SEQ ID NO: 2.

10. The process of claim 1, wherein the fatty-acid desaturase is encoded by a nucleotide sequence comprising the nucleotide sequence of SEQ ID NO: 1 or a nucleotide sequence having at least 90% identity to SEQ ID NO: 1.

11. The process of claim 1, further comprising adding the triglycerides to foodstuffs, feedstuffs, cosmetics or fine chemicals.

12. A process for production of triglycerides comprising unsaturated fatty acids, which process comprises recombinantly expressing at least one fatty-acid desaturase from an insect of the order Lepidoptera in a plant; and obtaining the triglycerides from the plant, wherein the fatty-acid desaturase generates a double bond at position C11 in a fatty acid, fatty-acid CoA ester, or fat-acid derivative.

13. The process of claim 12, further comprising adding the triglycerides to foodstuffs, feedstuffs, cosmetics or fine chemicals.

* * * * *

SEQUENCE LISTING

<160> NUMBER OF SEQ ID NOS: 22

<210> SEQ ID NO 1
<211> LENGTH: 999
<212> TYPE: DNA
<213> ORGANISM: Epiphyas postvittana
<220> FEATURE:
<221> NAME/KEY: CDS
<222> LOCATION: (1)..(996)
<223> OTHER INFORMATION: Acyl-CoA E11 desaturase

<400> SEQUENCE: 1

| | | | | | | | | | | | | | | | | |
|---|---|---|---|---|---|---|---|---|---|---|---|---|---|---|---|---|
| atg | gct | cca | aac | gta | gaa | gaa | att | gaa | act | gat | tta | aca | gaa | act | gaa | 48 |
| Met | Ala | Pro | Asn | Val | Glu | Glu | Ile | Glu | Thr | Asp | Leu | Thr | Glu | Thr | Glu | |
| 1 | | | | 5 | | | | | 10 | | | | | 15 | | |
| gag | aaa | tgg | gaa | aaa | tta | gtt | gca | ccc | cag | gct | gct | ccc | aga | aag | cat | 96 |
| Glu | Lys | Trp | Glu | Lys | Leu | Val | Ala | Pro | Gln | Ala | Ala | Pro | Arg | Lys | His | |
| | | | 20 | | | | | 25 | | | | | 30 | | | |
| gaa | ata | tta | tac | acg | aac | ctg | cta | atc | ttc | ggc | tac | ggg | cat | ctc | gct | 144 |
| Glu | Ile | Leu | Tyr | Thr | Asn | Leu | Leu | Ile | Phe | Gly | Tyr | Gly | His | Leu | Ala | |
| | 35 | | | | | 40 | | | | | 45 | | | | | |
| gga | ctg | tac | ggt | tta | tac | ctg | tgc | ttc | act | tct | gct | cga | ttg | caa | act | 192 |
| Gly | Leu | Tyr | Gly | Leu | Tyr | Leu | Cys | Phe | Thr | Ser | Ala | Arg | Leu | Gln | Thr | |
| 50 | | | | | 55 | | | | | 60 | | | | | | |
| att | ata | ctt | gct | ttc | atc | ctt | cac | gca | atg | gca | atc | ttg | ggc | ata | aca | 240 |
| Ile | Ile | Leu | Ala | Phe | Ile | Leu | His | Ala | Met | Ala | Ile | Leu | Gly | Ile | Thr | |
| 65 | | | | | 70 | | | | | 75 | | | | | 80 | |
| gcc | ggc | gct | cac | aga | ctc | tgg | aca | cac | aga | agc | tac | aaa | gcg | aca | atg | 288 |
| Ala | Gly | Ala | His | Arg | Leu | Trp | Thr | His | Arg | Ser | Tyr | Lys | Ala | Thr | Met | |
| | | | | 85 | | | | | 90 | | | | | 95 | | |
| cct | ctt | caa | atc | atc | ctt | ata | att | ttc | aac | tcg | ctg | tca | ttc | caa | aac | 336 |
| Pro | Leu | Gln | Ile | Ile | Leu | Ile | Ile | Phe | Asn | Ser | Leu | Ser | Phe | Gln | Asn | |
| | | | 100 | | | | | 105 | | | | | 110 | | | |
| agt | gcc | att | aat | tgg | gtc | aga | gac | cac | cga | tcg | cac | cac | aag | tat | tgt | 384 |
| Ser | Ala | Ile | Asn | Trp | Val | Arg | Asp | His | Arg | Ser | His | His | Lys | Tyr | Cys | |
| | | 115 | | | | | 120 | | | | | 125 | | | | |
| gat | acg | gac | gcc | gac | cct | cac | aac | gcc | gcc | aga | gga | ctc | ttc | tac | tcc | 432 |
| Asp | Thr | Asp | Ala | Asp | Pro | His | Asn | Ala | Ala | Arg | Gly | Leu | Phe | Tyr | Ser | |
| | 130 | | | | | 135 | | | | | 140 | | | | | |
| cat | atc | ggt | tgg | ctc | ttg | gtg | aag | aag | cac | cct | gaa | gtc | aag | aag | aga | 480 |
| His | Ile | Gly | Trp | Leu | Leu | Val | Lys | Lys | His | Pro | Glu | Val | Lys | Lys | Arg | |
| 145 | | | | | 150 | | | | | 155 | | | | | 160 | |
| gga | aag | atg | acc | gac | atg | tcc | gat | gtc | tac | agg | aac | ccc | gtc | ttg | cgg | 528 |
| Gly | Lys | Met | Thr | Asp | Met | Ser | Asp | Val | Tyr | Arg | Asn | Pro | Val | Leu | Arg | |
| | | | | 165 | | | | | 170 | | | | | 175 | | |
| ttt | caa | aag | aag | tat | gca | gtg | cct | ttc | ata | ggc | acg | ata | tgt | ttc | gta | 576 |
| Phe | Gln | Lys | Lys | Tyr | Ala | Val | Pro | Phe | Ile | Gly | Thr | Ile | Cys | Phe | Val | |
| | | | 180 | | | | | 185 | | | | | 190 | | | |
| ctg | cca | acg | ata | ata | cct | atg | tat | ttc | tgg | gga | gaa | tct | ttg | aac | aac | 624 |
| Leu | Pro | Thr | Ile | Ile | Pro | Met | Tyr | Phe | Trp | Gly | Glu | Ser | Leu | Asn | Asn | |
| | | 195 | | | | | 200 | | | | | 205 | | | | |
| gct | tgg | cac | atc | acg | ctg | cta | cgc | tat | atc | ttt | agc | atg | cac | acg | ata | 672 |
| Ala | Trp | His | Ile | Thr | Leu | Leu | Arg | Tyr | Ile | Phe | Ser | Met | His | Thr | Ile | |
| | 210 | | | | | 215 | | | | | 220 | | | | | |
| ttc | ctt | gtg | aac | agc | gta | gcc | cat | cta | tgg | ggc | aac | agg | cct | tac | gac | 720 |
| Phe | Leu | Val | Asn | Ser | Val | Ala | His | Leu | Trp | Gly | Asn | Arg | Pro | Tyr | Asp | |
| 225 | | | | | 230 | | | | | 235 | | | | | 240 | |
| aaa | aac | att | ttg | cca | gcg | gac | aac | aga | aca | tta | tca | atc | gca | acg | tta | 768 |
| Lys | Asn | Ile | Leu | Pro | Ala | Asp | Asn | Arg | Thr | Leu | Ser | Ile | Ala | Thr | Leu | |
| | | | | 245 | | | | | 250 | | | | | 255 | | |

-continued

```
gga gaa gcc agc cac aac tac cat cac acg ttt cct tgg gac tat aga    816
Gly Glu Ala Ser His Asn Tyr His His Thr Phe Pro Trp Asp Tyr Arg
            260                 265                 270 tct aca gaa cta ggg tat tta cca act aac ttt act acg aac ttc att    864
Ser Thr Glu Leu Gly Tyr Leu Pro Thr Asn Phe Thr Thr Asn Phe Ile
        275                 280                 285 gat ttc ttc gct tgg atc ggc tgg gca tac gac ttg aaa aca aca tcg    912
Asp Phe Phe Ala Trp Ile Gly Trp Ala Tyr Asp Leu Lys Thr Thr Ser
290                 295                 300 gga gaa att att aac agc agg ata caa aga act ggc gac ggg act cat    960
Gly Glu Ile Ile Asn Ser Arg Ile Gln Arg Thr Gly Asp Gly Thr His
305                 310                 315                 320 tca agg agc aag aaa aat ata tct acg caa gat gag taa                999
Ser Arg Ser Lys Lys Asn Ile Ser Thr Gln Asp Glu
                325                 330
```

<210> SEQ ID NO 2
<211> LENGTH: 332
<212> TYPE: PRT
<213> ORGANISM: Epiphyas postvittana

<400> SEQUENCE: 2

```
Met Ala Pro Asn Val Glu Glu Ile Glu Thr Asp Leu Thr Glu Thr Glu
  1               5                  10                  15

Glu Lys Trp Glu Lys Leu Val Ala Pro Gln Ala Ala Pro Arg Lys His
             20                  25                  30

Glu Ile Leu Tyr Thr Asn Leu Leu Ile Phe Gly Tyr Gly His Leu Ala
         35                  40                  45

Gly Leu Tyr Gly Leu Tyr Leu Cys Phe Thr Ser Ala Arg Leu Gln Thr
     50                  55                  60

Ile Ile Leu Ala Phe Ile Leu His Ala Met Ala Ile Leu Gly Ile Thr
 65                  70                  75                  80

Ala Gly Ala His Arg Leu Trp Thr His Arg Ser Tyr Lys Ala Thr Met
                 85                  90                  95

Pro Leu Gln Ile Ile Leu Ile Ile Phe Asn Ser Leu Ser Phe Gln Asn
            100                 105                 110

Ser Ala Ile Asn Trp Val Arg Asp His Arg Ser His His Lys Tyr Cys
        115                 120                 125

Asp Thr Asp Ala Asp Pro His Asn Ala Ala Arg Gly Leu Phe Tyr Ser
    130                 135                 140

His Ile Gly Trp Leu Leu Val Lys Lys His Pro Glu Val Lys Lys Arg
145                 150                 155                 160

Gly Lys Met Thr Asp Met Ser Asp Val Tyr Arg Asn Pro Val Leu Arg
                165                 170                 175

Phe Gln Lys Lys Tyr Ala Val Pro Phe Ile Gly Thr Ile Cys Phe Val
            180                 185                 190

Leu Pro Thr Ile Ile Pro Met Tyr Phe Trp Gly Glu Ser Leu Asn Asn
        195                 200                 205

Ala Trp His Ile Thr Leu Leu Arg Tyr Ile Phe Ser Met His Thr Ile
    210                 215                 220

Phe Leu Val Asn Ser Val Ala His Leu Trp Gly Asn Arg Pro Tyr Asp
225                 230                 235                 240

Lys Asn Ile Leu Pro Ala Asp Asn Arg Thr Leu Ser Ile Ala Thr Leu
                245                 250                 255

Gly Glu Ala Ser His Asn Tyr His His Thr Phe Pro Trp Asp Tyr Arg
            260                 265                 270
```

-continued

```
Ser Thr Glu Leu Gly Tyr Leu Pro Thr Asn Phe Thr Thr Asn Phe Ile
            275                 280                 285

Asp Phe Phe Ala Trp Ile Gly Trp Ala Tyr Asp Leu Lys Thr Thr Ser
        290                 295                 300

Gly Glu Ile Ile Asn Ser Arg Ile Gln Arg Thr Gly Asp Gly Thr His
305                 310                 315                 320

Ser Arg Ser Lys Lys Asn Ile Ser Thr Gln Asp Glu
                325                 330

<210> SEQ ID NO 3
<211> LENGTH: 990
<212> TYPE: DNA
<213> ORGANISM: Ostrinia nubilalis
<220> FEATURE:
<221> NAME/KEY: CDS
<222> LOCATION: (1)..(987)
<223> OTHER INFORMATION: Acyl-CoA E/Z11 desaturase

<400> SEQUENCE: 3 atg gtt cca tac gct acc aca gca gat gga cat cca gaa aaa gat gag      48
Met Val Pro Tyr Ala Thr Thr Ala Asp Gly His Pro Glu Lys Asp Glu
 1               5                  10                  15 tgc ttt gaa gat aat gaa atc aaa tcg aat tcc ttg ccg aaa ctg gaa      96
Cys Phe Glu Asp Asn Glu Ile Lys Ser Asn Ser Leu Pro Lys Leu Glu
                20                  25                  30 ata cta tac ttc aac gtt atg aca ttc acg ttc tta cat cta tct gcg     144
Ile Leu Tyr Phe Asn Val Met Thr Phe Thr Phe Leu His Leu Ser Ala
            35                  40                  45 ctt tat ggg ctg tat ttg gga ttt aca tca gtt aaa tgg gca act ata     192
Leu Tyr Gly Leu Tyr Leu Gly Phe Thr Ser Val Lys Trp Ala Thr Ile
        50                  55                  60 gga ctt gga att ata ttt tat ttt ttt gct gag att gga atc act gct     240
Gly Leu Gly Ile Ile Phe Tyr Phe Phe Ala Glu Ile Gly Ile Thr Ala
 65                  70                  75                  80 ggt gcc cat aga tta tgg agc cac aga agc tac aaa gcg aaa ctc ccc     288
Gly Ala His Arg Leu Trp Ser His Arg Ser Tyr Lys Ala Lys Leu Pro
                 85                  90                  95 ctg gaa ata ctt ctc atg gtg ttt aac agc atg gca ttt caa aat act     336
Leu Glu Ile Leu Leu Met Val Phe Asn Ser Met Ala Phe Gln Asn Thr
            100                 105                 110 gcg ctc tcg tgg gcc aga gac cat cgt gtg cac cat aaa tgt cct gac     384
Ala Leu Ser Trp Ala Arg Asp His Arg Val His His Lys Cys Pro Asp
        115                 120                 125 acc aat ggt gat cct cac aat gcg aat cga gga ttc ttc tat tca cat     432
Thr Asn Gly Asp Pro His Asn Ala Asn Arg Gly Phe Phe Tyr Ser His
    130                 135                 140 gta gga tgg cta atg acc aaa aaa tct gat gaa gtc atc aaa cag gga     480
Val Gly Trp Leu Met Thr Lys Lys Ser Asp Glu Val Ile Lys Gln Gly
145                 150                 155                 160 aaa ttg tgt gat gtg gct gat tta tat agt aac cct gtg tta cgt ttc     528
Lys Leu Cys Asp Val Ala Asp Leu Tyr Ser Asn Pro Val Leu Arg Phe
                165                 170                 175 cag aaa aaa tac gca gtg ccg ttt att gga acg ctt tgt ttc gtt ctc     576
Gln Lys Lys Tyr Ala Val Pro Phe Ile Gly Thr Leu Cys Phe Val Leu
            180                 185                 190 ccg act ctt atc ccg atg tac ttc tgg ggc gaa act tta aac aat gcc     624
Pro Thr Leu Ile Pro Met Tyr Phe Trp Gly Glu Thr Leu Asn Asn Ala
        195                 200                 205 tgg cat ttt aac atg ttt cgt tac gtc att aac ctt aac gca acg ttc     672
Trp His Phe Asn Met Phe Arg Tyr Val Ile Asn Leu Asn Ala Thr Phe
```

-continued

```
            210                 215                 220
tgc gtc aac agc gtc gtc cat aag tgg ggc tac aag ccg tac gac aaa      720
Cys Val Asn Ser Val Val His Lys Trp Gly Tyr Lys Pro Tyr Asp Lys
225                 230                 235                 240 aat att tgt ccg aca caa aac gtt ctt ctg aat ctt gct gtg ctt ggc      768
Asn Ile Cys Pro Thr Gln Asn Val Leu Leu Asn Leu Ala Val Leu Gly
                245                 250                 255 gaa gcg ttc cac aac tac cac cat gtg ttc cca tgg gac tac agg gcg      816
Glu Ala Phe His Asn Tyr His His Val Phe Pro Trp Asp Tyr Arg Ala
            260                 265                 270 gcg gaa tta ggc aac caa aaa atg aac ccc acg act ctg ttc ata gac      864
Ala Glu Leu Gly Asn Gln Lys Met Asn Pro Thr Thr Leu Phe Ile Asp
                275                 280                 285 ttc ttc gct tgg att gga tgg gct tat gat ctc aag aca gcg tct aaa      912
Phe Phe Ala Trp Ile Gly Trp Ala Tyr Asp Leu Lys Thr Ala Ser Lys
            290                 295                 300 gaa atg ata aag agt agg tcg gag aga act ggc gac ggc acg gac tta      960
Glu Met Ile Lys Ser Arg Ser Glu Arg Thr Gly Asp Gly Thr Asp Leu
305                 310                 315                 320 tgg ggt cac agt gcc gat aaa cta aaa taa                              990
Trp Gly His Ser Ala Asp Lys Leu Lys
                325

<210> SEQ ID NO 4
<211> LENGTH: 329
<212> TYPE: PRT
<213> ORGANISM: Ostrinia nubilalis

<400> SEQUENCE: 4

Met Val Pro Tyr Ala Thr Thr Ala Asp Gly His Pro Glu Lys Asp Glu
1               5                   10                  15

Cys Phe Glu Asp Asn Glu Ile Lys Ser Asn Ser Leu Pro Lys Leu Glu
                20                  25                  30

Ile Leu Tyr Phe Asn Val Met Thr Phe Thr Phe Leu His Leu Ser Ala
            35                  40                  45

Leu Tyr Gly Leu Tyr Leu Gly Phe Thr Ser Val Lys Trp Ala Thr Ile
        50                  55                  60

Gly Leu Gly Ile Ile Phe Tyr Phe Phe Ala Glu Ile Gly Ile Thr Ala
65                  70                  75                  80

Gly Ala His Arg Leu Trp Ser His Arg Ser Tyr Lys Ala Lys Leu Pro
                85                  90                  95

Leu Glu Ile Leu Leu Met Val Phe Asn Ser Met Ala Phe Gln Asn Thr
            100                 105                 110

Ala Leu Ser Trp Ala Arg Asp His Arg Val His His Lys Cys Pro Asp
        115                 120                 125

Thr Asn Gly Asp Pro His Asn Ala Asn Arg Gly Phe Phe Tyr Ser His
130                 135                 140

Val Gly Trp Leu Met Thr Lys Lys Ser Asp Glu Val Ile Lys Gln Gly
145                 150                 155                 160

Lys Leu Cys Asp Val Ala Asp Leu Tyr Ser Asn Pro Val Leu Arg Phe
                165                 170                 175

Gln Lys Lys Tyr Ala Val Pro Phe Ile Gly Thr Leu Cys Phe Val Leu
            180                 185                 190

Pro Thr Leu Ile Pro Met Tyr Phe Trp Gly Glu Thr Leu Asn Asn Ala
        195                 200                 205

Trp His Phe Asn Met Phe Arg Tyr Val Ile Asn Leu Asn Ala Thr Phe
210                 215                 220
```

```
Cys Val Asn Ser Val Val His Lys Trp Gly Tyr Lys Pro Tyr Asp Lys
225                 230                 235                 240

Asn Ile Cys Pro Thr Gln Asn Val Leu Leu Asn Leu Ala Val Leu Gly
            245                 250                 255

Glu Ala Phe His Asn Tyr His Val Phe Pro Trp Asp Tyr Arg Ala
                260                 265                 270

Ala Glu Leu Gly Asn Gln Lys Met Asn Pro Thr Thr Leu Phe Ile Asp
            275                 280                 285

Phe Phe Ala Trp Ile Gly Trp Ala Tyr Asp Leu Lys Thr Ala Ser Lys
        290                 295                 300

Glu Met Ile Lys Ser Arg Ser Glu Arg Thr Gly Asp Gly Thr Asp Leu
305                 310                 315                 320

Trp Gly His Ser Ala Asp Lys Leu Lys
                325
```

<210> SEQ ID NO 5
<211> LENGTH: 990
<212> TYPE: DNA
<213> ORGANISM: Ostrinia furnacalis
<220> FEATURE:
<221> NAME/KEY: CDS
<222> LOCATION: (1)..(987)
<223> OTHER INFORMATION: Acyl CoA E/Z11 desaturase

<400> SEQUENCE: 5

```
atg gtt cca tac gct acc aca gca gat gga cat cca gaa aaa gat gag        48
Met Val Pro Tyr Ala Thr Thr Ala Asp Gly His Pro Glu Lys Asp Glu
1               5                   10                  15 tgc ttt gaa gat aat gaa atc aaa tcg aat tcc ttg ccg aaa ctg gaa        96
Cys Phe Glu Asp Asn Glu Ile Lys Ser Asn Ser Leu Pro Lys Leu Glu
                20                  25                  30 ata cta tac ttc aac gtt atg aca ttc acg ttc tta cat cta tct gcg       144
Ile Leu Tyr Phe Asn Val Met Thr Phe Thr Phe Leu His Leu Ser Ala
            35                  40                  45 ctt tat ggg ctg tat ttg gga ttt aca tca gtt aaa tgg gca act ata       192
Leu Tyr Gly Leu Tyr Leu Gly Phe Thr Ser Val Lys Trp Ala Thr Ile
        50                  55                  60 gga ctt gga att ata ttt tat ttt ttt gct gag att gga atc act gct       240
Gly Leu Gly Ile Ile Phe Tyr Phe Phe Ala Glu Ile Gly Ile Thr Ala
65                  70                  75                  80 ggt gcc cat aga cta tgg agc cac aga agc tac aaa gcg aaa ctc ccc       288
Gly Ala His Arg Leu Trp Ser His Arg Ser Tyr Lys Ala Lys Leu Pro
                85                  90                  95 ctg gaa ata ctt ctc atg gtg ttt aac agc atg gca ttt caa aat act       336
Leu Glu Ile Leu Leu Met Val Phe Asn Ser Met Ala Phe Gln Asn Thr
            100                 105                 110 gcg ctc tcg tgg gcc aga gac cat cgt gtg cac cat aaa tgt cct gac       384
Ala Leu Ser Trp Ala Arg Asp His Arg Val His His Lys Cys Pro Asp
        115                 120                 125 acc aat ggt gat cct cac aat gcg aat cga gga ttc ttc tat tcg cac       432
Thr Asn Gly Asp Pro His Asn Ala Asn Arg Gly Phe Phe Tyr Ser His
130                 135                 140 gta gga tgg cta atg acc aag aaa tct gat gaa gtc atc aaa cag gga       480
Val Gly Trp Leu Met Thr Lys Lys Ser Asp Glu Val Ile Lys Gln Gly
145                 150                 155                 160 aaa ttg tgt gat gtg gct gat tta tac agt aac cct gtg tta cgt ttc       528
Lys Leu Cys Asp Val Ala Asp Leu Tyr Ser Asn Pro Val Leu Arg Phe
                165                 170                 175 cag aaa aaa tac gca gtg ccg ttt att gga acg ctt tgt ttc gtt ctc       576
Gln Lys Lys Tyr Ala Val Pro Phe Ile Gly Thr Leu Cys Phe Val Leu
```

```
                Gln Lys Lys Tyr Ala Val Pro Phe Ile Gly Thr Leu Cys Phe Val Leu
                            180                 185                 190 ccg act ctt atc ccg atg tac ttc tgg ggc gaa act tta aac aat gcc        624
Pro Thr Leu Ile Pro Met Tyr Phe Trp Gly Glu Thr Leu Asn Asn Ala
        195                 200                 205 tgg cat ttt aac atg ttt cgt tac gtc att aac cta aac gca acg ttc        672
Trp His Phe Asn Met Phe Arg Tyr Val Ile Asn Leu Asn Ala Thr Phe
    210                 215                 220 tgc gtc aac agc gtc gtc cat aag tgg ggc tac aag ccg tac gac aaa        720
Cys Val Asn Ser Val Val His Lys Trp Gly Tyr Lys Pro Tyr Asp Lys
225                 230                 235                 240 aat att tgt ccg aca caa aac gtt ctt ctg aat ctt gct gtg ctt ggc        768
Asn Ile Cys Pro Thr Gln Asn Val Leu Leu Asn Leu Ala Val Leu Gly
                245                 250                 255 gaa gcg ttc cac aac tac cac cat gtg ttc cca tgg gac tac agg gcg        816
Glu Ala Phe His Asn Tyr His His Val Phe Pro Trp Asp Tyr Arg Ala
            260                 265                 270 gcg gaa tta ggc aac caa aaa atg aac ccc acg act ctg ttc ata gac        864
Ala Glu Leu Gly Asn Gln Lys Met Asn Pro Thr Thr Leu Phe Ile Asp
        275                 280                 285 ttc ttc gct tgg att gga tgg gct tat gat ctc aag aca gca tct aaa        912
Phe Phe Ala Trp Ile Gly Trp Ala Tyr Asp Leu Lys Thr Ala Ser Lys
    290                 295                 300 gaa atg ata aag agt agg tcg gag aga act ggc gac ggc acg gac tta        960
Glu Met Ile Lys Ser Arg Ser Glu Arg Thr Gly Asp Gly Thr Asp Leu
305                 310                 315                 320 tgg ggt cac agt gcc gat aaa cta aaa taa                                990
Trp Gly His Ser Ala Asp Lys Leu Lys
                325

<210> SEQ ID NO 6
<211> LENGTH: 329
<212> TYPE: PRT
<213> ORGANISM: Ostrinia furnacalis

<400> SEQUENCE: 6

Met Val Pro Tyr Ala Thr Thr Ala Asp Gly His Pro Glu Lys Asp Glu
  1               5                  10                  15

Cys Phe Glu Asp Asn Glu Ile Lys Ser Asn Ser Leu Pro Lys Leu Glu
             20                  25                  30

Ile Leu Tyr Phe Asn Val Met Thr Phe Thr Phe Leu His Leu Ser Ala
         35                  40                  45

Leu Tyr Gly Leu Tyr Leu Gly Phe Thr Ser Val Lys Trp Ala Thr Ile
     50                  55                  60

Gly Leu Gly Ile Ile Phe Tyr Phe Phe Ala Glu Ile Gly Ile Thr Ala
 65                  70                  75                  80

Gly Ala His Arg Leu Trp Ser His Arg Ser Tyr Lys Ala Lys Leu Pro
                 85                  90                  95

Leu Glu Ile Leu Leu Met Val Phe Asn Ser Met Ala Phe Gln Asn Thr
            100                 105                 110

Ala Leu Ser Trp Ala Arg Asp His Arg Val His His Lys Cys Pro Asp
        115                 120                 125

Thr Asn Gly Asp Pro His Asn Ala Asn Arg Gly Phe Phe Tyr Ser His
    130                 135                 140

Val Gly Trp Leu Met Thr Lys Lys Ser Asp Glu Val Ile Lys Gln Gly
145                 150                 155                 160

Lys Leu Cys Asp Val Ala Asp Leu Tyr Ser Asn Pro Val Leu Arg Phe
                165                 170                 175
```

```
Gln Lys Lys Tyr Ala Val Pro Phe Ile Gly Thr Leu Cys Phe Val Leu
                180                 185                 190

Pro Thr Leu Ile Pro Met Tyr Phe Trp Gly Glu Thr Leu Asn Asn Ala
            195                 200                 205

Trp His Phe Asn Met Phe Arg Tyr Val Ile Asn Leu Asn Ala Thr Phe
        210                 215                 220

Cys Val Asn Ser Val Val His Lys Trp Gly Tyr Lys Pro Tyr Asp Lys
225                 230                 235                 240

Asn Ile Cys Pro Thr Gln Asn Val Leu Leu Asn Leu Ala Val Leu Gly
                245                 250                 255

Glu Ala Phe His Asn Tyr His Val Phe Pro Trp Asp Tyr Arg Ala
            260                 265                 270

Ala Glu Leu Gly Asn Gln Lys Met Asn Pro Thr Thr Leu Phe Ile Asp
            275                 280                 285

Phe Phe Ala Trp Ile Gly Trp Ala Tyr Asp Leu Lys Thr Ala Ser Lys
        290                 295                 300

Glu Met Ile Lys Ser Arg Ser Glu Arg Thr Gly Asp Gly Thr Asp Leu
305                 310                 315                 320

Trp Gly His Ser Ala Asp Lys Leu Lys
                325

<210> SEQ ID NO 7
<211> LENGTH: 1017
<212> TYPE: DNA
<213> ORGANISM: Helicoverpa zea
<220> FEATURE:
<221> NAME/KEY: CDS
<222> LOCATION: (1)..(1014)
<223> OTHER INFORMATION: Acyl CoA delta-11 desaturase

<400> SEQUENCE: 7 atg gcc caa agc tat caa tca act acg gtt ttg agt gag gag aaa gaa    48
Met Ala Gln Ser Tyr Gln Ser Thr Thr Val Leu Ser Glu Glu Lys Glu
  1               5                  10                  15 cta aca ctg caa cat ttg gtg ccc caa gca tcg ccc agg aag tat caa    96
Leu Thr Leu Gln His Leu Val Pro Gln Ala Ser Pro Arg Lys Tyr Gln
             20                  25                  30 ata gtg tat ccg aac ctc att acg ttt ggt tac tgg cac ata gcc gga   144
Ile Val Tyr Pro Asn Leu Ile Thr Phe Gly Tyr Trp His Ile Ala Gly
         35                  40                  45 ctt tat ggc ctt tac ttg tgc ttc act tct gct aaa tgg gct acg att   192
Leu Tyr Gly Leu Tyr Leu Cys Phe Thr Ser Ala Lys Trp Ala Thr Ile
     50                  55                  60 tta ttc agc tac atc ctc ttc gtg tta gca gaa ata gga atc acg gct   240
Leu Phe Ser Tyr Ile Leu Phe Val Leu Ala Glu Ile Gly Ile Thr Ala
 65                  70                  75                  80 ggc gct cac aga ctc tgg gcc cac aaa act tac aaa gcg aaa cta cca   288
Gly Ala His Arg Leu Trp Ala His Lys Thr Tyr Lys Ala Lys Leu Pro
                 85                  90                  95 tta gaa ata ctc tta atg gta ttc aac tcc atc gct ttt caa aac tca   336
Leu Glu Ile Leu Leu Met Val Phe Asn Ser Ile Ala Phe Gln Asn Ser
            100                 105                 110 gcc att gac tgg gtg agg gac cac cga ctc cac cat aag tat agc gat   384
Ala Ile Asp Trp Val Arg Asp His Arg Leu His His Lys Tyr Ser Asp
        115                 120                 125 aca gat gct gat ccc cac aat gcc agc cga ggg ttc ttt tat tcc cat   432
Thr Asp Ala Asp Pro His Asn Ala Ser Arg Gly Phe Phe Tyr Ser His
    130                 135                 140
```

```
gta gga tgg cta ctt gtg aga aaa cat cct gaa gtc aaa aag cga ggg      480
Val Gly Trp Leu Leu Val Arg Lys His Pro Glu Val Lys Lys Arg Gly
145                 150                 155                 160 aaa gaa ctc aat atg tcc gat att tac aac aat cct gtc ctg cgg ttt      528
Lys Glu Leu Asn Met Ser Asp Ile Tyr Asn Asn Pro Val Leu Arg Phe
                165                 170                 175 cag aaa aaa tac gcc ata ccc ttc att ggg gct gtt tgt ttc gcc tta      576
Gln Lys Lys Tyr Ala Ile Pro Phe Ile Gly Ala Val Cys Phe Ala Leu
            180                 185                 190 cct aca atg ata cct gtt tac ttc tgg gga gaa acc tgg tcc aat gct      624
Pro Thr Met Ile Pro Val Tyr Phe Trp Gly Glu Thr Trp Ser Asn Ala
        195                 200                 205 tgg cat atc acc atg ctt cgc tac atc atg aac ctc aat gtc acc ttt      672
Trp His Ile Thr Met Leu Arg Tyr Ile Met Asn Leu Asn Val Thr Phe
    210                 215                 220 ttg gta aac agc gct gct cat ata tgg gga aac aag cct tat gac gca      720
Leu Val Asn Ser Ala Ala His Ile Trp Gly Asn Lys Pro Tyr Asp Ala
225                 230                 235                 240 aaa ata tta cct gca caa aat gta gct gtg tcg gtc gcc act ggt gga      768
Lys Ile Leu Pro Ala Gln Asn Val Ala Val Ser Val Ala Thr Gly Gly
                245                 250                 255 gaa ggt ttc cat aat tac cac cat gtc ttc ccc tgg gat tat cga gca      816
Glu Gly Phe His Asn Tyr His His Val Phe Pro Trp Asp Tyr Arg Ala
            260                 265                 270 gcg gaa ctc ggt aac aat agc ctc aat ctg acg act aaa ttc ata gat      864
Ala Glu Leu Gly Asn Asn Ser Leu Asn Leu Thr Thr Lys Phe Ile Asp
        275                 280                 285 tta ttc gca gca atc gga tgg gca tat gat ctg aag acg gtt tcg gag      912
Leu Phe Ala Ala Ile Gly Trp Ala Tyr Asp Leu Lys Thr Val Ser Glu
    290                 295                 300 gat atg ata aaa caa agg att aaa cgc act gga gat gga acg gat ctt      960
Asp Met Ile Lys Gln Arg Ile Lys Arg Thr Gly Asp Gly Thr Asp Leu
305                 310                 315                 320 tgg gga cac gaa caa aac tgt gat gaa gtg tgg gat gta aaa gat aaa     1008
Trp Gly His Glu Gln Asn Cys Asp Glu Val Trp Asp Val Lys Asp Lys
                325                 330                 335 tca agt taa                                                         1017
Ser Ser
```

<210> SEQ ID NO 8
<211> LENGTH: 338
<212> TYPE: PRT
<213> ORGANISM: Helicoverpa zea

<400> SEQUENCE: 8

```
Met Ala Gln Ser Tyr Gln Ser Thr Thr Val Leu Ser Glu Glu Lys Glu
  1               5                  10                  15

Leu Thr Leu Gln His Leu Val Pro Gln Ala Ser Pro Arg Lys Tyr Gln
             20                  25                  30

Ile Val Tyr Pro Asn Leu Ile Thr Phe Gly Tyr Trp His Ile Ala Gly
         35                  40                  45

Leu Tyr Gly Leu Tyr Leu Cys Phe Thr Ser Ala Lys Trp Ala Thr Ile
     50                  55                  60

Leu Phe Ser Tyr Ile Leu Phe Val Leu Ala Glu Ile Gly Ile Thr Ala
 65                  70                  75                  80

Gly Ala His Arg Leu Trp Ala His Lys Thr Tyr Lys Ala Lys Leu Pro
                 85                  90                  95

Leu Glu Ile Leu Leu Met Val Phe Asn Ser Ile Ala Phe Gln Asn Ser
            100                 105                 110
```

```
Ala Ile Asp Trp Val Arg Asp His Arg Leu His His Lys Tyr Ser Asp
        115                 120                 125

Thr Asp Ala Asp Pro His Asn Ala Ser Arg Gly Phe Phe Tyr Ser His
    130                 135                 140

Val Gly Trp Leu Leu Val Arg Lys His Pro Glu Val Lys Lys Arg Gly
145                 150                 155                 160

Lys Glu Leu Asn Met Ser Asp Ile Tyr Asn Asn Pro Val Leu Arg Phe
                165                 170                 175

Gln Lys Lys Tyr Ala Ile Pro Phe Ile Gly Ala Val Cys Phe Ala Leu
            180                 185                 190

Pro Thr Met Ile Pro Val Tyr Phe Trp Gly Glu Thr Trp Ser Asn Ala
        195                 200                 205

Trp His Ile Thr Met Leu Arg Tyr Ile Met Asn Leu Asn Val Thr Phe
    210                 215                 220

Leu Val Asn Ser Ala Ala His Ile Trp Gly Asn Lys Pro Tyr Asp Ala
225                 230                 235                 240

Lys Ile Leu Pro Ala Gln Asn Val Ala Val Ser Val Ala Thr Gly Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Leu Thr Thr Lys Phe Ile Asp
        275                 280                 285

Leu Phe Ala Ala Ile Gly Trp Ala Tyr Asp Leu Lys Thr Val Ser Glu
    290                 295                 300

Asp Met Ile Lys Gln Arg Ile Lys Arg Thr Gly Asp Gly Thr Asp Leu
305                 310                 315                 320

Trp Gly His Glu Gln Asn Cys Asp Glu Val Trp Asp Val Lys Asp Lys
                325                 330                 335

Ser Ser

<210> SEQ ID NO 9
<211> LENGTH: 1050
<212> TYPE: DNA
<213> ORGANISM: Trichoplusia ni
<220> FEATURE:
<221> NAME/KEY: CDS
<222> LOCATION: (1)..(1047)
<223> OTHER INFORMATION: Acyl CoA delta11 desaturase

<400> SEQUENCE: 9 atg gct gtg atg gct caa aca gta caa gaa acg gct aca gtg ttg gaa      48
Met Ala Val Met Ala Gln Thr Val Gln Glu Thr Ala Thr Val Leu Glu
1               5                   10                  15 gag gaa gct cgc aca gtg act ctt gtg gct cca aag aca acg cca agg      96
Glu Glu Ala Arg Thr Val Thr Leu Val Ala Pro Lys Thr Thr Pro Arg
            20                  25                  30 aaa tat aaa tat ata tac acc aac ttt ctt aca ttt tca tat gcg cat     144
Lys Tyr Lys Tyr Ile Tyr Thr Asn Phe Leu Thr Phe Ser Tyr Ala His
        35                  40                  45 tta gct gca tta tac gga ctt tat ttg tgc ttc acc tct gcg aaa tgg     192
Leu Ala Ala Leu Tyr Gly Leu Tyr Leu Cys Phe Thr Ser Ala Lys Trp
    50                  55                  60 gaa aca ttg cta ttc tct ttc gta ctc ttc cac atg tca aat ata ggc     240
Glu Thr Leu Leu Phe Ser Phe Val Leu Phe His Met Ser Asn Ile Gly
65                  70                  75                  80 atc acc gca ggg gct cac cga ctc tgg act cac aag act ttc aaa gcc     288
Ile Thr Ala Gly Ala His Arg Leu Trp Thr His Lys Thr Phe Lys Ala
```

|  |  |  |  |  |  |  |  | 85 |  |  |  |  | 90 |  |  |  |  | 95 |  |  |  |
|---|---|---|---|---|---|---|---|---|---|---|---|---|---|---|---|---|---|---|---|---|---|

```
aaa ttg cct ttg gaa att gtc ctc atg ata ttc aac tct tta gcc ttt       336
Lys Leu Pro Leu Glu Ile Val Leu Met Ile Phe Asn Ser Leu Ala Phe
            100                 105                 110 caa aac acg gct att aca tgg gct aga gaa cat cgg cta cat cac aaa       384
Gln Asn Thr Ala Ile Thr Trp Ala Arg Glu His Arg Leu His His Lys
        115                 120                 125 tac agc gat act gat gct gat ccc cac aat gcg tca aga ggg ttc ttc       432
Tyr Ser Asp Thr Asp Ala Asp Pro His Asn Ala Ser Arg Gly Phe Phe
    130                 135                 140 tac tcg cat gtt ggc tgg cta tta gta aaa aaa cat ccc gat gtc ctg       480
Tyr Ser His Val Gly Trp Leu Leu Val Lys Lys His Pro Asp Val Leu
145                 150                 155                 160 aaa tat gga aaa act ata gac atg tcg gat gta tac aat aat cct gtg       528
Lys Tyr Gly Lys Thr Ile Asp Met Ser Asp Val Tyr Asn Asn Pro Val
                165                 170                 175 tta aaa ttt cag aaa aag tac gca gta ccc tta att gga aca gtt tgt       576
Leu Lys Phe Gln Lys Lys Tyr Ala Val Pro Leu Ile Gly Thr Val Cys
            180                 185                 190 ttt gct ctt cca act ttg att cca gtc tac tgt tgg ggc gaa tcg tgg       624
Phe Ala Leu Pro Thr Leu Ile Pro Val Tyr Cys Trp Gly Glu Ser Trp
        195                 200                 205 aac aac gct tgg cac ata gcc tta ttt cga tac ata ttc aat ctt aac       672
Asn Asn Ala Trp His Ile Ala Leu Phe Arg Tyr Ile Phe Asn Leu Asn
    210                 215                 220 gtg act ttc cta gtc aac agt gct gcg cat atc tgg ggg aat aag cct       720
Val Thr Phe Leu Val Asn Ser Ala Ala His Ile Trp Gly Asn Lys Pro
225                 230                 235                 240 tat gat aaa agc atc ttg ccc gct caa aac ctg ctg gtt tcc ttc cta       768
Tyr Asp Lys Ser Ile Leu Pro Ala Gln Asn Leu Leu Val Ser Phe Leu
                245                 250                 255 gca agt gga gaa ggc ttc cat aat tac cat cac gtc ttt cca tgg gat       816
Ala Ser Gly Glu Gly Phe His Asn Tyr His His Val Phe Pro Trp Asp
            260                 265                 270 tac cgc aca gca gaa tta ggg aat aac ttc ctg aat ttg acg acg ctg       864
Tyr Arg Thr Ala Glu Leu Gly Asn Asn Phe Leu Asn Leu Thr Thr Leu
        275                 280                 285 ttc att gat ttt tgt gcc tgg ttt gga tgg gct tat gac ttg aag tct       912
Phe Ile Asp Phe Cys Ala Trp Phe Gly Trp Ala Tyr Asp Leu Lys Ser
    290                 295                 300 gta tca gag gat att ata aaa cag aga gct aaa cga aca ggt gac ggt       960
Val Ser Glu Asp Ile Ile Lys Gln Arg Ala Lys Arg Thr Gly Asp Gly
305                 310                 315                 320 tct tca ggg gtc att tgg gga tgg gac gac aaa gac atg gac cgc gat      1008
Ser Ser Gly Val Ile Trp Gly Trp Asp Asp Lys Asp Met Asp Arg Asp
                325                 330                 335 ata aaa tct aaa gct aac att ttt tat gct aaa aag gaa tga              1050
Ile Lys Ser Lys Ala Asn Ile Phe Tyr Ala Lys Lys Glu
            340                 345

<210> SEQ ID NO 10
<211> LENGTH: 349
<212> TYPE: PRT
<213> ORGANISM: Trichoplusia ni

<400> SEQUENCE: 10

Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
            20                  25                  30
```

-continued

```
Lys Tyr Lys Tyr Ile Tyr Thr Asn Phe Leu Thr Phe Ser Tyr Ala His
         35                  40                  45

Leu Ala Ala Leu Tyr Gly Leu Tyr Leu Cys Phe Thr Ser Ala Lys Trp
 50                  55                  60

Glu Thr Leu Leu Phe Ser Phe Val Leu Phe His Met Ser Asn Ile Gly
 65                  70                  75                  80

Ile Thr Ala Gly Ala His Arg Leu Trp Thr His Lys Thr Phe Lys Ala
                 85                  90                  95

Lys Leu Pro Leu Glu Ile Val Leu Met Ile Phe Asn Ser Leu Ala Phe
                100                 105                 110

Gln Asn Thr Ala Ile Thr Trp Ala Arg Glu His Arg Leu His His Lys
            115                 120                 125

Tyr Ser Asp Thr Asp Ala Asp Pro His Asn Ala Ser Arg Gly Phe Phe
        130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
                165                 170                 175

Leu Lys Phe Gln Lys Lys Tyr Ala Val Pro Leu Ile Gly Thr Val Cys
                180                 185                 190

Phe Ala Leu Pro Thr Leu Ile Pro Val Tyr Cys Trp Gly Glu Ser Trp
            195                 200                 205

Asn Asn Ala Trp His Ile Ala Leu Phe Arg Tyr Ile Phe Asn Leu Asn
        210                 215                 220

Val Thr Phe Leu Val Asn Ser Ala Ala His Ile Trp Gly Asn Lys Pro
225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
                260                 265                 270

Tyr Arg Thr Ala Glu Leu Gly Asn Asn Phe Leu Asn Leu Thr Thr Leu
            275                 280                 285

Phe Ile Asp Phe Cys Ala Trp Phe Gly Trp Ala Tyr Asp Leu Lys Ser
290                 295                 300

Val Ser Glu Asp Ile Ile Lys Gln Arg Ala Lys Arg Thr Gly Asp Gly
305                 310                 315                 320

Ser Ser Gly Val Ile Trp Gly Trp Asp Lys Asp Met Asp Arg Asp
                325                 330                 335

Ile Lys Ser Lys Ala Asn Ile Phe Tyr Ala Lys Lys Glu
            340                 345
```

<210> SEQ ID NO 11
<211> LENGTH: 990
<212> TYPE: DNA
<213> ORGANISM: Argyrotaenia velutinana
<220> FEATURE:
<221> NAME/KEY: CDS
<222> LOCATION: (1)..(987)
<223> OTHER INFORMATION: Acyl CoA delta11 desaturase

<400> SEQUENCE: 11

```
atg gct cca aat gcg gaa gat att gaa acg aat atg cca gaa act gaa      48
Met Ala Pro Asn Ala Glu Asp Ile Glu Thr Asn Met Pro Glu Thr Glu
 1               5                  10                  15 gag aac tgg gaa aca tta gta gca cct caa gca gcg cct aga aaa tat      96
Glu Asn Trp Glu Thr Leu Val Ala Pro Gln Ala Ala Pro Arg Lys Tyr
```

```
                    20                  25                  30
caa att gtg tat aaa agc ctc tta act ttt ggc tac gga cac ctc gct    144
Gln Ile Val Tyr Lys Ser Leu Leu Thr Phe Gly Tyr Gly His Leu Ala
             35                  40                  45 ggt cta tat ggt tta tat ttg tgc ttt act tcc gct aaa tgg caa act    192
Gly Leu Tyr Gly Leu Tyr Leu Cys Phe Thr Ser Ala Lys Trp Gln Thr
 50                  55                  60 att gga ctt gct atc atc ctc cac gcg atg gca atc ttg ggc atc aca    240
Ile Gly Leu Ala Ile Ile Leu His Ala Met Ala Ile Leu Gly Ile Thr
 65                  70                  75                  80 gca ggc gct cac cga ctc tgg aca cac aga gca tac aaa gcg acg gtg    288
Ala Gly Ala His Arg Leu Trp Thr His Arg Ala Tyr Lys Ala Thr Val
                 85                  90                  95 ccc ctc caa atc atc ctc ata atc ttc aac tcc ctg tcg ttc caa aac    336
Pro Leu Gln Ile Ile Leu Ile Ile Phe Asn Ser Leu Ser Phe Gln Asn
            100                 105                 110 agc gcc ttt act tgg atc aga gac cac aga ctc cac cac aag tat agt    384
Ser Ala Phe Thr Trp Ile Arg Asp His Arg Leu His His Lys Tyr Ser
            115                 120                 125 gac aca gac ggg gat ccc cac aat gca acc aga ggg ttc ttt tac tct    432
Asp Thr Asp Gly Asp Pro His Asn Ala Thr Arg Gly Phe Phe Tyr Ser
130                 135                 140 cat atc gga tgg ctg ttg gtg agg aaa cac cct gaa gtc atg aag agg    480
His Ile Gly Trp Leu Leu Val Arg Lys His Pro Glu Val Met Lys Arg
145                 150                 155                 160 gga aga atg acc gag atg tcg gat att tac agc aat cct atc ata atg    528
Gly Arg Met Thr Glu Met Ser Asp Ile Tyr Ser Asn Pro Ile Ile Met
                165                 170                 175 ttt caa aaa aac tac gct ata cct ttc ata ggc acg gtg tgt ttc gta    576
Phe Gln Lys Asn Tyr Ala Ile Pro Phe Ile Gly Thr Val Cys Phe Val
            180                 185                 190 ctt ccc aca ata ata ccc atg tac ttc tgg gga gag acg ttg aac aac    624
Leu Pro Thr Ile Ile Pro Met Tyr Phe Trp Gly Glu Thr Leu Asn Asn
            195                 200                 205 gct tgg cat ata acg gtg ctg cgc tac att ttt agc ctc aac tgc ata    672
Ala Trp His Ile Thr Val Leu Arg Tyr Ile Phe Ser Leu Asn Cys Ile
210                 215                 220 ttc ctc gtg aac agc gca gcc cat tta tac ggc tac aag cca tac gac    720
Phe Leu Val Asn Ser Ala Ala His Leu Tyr Gly Tyr Lys Pro Tyr Asp
225                 230                 235                 240 aag aac att ttg cca gcg gaa aac aaa gca gct tca atc gca tct ttt    768
Lys Asn Ile Leu Pro Ala Glu Asn Lys Ala Ala Ser Ile Ala Ser Phe
                245                 250                 255 gga gaa gcc ttc cat aac tat cat cat gtg ttt cct tgg gac tac aga    816
Gly Glu Ala Phe His Asn Tyr His His Val Phe Pro Trp Asp Tyr Arg
            260                 265                 270 gct tct gaa cta ggt aat ata aca atg aat tgg aca ata tat ttc att    864
Ala Ser Glu Leu Gly Asn Ile Thr Met Asn Trp Thr Ile Tyr Phe Ile
            275                 280                 285 gat ttc ttc gct tgg atc ggc tgg gct tac gac ttg aaa act gca tcg    912
Asp Phe Phe Ala Trp Ile Gly Trp Ala Tyr Asp Leu Lys Thr Ala Ser
290                 295                 300 gat gag act att aaa agc aga ata aaa aga act ggc gat ggt act gac    960
Asp Glu Thr Ile Lys Ser Arg Ile Lys Arg Thr Gly Asp Gly Thr Asp
305                 310                 315                 320 ttc tcg ggc cag caa ata tac gca aga tga                            990
Phe Ser Gly Gln Gln Ile Tyr Ala Arg
                325
```

<210> SEQ ID NO 12
<211> LENGTH: 329
<212> TYPE: PRT
<213> ORGANISM: Argyrotaenia velutinana

<400> SEQUENCE: 12

```
Met Ala Pro Asn Ala Glu Asp Ile Glu Thr Asn Met Pro Glu Thr Glu
1               5                   10                  15

Glu Asn Trp Glu Thr Leu Val Ala Pro Gln Ala Ala Pro Arg Lys Tyr
            20                  25                  30

Gln Ile Val Tyr Lys Ser Leu Leu Thr Phe Gly Tyr Gly His Leu Ala
        35                  40                  45

Gly Leu Tyr Gly Leu Tyr Leu Cys Phe Thr Ser Ala Lys Trp Gln Thr
    50                  55                  60

Ile Gly Leu Ala Ile Ile Leu His Ala Met Ala Ile Leu Gly Ile Thr
65                  70                  75                  80

Ala Gly Ala His Arg Leu Trp Thr His Arg Ala Tyr Lys Ala Thr Val
                85                  90                  95

Pro Leu Gln Ile Ile Leu Ile Ile Phe Asn Ser Leu Ser Phe Gln Asn
            100                 105                 110

Ser Ala Phe Thr Trp Ile Arg Asp His Arg Leu His His Lys Tyr Ser
        115                 120                 125

Asp Thr Asp Gly Asp Pro His Asn Ala Thr Arg Gly Phe Phe Tyr Ser
    130                 135                 140

His Ile Gly Trp Leu Leu Val Arg Lys His Pro Glu Val Met Lys Arg
145                 150                 155                 160

Gly Arg Met Thr Glu Met Ser Asp Ile Tyr Ser Asn Pro Ile Ile Met
                165                 170                 175

Phe Gln Lys Asn Tyr Ala Ile Pro Phe Ile Gly Thr Val Cys Phe Val
            180                 185                 190

Leu Pro Thr Ile Ile Pro Met Tyr Phe Trp Gly Glu Thr Leu Asn Asn
        195                 200                 205

Ala Trp His Ile Thr Val Leu Arg Tyr Ile Phe Ser Leu Asn Cys Ile
    210                 215                 220

Phe Leu Val Asn Ser Ala Ala His Leu Tyr Gly Tyr Lys Pro Tyr Asp
225                 230                 235                 240

Lys Asn Ile Leu Pro Ala Glu Asn Lys Ala Ala Ser Ile Ala Ser Phe
                245                 250                 255

Gly Glu Ala Phe His Asn Tyr His His Val Phe Pro Trp Asp Tyr Arg
            260                 265                 270

Ala Ser Glu Leu Gly Asn Ile Thr Met Asn Trp Thr Ile Tyr Phe Ile
        275                 280                 285

Asp Phe Phe Ala Trp Ile Gly Trp Ala Tyr Asp Leu Lys Thr Ala Ser
    290                 295                 300

Asp Glu Thr Ile Lys Ser Arg Ile Lys Arg Thr Gly Asp Gly Thr Asp
305                 310                 315                 320

Phe Ser Gly Gln Gln Ile Tyr Ala Arg
                325
```

<210> SEQ ID NO 13
<211> LENGTH: 1071
<212> TYPE: DNA
<213> ORGANISM: Planotortrix octo
<220> FEATURE:
<221> NAME/KEY: CDS
<222> LOCATION: (1)..(1068)
<223> OTHER INFORMATION: Acyl CoA Z10 desaturase

<400> SEQUENCE: 13

```
atg cca cca aat tca gag gaa aca gtg cta tgt gaa aag gaa gac cac      48
Met Pro Pro Asn Ser Glu Glu Thr Val Leu Cys Glu Lys Glu Asp His
 1               5                  10                  15 gag aag ctg gtg gcg cca caa gcg gct acc agg aaa cat gag ctg gca      96
Glu Lys Leu Val Ala Pro Gln Ala Ala Thr Arg Lys His Glu Leu Ala
                 20                  25                  30 ata gtg ccc atc tca ctc ttc act tac tgg cac gtc gct ggc ttg tac     144
Ile Val Pro Ile Ser Leu Phe Thr Tyr Trp His Val Ala Gly Leu Tyr
             35                  40                  45 ggg ctg tat ctc atc ttt gct gaa gcg aaa tgg cag acc gta gtg ttc     192
Gly Leu Tyr Leu Ile Phe Ala Glu Ala Lys Trp Gln Thr Val Val Phe
         50                  55                  60 act ctc ttc acc tac aac gcc ggc att ctg ggc atc act gca ggg tcc     240
Thr Leu Phe Thr Tyr Asn Ala Gly Ile Leu Gly Ile Thr Ala Gly Ser
 65                  70                  75                  80 cac cgc ctc tgg gcc cac aag aca tac aag gcc aag aga ccc cta gaa     288
His Arg Leu Trp Ala His Lys Thr Tyr Lys Ala Lys Arg Pro Leu Glu
                 85                  90                  95 acc ctg ctc atg gta ttc cat agt ctg acg agc cag aac acc gtg cgg     336
Thr Leu Leu Met Val Phe His Ser Leu Thr Ser Gln Asn Thr Val Arg
            100                 105                 110 cac tgg gca agg gac cat cgg ttc cat cac aag tac agc gac aca gac     384
His Trp Ala Arg Asp His Arg Phe His His Lys Tyr Ser Asp Thr Asp
            115                 120                 125 gcc gac ccg cac aat gcg act cga ggt ttc ttc tac tcc cac gta ggc     432
Ala Asp Pro His Asn Ala Thr Arg Gly Phe Phe Tyr Ser His Val Gly
        130                 135                 140 tgg ctg ctg gtc aag aaa cac ccc gag gtc ctc aga cgg tcg aag acc     480
Trp Leu Leu Val Lys Lys His Pro Glu Val Leu Arg Arg Ser Lys Thr
145                 150                 155                 160 atc gac atg tcc gac att tac aac aat cca gtg ttg cgg ttc cag aaa     528
Ile Asp Met Ser Asp Ile Tyr Asn Asn Pro Val Leu Arg Phe Gln Lys
                165                 170                 175 aac tac ggc ctc cca gtg ata aca tta ttc gcc tac gtc ctc cca gct     576
Asn Tyr Gly Leu Pro Val Ile Thr Leu Phe Ala Tyr Val Leu Pro Ala
            180                 185                 190 ctc ata cca atg tac tgc tgg gaa gaa acc ctg aac aac gcc tgg cat     624
Leu Ile Pro Met Tyr Cys Trp Glu Glu Thr Leu Asn Asn Ala Trp His
            195                 200                 205 ata aac cta ctg cga atc ata gcc aac ctc cac gct tcc tgt ctt gtc     672
Ile Asn Leu Leu Arg Ile Ile Ala Asn Leu His Ala Ser Cys Leu Val
        210                 215                 220 aac agc gca gca cac gcc ttc ggt aac aaa ccg tac gac aag cac ata     720
Asn Ser Ala Ala His Ala Phe Gly Asn Lys Pro Tyr Asp Lys His Ile
225                 230                 235                 240 gca gcc acg caa atc tcc acc cta tcc ttc ata act tta ggg gag tgt     768
Ala Ala Thr Gln Ile Ser Thr Leu Ser Phe Ile Thr Leu Gly Glu Cys
                245                 250                 255 ttc cat aac tac cac cac gtc ttc ccc tgg gat tat agg acg gcg gag     816
Phe His Asn Tyr His His Val Phe Pro Trp Asp Tyr Arg Thr Ala Glu
            260                 265                 270 ctg ggg aat aat tgg ttg aac atg acg acg ctg ttc att gat ttt ttc     864
Leu Gly Asn Asn Trp Leu Asn Met Thr Thr Leu Phe Ile Asp Phe Phe
        275                 280                 285 gcg tgg gtc ggc tgg gcg tat gat ttg aag act gct tct gat ggg atg     912
Ala Trp Val Gly Trp Ala Tyr Asp Leu Lys Thr Ala Ser Asp Gly Met
    290                 295                 300
```

```
gtc gaa gct agg gct aaa agg acg ggg gat ggc acg aat ctg tgg ggg    960
Val Glu Ala Arg Ala Lys Arg Thr Gly Asp Gly Thr Asn Leu Trp Gly
305                 310                 315                 320 tgg ggg gat gag gat ctg ggg agg gag gag ggg ggt gag gaa gtg ttt   1008
Trp Gly Asp Glu Asp Leu Gly Arg Glu Glu Gly Gly Glu Glu Val Phe
                325                 330                 335 tac ggg tgg gga gat aga gat atg aag gat acc agt ggg gtt aga gtt   1056
Tyr Gly Trp Gly Asp Arg Asp Met Lys Asp Thr Ser Gly Val Arg Val
            340                 345                 350 tat tca caa gag taa                                                1071
Tyr Ser Gln Glu
            355

<210> SEQ ID NO 14
<211> LENGTH: 356
<212> TYPE: PRT
<213> ORGANISM: Planotortrix octo

<400> SEQUENCE: 14

Met Pro Pro Asn Ser Glu Glu Thr Val Leu Cys Glu Lys Glu Asp His
1               5                   10                  15

Glu Lys Leu Val Ala Pro Gln Ala Ala Thr Arg Lys His Glu Leu Ala
            20                  25                  30

Ile Val Pro Ile Ser Leu Phe Thr Tyr Trp His Val Ala Gly Leu Tyr
        35                  40                  45

Gly Leu Tyr Leu Ile Phe Ala Glu Ala Lys Trp Gln Thr Val Val Phe
    50                  55                  60

Thr Leu Phe Thr Tyr Asn Ala Gly Ile Leu Gly Ile Thr Ala Gly Ser
65                  70                  75                  80

His Arg Leu Trp Ala His Lys Thr Tyr Lys Ala Lys Arg Pro Leu Glu
                85                  90                  95

Thr Leu Leu Met Val Phe His Ser Leu Thr Ser Gln Asn Thr Val Arg
            100                 105                 110

His Trp Ala Arg Asp His Arg Phe His His Lys Tyr Ser Asp Thr Asp
        115                 120                 125

Ala Asp Pro His Asn Ala Thr Arg Gly Phe Phe Tyr Ser His Val Gly
    130                 135                 140

Trp Leu Leu Val Lys Lys His Pro Glu Val Leu Arg Arg Ser Lys Thr
145                 150                 155                 160

Ile Asp Met Ser Asp Ile Tyr Asn Asn Pro Val Leu Arg Phe Gln Lys
                165                 170                 175

Asn Tyr Gly Leu Pro Val Ile Thr Leu Phe Ala Tyr Val Leu Pro Ala
            180                 185                 190

Leu Ile Pro Met Tyr Cys Trp Glu Glu Thr Leu Asn Asn Ala Trp His
        195                 200                 205

Ile Asn Leu Leu Arg Ile Ile Ala Asn Leu His Ala Ser Cys Leu Val
    210                 215                 220

Asn Ser Ala Ala His Ala Phe Gly Asn Lys Pro Tyr Asp Lys His Ile
225                 230                 235                 240

Ala Ala Thr Gln Ile Ser Thr Leu Ser Phe Ile Thr Leu Gly Glu Cys
                245                 250                 255

Phe His Asn Tyr His His Val Phe Pro Trp Asp Tyr Arg Thr Ala Glu
            260                 265                 270

Leu Gly Asn Asn Trp Leu Asn Met Thr Thr Leu Phe Ile Asp Phe Phe
        275                 280                 285

Ala Trp Val Gly Trp Ala Tyr Asp Leu Lys Thr Ala Ser Asp Gly Met
```

-continued

```
                  290                 295                 300
Val Glu Ala Arg Ala Lys Arg Thr Gly Asp Gly Thr Asn Leu Trp Gly
305                 310                 315                 320

Trp Gly Asp Glu Asp Leu Gly Arg Glu Glu Gly Gly Glu Glu Val Phe
                325                 330                 335

Tyr Gly Trp Gly Asp Arg Asp Met Lys Asp Thr Ser Gly Val Arg Val
                340                 345                 350

Tyr Ser Gln Glu
        355

<210> SEQ ID NO 15
<211> LENGTH: 20
<212> TYPE: DNA
<213> ORGANISM: Artificial Sequence
<220> FEATURE:
<223> OTHER INFORMATION: Description of the synthetic sequence:
      oligonucleotide primer

<400> SEQUENCE: 15
atyachgccg gkkmycaymg                                               20

<210> SEQ ID NO 16
<211> LENGTH: 20
<212> TYPE: DNA
<213> ORGANISM: Artificial Sequence
<220> FEATURE:
<223> OTHER INFORMATION: Description of the synthetic sequence:
      oligonucleotide primer

<400> SEQUENCE: 16
ggraabdygt grtggwagtt                                               20

<210> SEQ ID NO 17
<211> LENGTH: 20
<212> TYPE: DNA
<213> ORGANISM: Artificial Sequence
<220> FEATURE:
<223> OTHER INFORMATION: Description of the synthetic sequence:
      oligonucleotide primer
<220> FEATURE:
<221> NAME/KEY: misc_feature
<222> LOCATION: (9)..(9)
<223> OTHER INFORMATION: n is a, c, g, t, unknown, or other
<220> FEATURE:
<221> NAME/KEY: misc_feature
<222> LOCATION: (18)..(18)
<223> OTHER INFORMATION: n is a, c, g, t, unknown, or other

<400> SEQUENCE: 17
ccccaycrnc tstggwcnca                                               20

<210> SEQ ID NO 18
<211> LENGTH: 25
<212> TYPE: DNA
<213> ORGANISM: Artificial Sequence
<220> FEATURE:
<223> OTHER INFORMATION: Description of the synthetic sequence:
      oligonucleotide primer

<400> SEQUENCE: 18
ccctctagar tgrrwarttr tgrwa                                         25

<210> SEQ ID NO 19
<211> LENGTH: 18
<212> TYPE: DNA
<213> ORGANISM: Artificial Sequence
```

-continued

```
<220> FEATURE:
<223> OTHER INFORMATION: Description of the synthetic sequence:
      oligonucleotide primer

<400> SEQUENCE: 19
taatacgact cactatag                                                      18

<210> SEQ ID NO 20
<211> LENGTH: 19
<212> TYPE: DNA
<213> ORGANISM: Artificial Sequence
<220> FEATURE:
<223> OTHER INFORMATION: Description of the synthetic sequence:
      oligonucleotide primer

<400> SEQUENCE: 20
acataactaa ttacatgat                                                     19

<210> SEQ ID NO 21
<211> LENGTH: 996
<212> TYPE: DNA
<213> ORGANISM: Pectinophora gossypiella
<220> FEATURE:
<221> NAME/KEY: CDS
<222> LOCATION: (1)..(993)
<223> OTHER INFORMATION: coding for delta-11-desaturase

<400> SEQUENCE: 21
```

| | | | | | | | | | | | | | | | | |
|---|---|---|---|---|---|---|---|---|---|---|---|---|---|---|---|---|
| atg | gcc | cct | tac | tta | aag | gag | ggt | aac | gca | att | ttg | gaa | aaa | tac | gaa | 48 |
| Met | Ala | Pro | Tyr | Leu | Lys | Glu | Gly | Asn | Ala | Ile | Leu | Glu | Lys | Tyr | Glu | |
| 1 | | | | 5 | | | | | 10 | | | | | 15 | | |
| acc | cta | aaa | gcg | cct | cag | gcg | gga | cca | aga | aaa | tat | caa | ata | att | tat | 96 |
| Thr | Leu | Lys | Ala | Pro | Gln | Ala | Gly | Pro | Arg | Lys | Tyr | Gln | Ile | Ile | Tyr | |
| | | 20 | | | | | 25 | | | | | 30 | | | | |
| ccg | aat | tta | ata | acg | ttt | gga | tat | gga | cac | atc | gcg | gca | ttg | tat | gga | 144 |
| Pro | Asn | Leu | Ile | Thr | Phe | Gly | Tyr | Gly | His | Ile | Ala | Ala | Leu | Tyr | Gly | |
| | 35 | | | | | 40 | | | | | 45 | | | | | |
| cta | tac | ctg | tgc | ttc | acc | tcg | gct | aaa | tgg | gct | act | att | ctt | ctt | gga | 192 |
| Leu | Tyr | Leu | Cys | Phe | Thr | Ser | Ala | Lys | Trp | Ala | Thr | Ile | Leu | Leu | Gly | |
| 50 | | | | | 55 | | | | | 60 | | | | | | |
| tac | atg | ttg | ttc | atc | gta | agt | gaa | ctc | ggc | atc | aca | gcg | ggc | gct | cac | 240 |
| Tyr | Met | Leu | Phe | Ile | Val | Ser | Glu | Leu | Gly | Ile | Thr | Ala | Gly | Ala | His | |
| 65 | | | | | 70 | | | | | 75 | | | | | 80 | |
| aga | ctg | tgg | gca | cac | aag | act | tac | aaa | gcc | aag | ctg | cct | ctg | gaa | att | 288 |
| Arg | Leu | Trp | Ala | His | Lys | Thr | Tyr | Lys | Ala | Lys | Leu | Pro | Leu | Glu | Ile | |
| | | | | 85 | | | | | 90 | | | | | 95 | | |
| ctc | cta | atg | gtg | ttc | aac | tca | att | gcc | ttt | caa | aac | act | gcc | gtc | acc | 336 |
| Leu | Leu | Met | Val | Phe | Asn | Ser | Ile | Ala | Phe | Gln | Asn | Thr | Ala | Val | Thr | |
| | | | 100 | | | | | 105 | | | | | 110 | | | |
| tgg | gtg | aag | gac | cac | cgc | gct | cac | cac | aag | tac | agc | gac | acc | gat | gca | 384 |
| Trp | Val | Lys | Asp | His | Arg | Ala | His | His | Lys | Tyr | Ser | Asp | Thr | Asp | Ala | |
| | | 115 | | | | | 120 | | | | | 125 | | | | |
| gac | cct | cac | aac | gcc | acg | aga | gga | ctc | ttc | tac | tca | cac | atc | ggg | tgg | 432 |
| Asp | Pro | His | Asn | Ala | Thr | Arg | Gly | Leu | Phe | Tyr | Ser | His | Ile | Gly | Trp | |
| | 130 | | | | | 135 | | | | | 140 | | | | | |
| cta | cta | gtc | aag | aaa | cac | ccc | gaa | gtc | att | aaa | cgc | gga | aaa | caa | atc | 480 |
| Leu | Leu | Val | Lys | Lys | His | Pro | Glu | Val | Ile | Lys | Arg | Gly | Lys | Gln | Ile | |
| 145 | | | | | 150 | | | | | 155 | | | | | 160 | |
| gat | tac | agc | gat | ata | tgt | aac | aat | cct | gta | ctg | agg | ttc | cag | aaa | aag | 528 |
| Asp | Tyr | Ser | Asp | Ile | Cys | Asn | Asn | Pro | Val | Leu | Arg | Phe | Gln | Lys | Lys | |
| | | | | 165 | | | | | 170 | | | | | 175 | | |
| tat | gcg | gtc | ccg | ttc | atc | ggg | acc | atg | tgc | ttc | gtg | ctt | ccg | act | gtg | 576 |
| Tyr | Ala | Val | Pro | Phe | Ile | Gly | Thr | Met | Cys | Phe | Val | Leu | Pro | Thr | Val | |

```
                    180                 185                 190
gta cca atg tac ttt tgg ggg gag agc ctg agg aac gcg tgg cat gtc      624
Val Pro Met Tyr Phe Trp Gly Glu Ser Leu Arg Asn Ala Trp His Val
        195                 200                 205 aac ctg ctt cgg tac gcg ctc agc ctc cat gcc acg ttc cta gtt aac      672
Asn Leu Leu Arg Tyr Ala Leu Ser Leu His Ala Thr Phe Leu Val Asn
210                 215                 220 agc gcc gcg cac tac tgg ggc acc aaa cct tac gat aag aac cta gtt      720
Ser Ala Ala His Tyr Trp Gly Thr Lys Pro Tyr Asp Lys Asn Leu Val
225                 230                 235                 240 gcg tca caa aac gtg tcc gtc tct ctg ttg acg agc ggc gaa gga tac      768
Ala Ser Gln Asn Val Ser Val Ser Leu Leu Thr Ser Gly Glu Gly Tyr
                245                 250                 255 cac aac tac cac cat gcg ttc cca tgg gac tac cgc gcc gcc gaa tta      816
His Asn Tyr His His Ala Phe Pro Trp Asp Tyr Arg Ala Ala Glu Leu
            260                 265                 270 ggc aac aac ttc gtc aac ttg acg acg aag ttt ata gat ttc ttc gcc      864
Gly Asn Asn Phe Val Asn Leu Thr Thr Lys Phe Ile Asp Phe Phe Ala
        275                 280                 285 tgg att ggc tgg gct tac gac ctt aag acg gtc cct aag gac ttg gtt      912
Trp Ile Gly Trp Ala Tyr Asp Leu Lys Thr Val Pro Lys Asp Leu Val
290                 295                 300 ata agc cgc atg aaa aga acc ggc gac ggt acc tcc cta tgg ggt tgg      960
Ile Ser Arg Met Lys Arg Thr Gly Asp Gly Thr Ser Leu Trp Gly Trp
305                 310                 315                 320 ggt gag aaa tat gac gga aaa cga atg aaa cgc taa                      996
Gly Glu Lys Tyr Asp Gly Lys Arg Met Lys Arg
                325                 330

<210> SEQ ID NO 22
<211> LENGTH: 331
<212> TYPE: PRT
<213> ORGANISM: Pectinophora gossypiella

<400> SEQUENCE: 22

Met Ala Pro Tyr Leu Lys Glu Gly Asn Ala Ile Leu Glu Lys Tyr Glu
1               5                   10                  15

Thr Leu Lys Ala Pro Gln Ala Gly Pro Arg Lys Tyr Gln Ile Ile Tyr
            20                  25                  30

Pro Asn Leu Ile Thr Phe Gly Tyr Gly His Ile Ala Ala Leu Tyr Gly
        35                  40                  45

Leu Tyr Leu Cys Phe Thr Ser Ala Lys Trp Ala Thr Ile Leu Leu Gly
    50                  55                  60

Tyr Met Leu Phe Ile Val Ser Glu Leu Gly Ile Thr Ala Gly Ala His
65                  70                  75                  80

Arg Leu Trp Ala His Lys Thr Tyr Lys Ala Lys Leu Pro Leu Glu Ile
                85                  90                  95

Leu Leu Met Val Phe Asn Ser Ile Ala Phe Gln Asn Thr Ala Val Thr
            100                 105                 110

Trp Val Lys Asp His Arg Ala His His Lys Tyr Ser Asp Thr Asp Ala
        115                 120                 125

Asp Pro His Asn Ala Thr Arg Gly Leu Phe Tyr Ser His Ile Gly Trp
    130                 135                 140

Leu Leu Val Lys Lys His Pro Glu Val Ile Lys Arg Gly Lys Gln Ile
145                 150                 155                 160

Asp Tyr Ser Asp Ile Cys Asn Asn Pro Val Leu Arg Phe Gln Lys Lys
                165                 170                 175
```

```
                    -continued
Tyr Ala Val Pro Phe Ile Gly Thr Met Cys Phe Val Leu Pro Thr Val
            180             185             190

Val Pro Met Tyr Phe Trp Gly Glu Ser Leu Arg Asn Ala Trp His Val
        195             200             205

Asn Leu Leu Arg Tyr Ala Leu Ser Leu His Ala Thr Phe Leu Val Asn
    210             215             220

Ser Ala Ala His Tyr Trp Gly Thr Lys Pro Tyr Asp Lys Asn Leu Val
225             230             235             240

Ala Ser Gln Asn Val Ser Val Ser Leu Leu Thr Ser Gly Glu Gly Tyr
            245             250             255

His Asn Tyr His His Ala Phe Pro Trp Asp Tyr Arg Ala Ala Glu Leu
            260             265             270

Gly Asn Asn Phe Val Asn Leu Thr Thr Lys Phe Ile Asp Phe Phe Ala
        275             280             285

Trp Ile Gly Trp Ala Tyr Asp Leu Lys Thr Val Pro Lys Asp Leu Val
    290             295             300

Ile Ser Arg Met Lys Arg Thr Gly Asp Gly Thr Ser Leu Trp Gly Trp
305             310             315             320

Gly Glu Lys Tyr Asp Gly Lys Arg Met Lys Arg
            325             330
```